(12) United States Patent
Nakamura et al.

(10) Patent No.: US 9,366,681 B2
(45) Date of Patent: Jun. 14, 2016

(54) POLYPEPTIDE MARKER FOR DIAGNOSIS OF ARTERIOSCLEROSIS, METHOD FOR DETECTION OF ARTERIOSCLEROSIS BY USING THE MAKER OR THE LIKE, AND KIT FOR DIAGNOSIS OF ARTERIOSCLEROSIS

(71) Applicants: Fujikura Kasei Co., Ltd., Tokyo (JP); National University Corporation Chiba University, Chiba-shi, Chiba (JP)

(72) Inventors: Rika Nakamura, Saitama (JP); Hideyuki Kuroda, Ora-gun (JP); Go Tomiyoshi, Kawaguchi (JP); Takaki Hiwasa, Chiba (JP); Masaki Takiguchi, Funabashi (JP); Naokatsu Saeki, Chiba (JP); Toshio Machida, Chiba (JP)

(73) Assignees: Fujikura Kasei Co., Ltd., Tokyo (JP); National University Corporation Chiba University, Chiba (JP)

( * ) Notice: Subject to any disclaimer, the term of this patent is extended or adjusted under 35 U.S.C. 154(b) by 0 days.

(21) Appl. No.: 13/783,892

(22) Filed: Mar. 4, 2013

(65) Prior Publication Data

US 2013/0183691 A1 Jul. 18, 2013

Related U.S. Application Data

(62) Division of application No. 13/058,456, filed as application No. PCT/JP2009/064363 on Aug. 14, 2009, now abandoned.

(30) Foreign Application Priority Data

Aug. 15, 2008 (JP) ................................ P2008-209210

(51) Int. Cl.
C12Q 1/68 (2006.01)
G01N 33/68 (2006.01)
C07K 14/47 (2006.01)

(52) U.S. Cl.
CPC ............ *G01N 33/6893* (2013.01); *C07K 14/47* (2013.01); *C12Q 1/6883* (2013.01); *C12Q 2600/158* (2013.01); *G01N 2800/323* (2013.01)

(58) Field of Classification Search
None
See application file for complete search history.

(56) References Cited

U.S. PATENT DOCUMENTS

| | | | |
|---|---|---|---|
| 6,265,543 B1 * | 7/2001 | Meissner | C07K 14/495 435/69.1 |
| 2002/0025553 A1 * | 2/2002 | Wei | 435/69.1 |
| 2004/0048286 A1 | 3/2004 | Lee | |
| 2006/0013813 A1 | 1/2006 | Mezes et al. | |
| 2007/0015271 A1 | 1/2007 | Rosen et al. | |
| 2007/0072175 A1 | 3/2007 | Cooper et al. | |
| 2007/0078101 A1 * | 4/2007 | Brivanlou et al. | 514/44 |
| 2007/0190586 A1 | 8/2007 | Holvoet et al. | |

FOREIGN PATENT DOCUMENTS

| | | |
|---|---|---|
| JP | 08160042 | 6/1996 |
| JP | 10142226 A | 5/1998 |
| JP | 09203736 A | 8/1998 |
| JP | 11346782 A | 12/1999 |
| JP | 2000503764 A | 3/2000 |
| JP | 2000184885 A | 7/2000 |
| JP | 2000206113 A | 7/2000 |
| JP | 2000333674 A | 12/2000 |
| JP | 2001249128 A | 9/2001 |
| JP | 2002017353 A | 1/2002 |
| JP | 2002048790 A | 2/2002 |
| JP | 2002055106 A | 2/2002 |
| JP | 2002131313 A | 5/2002 |
| JP | 2002142781 A | 5/2002 |
| JP | 2002181820 A | 6/2002 |
| JP | 2002238589 A | 8/2002 |
| JP | 2002277461 A | 9/2002 |
| JP | 2002308900 A | 10/2002 |
| JP | 2003189872 A | 7/2003 |
| JP | 2003304873 A | 10/2003 |

(Continued)

OTHER PUBLICATIONS

Korean Intellectual Property Office, Notice of Decision to Grant Patent issued in corresponding Korean Patent Application No. 10-2011-7001433 and English-language translation (Jan. 23, 2015).

(Continued)

*Primary Examiner* — Anne Gussow
(74) *Attorney, Agent, or Firm* — Wood, Herron & Evans, LLP

(57) ABSTRACT

Disclosed are: a polypeptide marker for diagnosing arteriosclerosis; a gene marker for diagnosing arteriosclerosis; an antibody; a probe for detecting an arteriosclerosis marker gene; a DNA microarray or a DNA chip for detecting an arteriosclerosis marker gene; a method for detecting arteriosclerosis; and a kit for diagnosing arteriosclerosis; with which an arteriosclerotic lesion can be detected with much improved accuracy. Specifically disclosed are: a polypeptide marker for diagnosing arteriosclerosis, which comprises a polypeptide having an amino acid sequence set forth in any one of SEQ ID NOs: 1, 3, 5, 7, 9, 11, 13, 15, 17, 19, 21, 23, 25, 27, 29, 31, 33, and 35 of the Sequence Listing, or a partial amino acid sequence thereof; a gene which encodes the amino acid sequence; a probe for detecting the gene; a DNA microarray or a DNA chip comprising the probe; an antibody bindable to the polypeptide as an antigen; a kit comprising any one of the above-mentioned items; and a method for detecting arteriosclerosis by using any one of the above-mentioned items.

1 Claim, 1 Drawing Sheet

(56) References Cited

FOREIGN PATENT DOCUMENTS

| JP | 2003310281 A | 11/2003 |
| JP | 2005168498 A | 6/2005 |
| JP | 2007010567 A | 1/2007 |
| JP | 2007278907 A | 10/2007 |
| KR | 20080090610 A | 10/2008 |
| WO | 9722880 A1 | 6/1997 |
| WO | 03104395 A2 | 12/2003 |
| WO | 2006048291 A2 | 5/2006 |
| WO | 2006102979 A2 | 10/2006 |

OTHER PUBLICATIONS

GenBank Accession No. NP_003683.2 (Feb. 10, 2008) (2 pages).
Office Action issued in Korean Patent Application No. 10-2011-7001433; Jul. 1, 2013; 8 pages; Korean Intellectual property Office.
GenBan_AAE43124; Feb. 14, 2001.
Korean Intellectual Property Office, Office Action issued in corresponding Korean Patent Application No. 10-2011-7001433, dated Jun. 25, 2014, 9 pages.
Harms, Paul W., et al., Tomoregulin-1 (TMEFF1) Inhibits Nodal Signaling Through Direct Binding to the Nodal Coreceptor Cripto, Genes & Development, 2003, pp. 2624-2629, vol. 17, Cold Spring Harbor Laboratory Press.
GenBank, "Predicted: *Homo sapiens* Similar to LIM and Senescent Cell Antigen-like Domains 1 (LOC729260), mRNA," Accession XM_001129783 (Feb. 29, 2008) URL: http://www.ncbi.nlm.nih.gov/nuccore/XM_001129783.2?report=genbank.
GenBank, "*Homo sapiens* Tubulin, Beta 2C (TUBB2C), mRNA," Accession NM_006088 (Apr. 29, 2008) URL: http://www.ncbi.nlm.nih.gov/nuccore/68051719?sat=13&satkey=4913042.
GenBank, "*Homo sapiens* KIAA0020 (KIAA0020), mRNA," Accession NM_014878 (May 1, 2008) URL: http://www.ncbi.nlm.nih.gov/nuccore/109948282?sat=12&satkey=6397554.
GenBank, "*Homo sapiens* Differentially Expressed in FDCP 8 Homolog (mouse) (DEF8), Transcript Variant 1, mRNA," Accession NM_207514 (Feb. 11, 2008), URL: http://www.ncbi.nlm.nih.gov/nuccore/46447819?sat=13&satkey=9233161.
GenBank, "*Homo sapiens* SWI/SNF Related, Matrix Associated, Actin Dependent Regulator of Chromatin, Subfamily a, Member 4 (SMARCA4), Transcript Variant 6, mRNA," Accession NM_001128847 (Aug. 10, 2008) URL: http://www.ncbi.nlm.nih.gov/nuccore/192807317?sat=12&satkey=6283470.
GenBank, "*Homo sapiens* RanBP-type and C3HC4-type Zinc Finger Containing 1 (RBCK1), Transcript Variant 2, mRNA," Accession NM_031229 (Jun. 22, 2008) URL: http://www.ncbi.nlm.nih.gov/nuccore/144953897?sat=12&satkey=8748316.
GenBank, "*Homo sapiens* Rho-associated, Coiled-coil Containing Protein Kinase 1 (ROCK1), mRNA," Accession NM 005406 (Aug. 10, 2008) URL: http://www.ncbi.nlm.nih.gov/nuccore/112382209?sat=12&satkey=6437871.
GenBank, "*Homo sapiens* Bromodomain Adjacent to Zinc Finger Domain, 1B (BAZ1B), mRNA," Accession NM_032408 (Feb. 10, 2008) URL: http://www.ncbi.nlm.nih.gov/nuccore/115387100?sat=12&satkey=10261291.
GenBank, "*Homo sapiens* Zuotin Related Factor 1 (ZRF1), mRNA," Accession NM_014377 (Jan. 13, 2008) URL: http://www.ncbi.nlm.nih.gov/nuccore/94538369?sat=12&satkey=1599023.
GenBank, "*Homo sapiens* Chromobox Homolog 1 (HP1 Beta Homolog *Drosophila*) (CBX1), Transcript Variant 1, mRNA," Accession NM_006807 (Aug. 10, 2008) URL: http://www.ncbi.nlm.nih.gov/nuccore/187960060? sat=12&satkey=6643917.
Japanese Patent Office, Notice of Reasons for Rejection issued in corresponding Japanese Patent Application No. 2010-524759 and English-language translation, mailed Nov. 11, 2014 (10 pages).
Fuster, V. et al., The Pathogenesis of Coronary Artery Disease and the Acute Coronary Syndromes, The New England Journal of Medicine, 1992, pp. 242-250, vol. 326, No. 4.
Kuno, K. et al., Molecular Cloning of a Gene Encoding a New Type of Metalloproteinase-disintegrin Family Protein with Thrombospondin Motifs as an Inflammation Associated Gene, The Journal of Biological Chemistry, 1997, pp. 556-562, vol. 272, No. 1.
International Search Report issued in PCT Applilcation No. JP2009/064363, dated Nov. 17, 2009, 6 pages.
European Search Report issued in European Patent Application No. 09806761.4, dated Dec. 29, 2011, 12 pages.
GenBank Accession No. NP_003683.2 (2008.92.10) (2 pages).
GenBank Accession No. NM_003692.2 (Feb. 10, 2008) (5 pages).
Office Action cited in counterpart Chinese Application No. 200980128162.0 mailed on Jan. 7, 2013 with English translation (12 pages).
PARK2 co-regulated [*Homo sapiens*] [online]. GenBank: AAH30642.1 (Jan. 25, 2007); Retrieved from internet on Nov. 9, 2011; <URL:http://www.ncbi.nlm.nih.gov/protein/21040407.
*Homo sapiens* PARK2 co-regulated, mRNA (cDNA clone MGC:26712 Image:4823539, complete cds; [online]; GenBank: BC030642.2 (Jan. 25, 2007). Retrieved from the internet on Nov. 9, 2011: <URL: http://www.ncbi.nlm.nih.gov/nuccore/BC030642.
Notice of Office Action issued in Korean Patent Application No. 10-2011-7001433; Oct. 17, 2012; 14 pages; Korean Intellectual Property Office.
Meisserner et al., Transforming growth factor alpha-HI, Sep. 3, 1997. ID No. AAW09406.
European Patent Office, Extended Search Report issued in corresponding European Patent Application No. 15199553.7 dated Apr. 15, 2016.

\* cited by examiner

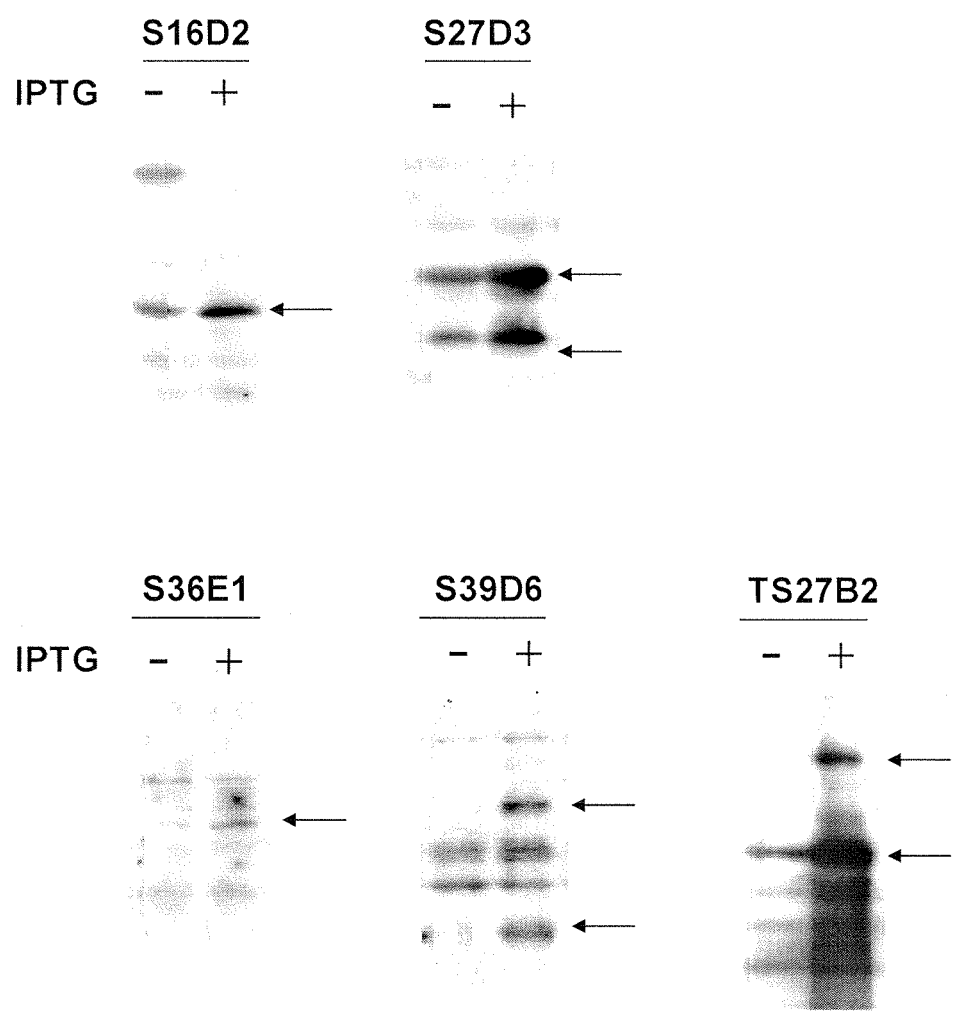

SEQUENCE LISTING

<160> NUMBER OF SEQ ID NOS: 36

<210> SEQ ID NO 1
<211> LENGTH: 568
<212> TYPE: PRT
<213> ORGANISM: Homo sapiens

<400> SEQUENCE: 1

```
Met Glu Ser Phe Leu Leu Asp Asp Ile Ser Ser Val Ile Gln Asn Lys
 1               5                  10                  15

Gly Ile Glu Arg Ile Ile Ser Pro Met Ile Val Gln Leu Cys His Leu
             20                  25                  30

Leu Ile Ser Met Glu Arg Lys Glu Val Glu Asn Glu Val Phe Ala Ser
             35                  40                  45

Leu Glu Lys Met Ala Glu Glu Leu Ala Lys Ala Cys Glu Asp Phe Val
     50                  55                  60

Gln Val Val Lys Ser Ser Gly Asn Thr Glu Ala Val Ser Val Ser Pro
 65                  70                  75                  80

Val Ile Val Asn Ala Ala Leu Val Phe Gln Lys Ala Val Val Val Trp
                 85                  90                  95

Val Phe Lys Ser Glu Lys His Gly Ile Val Asp Glu Val Leu Trp Gln
            100                 105                 110

Ile Cys Lys Ala Arg Val Asp Ile Ser Phe Ser Trp Arg Leu Thr Arg
            115                 120                 125

Leu Thr Cys Val Gly Thr Val Gly Val Thr Leu Ala Gly Lys Gln Gly
        130                 135                 140

Gly Leu Asp Ile Val Ser Pro Gly Ser Val Ser Cys His Ser His Pro
145                 150                 155                 160

Cys Ala Gln Ser Ser Gln Ala Pro Thr Met Ala Phe Ser Gly Arg Ala
                165                 170                 175

Arg Pro Cys Ile Ile Pro Glu Asn Glu Ile Pro Arg Ala Ala Leu
            180                 185                 190

Asn Thr Val His Glu Ala Asn Gly Thr Glu Asp Glu Arg Ala Val Ser
                195                 200                 205

Lys Leu Gln Arg Arg His Ser Asp Val Lys Val Tyr Lys Glu Phe Cys
        210                 215                 220

Asp Phe Tyr Ala Lys Phe Asn Met Ala Asn Ala Leu Ala Ser Ala Thr
225                 230                 235                 240

Cys Glu Arg Cys Lys Gly Gly Phe Ala Pro Ala Glu Thr Ile Val Asn
                245                 250                 255

Ser Asn Gly Glu Leu Tyr His Glu Gln Cys Phe Val Cys Ala Gln Cys
            260                 265                 270

Phe Gln Gln Phe Pro Glu Gly Leu Phe Tyr Glu Phe Glu Gly Arg Lys
        275                 280                 285

Tyr Cys Glu His Asp Phe Gln Met Leu Phe Ala Pro Cys Cys His Gln
    290                 295                 300

Cys Gly Glu Phe Ile Ile Gly Arg Val Ile Lys Ala Met Asn Asn Ser
305                 310                 315                 320

Trp His Pro Glu Cys Phe Arg Cys Asp Leu Cys Gln Glu Val Leu Ala
                325                 330                 335

Asp Ile Gly Phe Val Lys Asn Ala Gly Arg His Leu Cys Arg Pro Cys
            340                 345                 350

His Asn Arg Glu Lys Ala Arg Gly Leu Gly Lys Tyr Ile Cys Gln Lys
        355                 360                 365
```

```
Cys His Ala Ile Ile Asp Glu Gln Pro Leu Ile Phe Lys Asn Asp Pro
    370                 375                 380

Tyr His Pro Asp His Phe Asn Cys Ala Asn Cys Gly Lys Asp Leu Thr
385                 390                 395                 400

Ala Asp Ala Gln Glu Leu Lys Gly Glu Leu Tyr Cys Leu Pro Cys His
                405                 410                 415

Asp Lys Met Gly Val Pro Ile Cys Gly Ala Cys Arg Arg Pro Ile Glu
            420                 425                 430

Gly Arg Val Val Asn Ala Met Gly Lys Gln Trp His Val Glu His Phe
                435                 440                 445

Val Cys Ala Lys Cys Glu Lys Pro Phe Leu Gly His Arg His Tyr Glu
450                 455                 460

Arg Lys Gly Leu Ala Tyr Cys Glu Thr His Tyr Asn Gln Leu Phe Gly
465                 470                 475                 480

Asp Val Cys Phe His Cys Asn Arg Val Ile Glu Gly Asp Val Val Ser
                485                 490                 495

Ala Leu Asn Lys Ala Trp Cys Val Asn Cys Phe Ala Cys Ser Thr Cys
                500                 505                 510

Asn Thr Lys Leu Thr Leu Lys Asp Lys Phe Val Glu Ile Asp Leu Lys
                515                 520                 525

Pro Val Cys Lys His Cys Tyr Glu Lys Met Pro Glu Glu Phe Lys Arg
            530                 535                 540

Arg Leu Ala Lys Arg Glu Arg Glu Ala Lys Asp Lys Asp Lys Gln Lys
545                 550                 555                 560

Lys Lys Lys Pro Val Cys Leu Leu
                565
```

```
<210> SEQ ID NO 2
<211> LENGTH: 1707
<212> TYPE: DNA
<213> ORGANISM: Homo sapiens

<400> SEQUENCE: 2
atggagtctt tcctcttgga tgacatcagc tctgtgatac agaacaaagg cattgagaga    60
atcatctcac caatgatcgt tcagctttgc catctgctca tctcaatgga gaggaaagaa   120
gtggagaatg aagtatttgc ctcgttggag aagatggctg aggaattggc gaaagcttgt   180
gaagacttcg tgcaagttgt caaaagttca ggcaacacgg aagctgtgtc tgtttctcct   240
gtcattgtaa atgcagccct ggtctttcaa aaagctgtgg ttgtgtgggt ctttaagagt   300
gaaaagcacg gcattgttga tgaagtcttg tggcaaatat gcaaggcacg tgtggatatt   360
tctttctctt ggaggcttac aaggctgacg tgcgtgggaa cagtgggagt gaccctggct   420
gggaagcagg gaggcctgga tattgtttct cctggctctg tgtcctgcca ttctcatccc   480
tgtgctcaga gctctcaagc acccacgatg gccttctcag gccgagcgcg ccctgcatt    540 atcccagaga acgaagaaat cccccgagca gcccttaaca ctgtccacga ggccaatggg   600
accgaggacg agagggctgt tccaaactg cagcgcaggc acagtgacgt gaaagtctac   660
aaggagttct gtgactttta tgcgaaattc aacatggcca acgccctggc cagcgccact   720
tgcgagcgct gcaagggcgg cttttgcgcc gctgagacga tcgtgaacag taatggggag   780
ctgtaccatg agcagtgttt cgtgtgcgct cagtgcttcc agcagttccc agaaggactc   840
ttctatgagt ttgaaggaag aaagtactgt gaacatgact ttcagatgct cttttgcccct   900 tgctgtcatc agtgtggtga attcatcatt ggccgagtta tcaaagccat gaataacagc   960
```

-continued

```
tggcatccgg agtgcttccg ctgtgacctc tgccaggaag ttctggcaga tatcgggttt    1020
gtcaagaatg ctgggagaca cctgtgtcgc ccctgtcata atcgtgagaa agccagaggc    1080
cttgggaaat acatctgcca gaaatgccat gctatcatcg atgagcagcc tctgatattc    1140
aagaacgacc cctaccatcc agaccatttc aactgcgcca actgcgggaa ggatctgact    1200
gccgatgcac aggagctgaa aggggagcta tactgcctgc catgccatga taaaatgggg    1260
gtccccatct gtggcgcttg ccgacggccc atcgaagggc gtgtggtgaa cgccatgggc    1320
aagcagtggc atgtggagca ttttgtttgt gccaagtgtg agaaacccct tcttggacat    1380
cgccattatg agaggaaagg cctggcgtat tgtgaaactc actataacca gctatttggt    1440
gatgtttgct tccactgcaa tcgtgttata gaaggtgatg tggtctctgc tcttaataag    1500
gcctggtgcg tgaactgctt tgcctgttct acctgcaaca ctaaattaac actcaaggat    1560
aagtttgttg aaattgacct aaagccagtc tgcaaacact gttatgagaa aatgccagaa    1620
gaatttaaga ggcgacttgc caaacgggag agagaagcaa aggataagga caagcagaaa    1680
aagaaaaagc cagtctgttt attgtaa                                       1707
```

<210> SEQ ID NO 3
<211> LENGTH: 445
<212> TYPE: PRT
<213> ORGANISM: Homo sapiens

<400> SEQUENCE: 3

```
Met Arg Glu Ile Val His Leu Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Glu Arg Ile Asn
        35                  40                  45

Val Tyr Tyr Asn Glu Ala Thr Gly Gly Lys Tyr Val Pro Arg Ala Val
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240
```

```
Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Met Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ser Ala Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Phe Glu Glu Glu Ala Glu Glu Val Ala
        435                 440                 445

<210> SEQ ID NO 4
<211> LENGTH: 1338
<212> TYPE: DNA
<213> ORGANISM: Homo sapiens

<400> SEQUENCE: 4
atgagggaaa tcgtgcactt gcaggccggg cagtgcggca accaaatcgg cgccaagttt      60
tgggaggtga tcagcgatga gcacggcatc gaccccacgg gcacctacca cggggacagc     120
gacctgcagc tggaacgcat caacgtgtac tacaatgagg ccaccggcgg caagtacgtg     180
ccccgcgccg tgctcgtgga tctggagccc ggcaccatgg actccgtgcg ctcggggccc     240
ttcgggcaga tcttccggcc ggacaacttc gttttcggtc agagtggtgc tgggaacaac     300
tgggccaagg gcactacac agaaggcgcg gagctggtgg actcggtgct ggatgttgtg     360
agaaaggagg ctgagagctg tgactgcctg cagggtttcc agctgaccca ctccctgggt     420 gggggactg gtctgggat gggtaccctc ctcatcagca gatccgggga ggagtaccca     480
gacaggatca tgaacacgtt tagtgtggtg ccttcgccca agtgtcaga cacagtggtg     540 gagccctaca cgccaccct tcagtccac cagctcgtag aaaacacaga cgagacctac     600
tgcattgata cgaagctct ctacgacatt tgcttcagaa ccctaaagct gaccacgccc     660
acctatggtg acctgaacca cctggtgtct gctaccatga gtgggtcac cacctgcctg     720 cgcttcccag ccagctcaa tgctgacctg cggaagctgg ctgtgaacat ggtcccgttt     780
ccccggctgc acttcttcat gccgggctttt gccccactga ccagccgggg cagccagcag     840
taccgggcgc tgaccgtgcc cgagctcacc agcagatgt tgatgccaa gaacatgatg     900 gctgcctgcg accccgcca tggccgctac ctgacggttg ccgccgtgtt caggggccgc     960
```

```
atgtccatga aggaggtgga tgagcaaatg cttaatgtcc aaaacaaaaa cagcagctat    1020
tttgttgagt ggatccccaa caatgtgaaa acggctgtct gtgacatccc acctcggggg    1080
ctaaaaatgt ccgccacctt cattggcaac agcacggcca tccaggagct gttcaagcgc    1140
atctccgagc agttcacggc catgttccgg cgcaaggcct tcctgcactg gtacacgggc    1200
gagggcatgg acgagatgga gttcaccgag gccgagagca acatgaatga cctggtgtcc    1260
gagtaccagc agtaccagga tgccacagcc gaggaggagg gcgagttcga ggaggaggct    1320
gaggaggagg tggcctag                                                  1338
```

```
<210> SEQ ID NO 5
<211> LENGTH: 648
<212> TYPE: PRT
<213> ORGANISM: Homo sapiens

<400> SEQUENCE: 5

Met Glu Val Lys Gly Lys Lys Gln Phe Thr Gly Lys Ser Thr Lys Thr
1               5                   10                  15

Ala Gln Glu Lys Asn Arg Phe His Lys Asn Ser Asp Ser Gly Ser Ser
            20                  25                  30

Lys Thr Phe Pro Thr Arg Lys Val Ala Lys Glu Gly Gly Pro Lys Val
        35                  40                  45

Thr Ser Arg Asn Phe Glu Lys Ser Ile Thr Lys Leu Gly Lys Lys Gly
    50                  55                  60

Val Lys Gln Phe Lys Asn Lys Gln Gln Gly Asp Lys Ser Pro Lys Asn
65                  70                  75                  80

Lys Phe Gln Pro Ala Asn Lys Phe Asn Lys Arg Lys Phe Gln Pro
                85                  90                  95

Asp Gly Arg Ser Asp Glu Ser Ala Ala Lys Lys Pro Lys Trp Asp Asp
            100                 105                 110

Phe Lys Lys Lys Lys Lys Glu Leu Lys Gln Ser Arg Gln Leu Ser Asp
        115                 120                 125

Lys Thr Asn Tyr Asp Ile Val Val Arg Ala Lys Gln Met Trp Glu Ile
    130                 135                 140

Leu Arg Arg Lys Asp Cys Asp Lys Glu Lys Arg Val Leu Met Ser
145                 150                 155                 160

Asp Leu Gln Lys Leu Ile Gln Gly Lys Ile Lys Thr Ile Ala Phe Ala
                165                 170                 175

His Asp Ser Thr Arg Val Ile Gln Cys Tyr Ile Gln Tyr Gly Asn Glu
            180                 185                 190

Glu Gln Arg Lys Gln Ala Phe Glu Glu Leu Arg Asp Leu Val Glu
        195                 200                 205

Leu Ser Lys Ala Lys Tyr Ser Arg Asn Ile Val Lys Lys Phe Leu Met
    210                 215                 220

Tyr Gly Ser Lys Pro Gln Ile Ala Glu Ile Ile Arg Ser Phe Lys Gly
225                 230                 235                 240

His Val Arg Lys Met Leu Arg His Ala Glu Ala Ser Ala Ile Val Glu
                245                 250                 255

Tyr Ala Tyr Asn Asp Lys Ala Ile Leu Glu Gln Arg Asn Met Leu Thr
            260                 265                 270

Glu Glu Leu Tyr Gly Asn Thr Phe Gln Leu Tyr Lys Ser Ala Asp His
        275                 280                 285

Arg Thr Leu Asp Lys Val Leu Glu Val Gln Pro Glu Lys Leu Glu Leu
    290                 295                 300
```

| | | | | | | | | | | | | |
|---|---|---|---|---|---|---|---|---|---|---|---|---|
| Ile | Met | Asp | Glu | Met | Lys | Gln | Ile | Leu | Thr | Pro | Met | Ala | Gln | Lys | Glu |
| 305 | | | | 310 | | | | | 315 | | | | | 320 | |

Ile Met Asp Glu Met Lys Gln Ile Leu Thr Pro Met Ala Gln Lys Glu
305                 310                 315                 320

Ala Val Ile Lys His Ser Leu Val His Lys Val Phe Leu Asp Phe Phe
                325                 330                 335

Thr Tyr Ala Pro Pro Lys Leu Arg Ser Glu Met Ile Glu Ala Ile Arg
            340                 345                 350

Glu Ala Val Val Tyr Leu Ala His Thr His Asp Gly Ala Arg Val Ala
                355                 360                 365

Met His Cys Leu Trp His Gly Thr Pro Lys Asp Arg Lys Val Ile Val
        370                 375                 380

Lys Thr Met Lys Thr Tyr Val Glu Lys Val Ala Asn Gly Gln Tyr Ser
385                 390                 395                 400

His Leu Val Leu Leu Ala Ala Phe Asp Cys Ile Asp Asp Thr Lys Leu
                405                 410                 415

Val Lys Gln Ile Ile Ile Ser Glu Ile Ile Ser Ser Leu Pro Ser Ile
            420                 425                 430

Val Asn Asp Lys Tyr Gly Arg Lys Val Leu Leu Tyr Leu Leu Ser Pro
            435                 440                 445

Arg Asp Pro Ala His Thr Val Arg Glu Ile Ile Glu Val Leu Gln Lys
450                 455                 460

Gly Asp Gly Asn Ala His Ser Lys Lys Asp Thr Glu Val Arg Arg Arg
465                 470                 475                 480

Glu Leu Leu Glu Ser Ile Ser Pro Ala Leu Leu Ser Tyr Leu Gln Glu
                485                 490                 495

His Ala Gln Glu Val Val Leu Asp Lys Ser Ala Cys Val Leu Val Ser
            500                 505                 510

Asp Ile Leu Gly Ser Ala Thr Gly Asp Val Gln Pro Thr Met Asn Ala
        515                 520                 525

Ile Ala Ser Leu Ala Ala Thr Gly Leu His Pro Gly Gly Lys Asp Gly
        530                 535                 540

Glu Leu His Ile Ala Glu His Pro Ala Gly His Leu Val Leu Lys Trp
545                 550                 555                 560

Leu Ile Glu Gln Asp Lys Lys Met Lys Glu Asn Gly Arg Glu Gly Cys
                565                 570                 575

Phe Ala Lys Thr Leu Val Glu His Val Gly Met Lys Asn Leu Lys Ser
            580                 585                 590

Trp Ala Ser Val Asn Arg Gly Ala Ile Ile Leu Ser Ser Leu Leu Gln
            595                 600                 605

Ser Cys Asp Leu Glu Val Ala Asn Lys Val Lys Ala Ala Leu Lys Ser
        610                 615                 620

Leu Ile Pro Thr Leu Glu Lys Thr Lys Ser Thr Ser Lys Gly Ile Glu
625                 630                 635                 640

Ile Leu Leu Glu Lys Leu Ser Thr
                645

<210> SEQ ID NO 6
<211> LENGTH: 1947
<212> TYPE: DNA
<213> ORGANISM: Homo sapiens

<400> SEQUENCE: 6
atggaagtta aagggaaaaa gcaattcaca ggaaagagta caaagacagc acaagaaaaa    60
aacagatttc ataaaatag tgattctggt tcttcaaaga catttccaac aaggaaagtt    120
gctaaagaag gtggacctaa agtcacatct aggaactttg agaaagtat cacaaaactt    180

```
gggaaaaagg gtgtaaagca gttcaagaat aagcagcaag gggacaaatc accaaagaac    240
aaattccagc cggcaaataa attcaacaag agagaaaat tccagccaga tggtagaagc     300
gatgaatcag cagccaagaa gcccaaatgg gatgacttca aaaagaagaa gaaagaactg    360
aagcaaagca gacaactcag tgataaaacc aactatgaca ttgttgttcg ggcaaagcag    420
atgtgggaga ttttaagaag aaaagactgt gacaaagaaa aaagagtaaa gttaatgagt    480
gatttgcaga gttgattca agggaaaatt aaaactattg catttgcaca cgattcaact    540
cgtgtgatcc agtgttacat tcagtatggt aatgaagaac agagaaaaca ggcttttgaa    600
gaattgcgag atgatttggt tgagttaagt aaagccaaat attcgagaaa tattgttaag    660
aaatttctca tgtatggaag taaaccacag attgcagaga taatcagaag ttttaaaggc    720
cacgtgagga agatgctgcg gcatgcggaa gcatcagcca tcgtggagta cgcatacaat    780
gacaaagcca ttttggagca gaggaacatg ctgacggaag agctctatgg gaacacattt    840
cagctttaca gtcagcaga tcaccgaact ctggacaaag tgttagaggt acagccagaa    900
aaattagaac ttattatgga tgaaatgaaa cagattctaa ctccaatggc ccaaaaggaa    960
gctgtgatta agcactcatt ggtgcataaa gtattcttgg acttttttac ctatgcaccc   1020
cccaaactca gatcagaaat gattgaagcc atccgcgaag cggtggtcta cctggcacac   1080
acacacgatg cgccagagt ggccatgcac tgcctgtggc atggcacgcc caaggacagg    1140
aaagtgattg tgaaaacaat gaagacttat gttgaaaagg tggctaatgg ccaatactcc   1200
catttggttt tactgcggc atttgattgt attgatgata ctaagcttgt gaagcagata    1260
atcatatcag aaattatcag ttcattgcct agcatagtaa atgacaaata tggaaggaag   1320
gtcctattgt acttactaag ccccagagat cctgcacata cagtacgaga atcattgaa    1380 gttctgcaaa aaggagatgg aaatgcacac agtaagaaag atacagaggt ccgcagacgg   1440
gagctcctag aatccatttc tccagctttg ttaagctacc tgcaagaaca cgcccaagaa   1500
gtggtgctag ataagtctgc gtgtgtgttg gtgtctgaca ttctgggatc tgccactgga   1560
gacgttcagc ctaccatgaa tgccatcgcc agcttggcag caacaggact gcatcctggt   1620
ggcaaggacg gagagcttca cattgcagaa catcctgcag acatctagt tctgaagtgg    1680 ttaatagagc aagataaaaa gatgaaagaa aatgggagag aaggttgttt tgcaaaaaca   1740
cttgtagagc atgttggtat gaagaacctg aagtcctggg ctagtgtaaa tcgaggtgcc   1800
attattcttt ctagcctcct ccagagttgt gacctggaag ttgcaaacaa agtcaaagct   1860
gcactgaaaa gcttgattcc tacattggaa aaaaccaaaa gcaccagcaa aggaatagaa   1920
attctacttg aaaaactgag cacatag                                       1947
```

<210> SEQ ID NO 7
<211> LENGTH: 512
<212> TYPE: PRT
<213> ORGANISM: Homo sapiens

<400> SEQUENCE: 7

Met Ala Ile Leu Ser Leu Arg Ala Pro Gly Pro Trp Gln Ala Met Gln
1               5                   10                  15

Val Trp Ala Asp Arg Thr Leu Leu Thr Pro His Thr Gly Val Thr Ser
            20                  25                  30

Gln Val Leu Gly Val Ala Ala Ala Val Met Thr Pro Leu Pro Gly Gly
        35                  40                  45

His Ala Ala Gly Arg Thr Arg Glu Ala Arg Trp Asp Ala Met Glu Tyr

```
                  50                  55                  60
Asp Glu Lys Leu Ala Arg Phe Arg Gln Ala His Leu Asn Pro Phe Asn
 65                  70                  75                  80

Lys Gln Ser Gly Pro Arg Gln His Glu Gln Gly Pro Gly Glu Glu Val
                 85                  90                  95

Pro Asp Val Thr Pro Glu Glu Ala Leu Pro Glu Leu Pro Pro Gly Glu
                100                 105                 110

Pro Glu Phe Arg Cys Pro Glu Arg Val Met Asp Leu Gly Leu Ser Glu
                115                 120                 125

Asp His Phe Ser Arg Pro Val Gly Leu Phe Leu Ala Ser Asp Val Gln
                130                 135                 140

Gln Leu Arg Gln Ala Ile Glu Glu Cys Lys Gln Val Ile Leu Glu Leu
145                 150                 155                 160

Pro Glu Gln Ser Glu Lys Gln Lys Asp Ala Val Val Arg Leu Ile His
                165                 170                 175

Leu Arg Leu Lys Leu Gln Glu Leu Lys Asp Pro Asn Glu Asp Glu Pro
                180                 185                 190

Asn Ile Arg Val Leu Leu Glu His Arg Phe Tyr Lys Glu Lys Ser Lys
                195                 200                 205

Ser Val Lys Gln Thr Cys Asp Lys Cys Asn Thr Ile Ile Trp Gly Leu
210                 215                 220

Ile Gln Thr Trp Tyr Thr Cys Thr Gly Cys Tyr Tyr Arg Cys His Ser
225                 230                 235                 240

Lys Cys Leu Asn Leu Ile Ser Lys Pro Cys Val Ser Ser Lys Val Ser
                245                 250                 255

His Gln Ala Glu Tyr Glu Leu Asn Ile Cys Pro Glu Thr Gly Leu Asp
                260                 265                 270

Ser Gln Asp Tyr Arg Cys Ala Glu Cys Arg Ala Pro Ile Ser Leu Arg
                275                 280                 285

Gly Val Pro Ser Glu Ala Arg Gln Cys Asp Tyr Thr Gly Gln Tyr Tyr
                290                 295                 300

Cys Ser His Cys His Trp Asn Asp Leu Ala Val Ile Pro Ala Arg Val
305                 310                 315                 320

Val His Asn Trp Asp Phe Glu Pro Arg Lys Val Ser Arg Cys Ser Met
                325                 330                 335

Arg Tyr Leu Ala Leu Met Val Ser Arg Pro Val Leu Arg Leu Arg Glu
                340                 345                 350

Ile Asn Pro Leu Leu Phe Ser Tyr Val Glu Glu Leu Val Glu Ile Arg
                355                 360                 365

Lys Leu Arg Gln Asp Ile Leu Leu Met Lys Pro Tyr Phe Ile Thr Cys
370                 375                 380

Arg Glu Ala Met Glu Ala Arg Leu Leu Leu Gln Leu Gln Asp Arg Gln
385                 390                 395                 400

His Phe Val Glu Asn Asp Glu Met Tyr Ser Val Gln Asp Leu Leu Asp
                405                 410                 415

Val His Ala Gly Arg Leu Gly Cys Ser Leu Thr Glu Ile His Thr Leu
                420                 425                 430

Phe Ala Lys His Ile Lys Leu Asp Cys Glu Arg Cys Gln Ala Lys Gly
                435                 440                 445

Phe Val Cys Glu Leu Cys Arg Glu Gly Asp Val Leu Phe Pro Phe Asp
                450                 455                 460

Ser His Thr Ser Val Cys Ala Asp Cys Ser Ala Val Phe His Arg Asp
465                 470                 475                 480
```

Cys Tyr Tyr Asp Asn Ser Thr Thr Cys Pro Lys Cys Ala Arg Leu Ser
            485                 490                 495

Leu Arg Lys Gln Ser Leu Phe Gln Glu Pro Gly Pro Asp Val Glu Ala
        500                 505                 510

<210> SEQ ID NO 8
<211> LENGTH: 1539
<212> TYPE: DNA
<213> ORGANISM: Homo sapiens

<400> SEQUENCE: 8

| | | | | | |
|---|---|---|---|---|---|
| gaatggccat | cctgtccctg | cgagcccctg | ggcctggca | ggcgatgcag | gtatgggcag | 60 |
| acaggacgct | gttgactccg | cacaccggcg | tgacttctca | ggttctcggg | gtggcagctg | 120 |
| cagtgatgac | accgcttcct | ggtggtcacg | ccgcgggcag | gacgcgggag | gccaggtggg | 180 |
| atgctatgga | atatgatgag | aagctggccc | gtttccggca | ggcccacctc | aaccccttca | 240 |
| acaagcagtc | tgggccgaga | cagcatgagc | agggccctgg | ggaggaggtc | ccggacgtca | 300 |
| ctcctgaaga | ggccctgcct | gagctgcccc | ctggggagcc | ggaattccgc | tgccctgaac | 360 |
| gcgtgatgga | tctcggcctg | tctgaggacc | acttctcccg | ccctgtgggt | ctgttcctgg | 420 |
| cctctgacgt | ccagcagctg | cggcaggcga | tcgaggagtg | caagcaggtg | attctggagc | 480 |
| tgcccgagca | gtcggagaag | cagaaggatg | ccgtggtgcg | actcatccac | ctccggctga | 540 |
| agctccagga | gctgaaggac | cccaatgagg | atgagccaaa | catccgagtg | ctccttgagc | 600 |
| accgcttttta | caaggagaag | agcaagagcg | tcaagcagac | ctgtgacaag | tgtaacacca | 660 |
| tcatctgggg | gctcattcag | acctggtaca | cctgcacagg | gtgttattac | cgctgtcaca | 720 |
| gtaagtgctt | gaacctcatc | tccaagccct | gtgtgagctc | caaagtcagc | caccaagctg | 780 |
| aatacgaact | gaacatctgc | cctgagacag | ggctggacag | ccaggattac | cgctgtgccg | 840 |
| agtgccgggc | gcccatctct | ctgcggggtg | tgcccagtga | ggccaggcag | tgcgactaca | 900 |
| ccggccagta | ctactgcagc | cactgccact | ggaacgacct | ggctgtgatc | cctgcacgcg | 960 |
| ttgtacacaa | ctgggacttt | gagcctcgaa | aggtttctcg | ctgcagcatg | cgctacctgg | 1020 |
| cgctgatggt | gtctcggccc | gtactcaggc | tccgggagat | caacccctctg | ctgttcagct | 1080 |
| acgtggagga | gctggtggag | attcgcaagc | tgcgccagga | catcctgctc | atgaagccgt | 1140 |
| acttcatcac | ctgcagggag | gccatggagg | ctcgtctgct | gctgcagctc | caggatcggc | 1200 |
| agcattttgt | ggagaacgac | gagatgtact | ctgtccagga | cctcctggac | gtgcatgccg | 1260 |
| gccgcctggg | ctgctcgctc | accgagatcc | acacgctctt | cgccaagcac | atcaagctgg | 1320 |
| actgcgagcg | gtgccaggcc | aagggcttcg | tgtgtgagct | ctgcagagag | ggcgacgtgc | 1380 |
| tgttcccgtt | cgacagccac | acgtctgtgt | gcgccgactg | ctccgcggtc | ttccacaggg | 1440 |
| actgctacta | cgacaactcc | accacttgtc | ccaagtgtgc | ccggctcagc | ctgaggaagc | 1500 |
| agtcgctctt | ccaggagcca | ggtcccgatg | tggaggcct | | | 1539 |

<210> SEQ ID NO 9
<211> LENGTH: 1614
<212> TYPE: PRT
<213> ORGANISM: Homo sapiens

<400> SEQUENCE: 9

Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro

```
                  20                  25                  30
Gly Pro Ser Pro Gly Ser Ala His Ser Met Met Gly Pro Ser Pro Gly
             35                  40                  45

Pro Pro Ser Ala Gly His Pro Ile Pro Thr Gln Gly Pro Gly Gly Tyr
 50                  55                  60

Pro Gln Asp Asn Met His Gln Met His Lys Pro Met Glu Ser Met His
 65                  70                  75                  80

Glu Lys Gly Met Ser Asp Pro Arg Tyr Asn Gln Met Lys Gly Met
                 85                  90                  95

Gly Met Arg Ser Gly Gly His Ala Gly Met Gly Pro Pro Ser Pro
                100                 105                 110

Met Asp Gln His Ser Gln Gly Tyr Pro Ser Pro Leu Gly Gly Ser Glu
            115                 120                 125

His Ala Ser Ser Pro Val Pro Ala Ser Gly Pro Ser Ser Gly Pro Gln
            130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
            195                 200                 205

Pro Met Pro Gly Met Gln Gln Gln Met Pro Thr Leu Pro Pro Pro Ser
210                 215                 220

Val Ser Ala Thr Gly Pro Gly Pro Gly Pro Gly Pro Gly Pro Gly Pro
225                 230                 235                 240

Gly Pro Gly Pro Ala Pro Pro Asn Tyr Ser Arg Pro His Gly Met Gly
                245                 250                 255

Gly Pro Asn Met Pro Pro Pro Gly Pro Ser Gly Val Pro Pro Gly Met
                260                 265                 270

Pro Gly Gln Pro Pro Gly Gly Pro Pro Lys Pro Trp Pro Glu Gly Pro
            275                 280                 285

Met Ala Asn Ala Ala Ala Pro Thr Ser Thr Pro Gln Lys Leu Ile Pro
            290                 295                 300

Pro Gln Pro Thr Gly Arg Pro Ser Pro Ala Pro Pro Ala Val Pro Pro
305                 310                 315                 320

Ala Ala Ser Pro Val Met Pro Pro Gln Thr Gln Ser Pro Gly Gln Pro
                325                 330                 335

Ala Gln Pro Ala Pro Met Val Pro Leu His Gln Lys Gln Ser Arg Ile
            340                 345                 350

Thr Pro Ile Gln Lys Pro Arg Gly Leu Asp Pro Val Glu Ile Leu Gln
            355                 360                 365

Glu Arg Glu Tyr Arg Leu Gln Ala Arg Ile Ala His Arg Ile Gln Glu
            370                 375                 380

Leu Glu Asn Leu Pro Gly Ser Leu Ala Gly Asp Leu Arg Thr Lys Ala
385                 390                 395                 400

Thr Ile Glu Leu Lys Ala Leu Arg Leu Leu Asn Phe Gln Arg Gln Leu
                405                 410                 415

Arg Gln Glu Val Val Val Cys Met Arg Arg Asp Thr Ala Leu Glu Thr
            420                 425                 430

Ala Leu Asn Ala Lys Ala Tyr Lys Arg Ser Lys Arg Gln Ser Leu Arg
            435                 440                 445
```

```
Glu Ala Arg Ile Thr Glu Lys Leu Glu Lys Gln Gln Lys Ile Glu Gln
        450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                    485                 490                 495
Ile Gln Lys Leu Thr Lys Ala Val Ala Thr Tyr His Ala Asn Thr Glu
                500                 505                 510
Arg Glu Gln Lys Lys Glu Asn Glu Arg Ile Glu Lys Glu Arg Met Arg
            515                 520                 525
Arg Leu Met Ala Glu Asp Glu Glu Gly Tyr Arg Lys Leu Ile Asp Gln
        530                 535                 540
Lys Lys Asp Lys Arg Leu Ala Tyr Leu Leu Gln Gln Thr Asp Glu Tyr
545                 550                 555                 560
Val Ala Asn Leu Thr Glu Leu Val Arg Gln His Lys Ala Ala Gln Val
                565                 570                 575
Ala Lys Glu Lys Lys Lys Lys Lys Lys Lys Lys Ala Glu Asn Ala
                580                 585                 590
Glu Gly Gln Thr Pro Ala Ile Gly Pro Asp Gly Glu Pro Leu Asp Glu
            595                 600                 605
Thr Ser Gln Met Ser Asp Leu Pro Val Lys Val Ile His Val Glu Ser
        610                 615                 620
Gly Lys Ile Leu Thr Gly Thr Asp Ala Pro Lys Ala Gly Gln Leu Glu
625                 630                 635                 640
Ala Trp Leu Glu Met Asn Pro Gly Tyr Glu Val Ala Pro Arg Ser Asp
                645                 650                 655
Ser Glu Glu Ser Gly Ser Glu Glu Glu Glu Glu Glu Glu Glu Glu Glu
            660                 665                 670
Gln Pro Gln Ala Ala Gln Pro Thr Leu Pro Val Glu Glu Lys Lys
        675                 680                 685
Lys Ile Pro Asp Pro Asp Ser Asp Asp Val Ser Glu Val Asp Ala Arg
        690                 695                 700
His Ile Ile Glu Asn Ala Lys Gln Asp Val Asp Asp Glu Tyr Gly Val
705                 710                 715                 720
Ser Gln Ala Leu Ala Arg Gly Leu Gln Ser Tyr Tyr Ala Val Ala His
                725                 730                 735
Ala Val Thr Glu Arg Val Asp Lys Gln Ser Ala Leu Met Val Asn Gly
                740                 745                 750
Val Leu Lys Gln Tyr Gln Ile Lys Gly Leu Glu Trp Leu Val Ser Leu
        755                 760                 765
Tyr Asn Asn Asn Leu Asn Gly Ile Leu Ala Asp Glu Met Gly Leu Gly
        770                 775                 780
Lys Thr Ile Gln Thr Ile Ala Leu Ile Thr Tyr Leu Met Glu His Lys
785                 790                 795                 800
Arg Ile Asn Gly Pro Phe Leu Ile Ile Val Pro Leu Ser Thr Leu Ser
                805                 810                 815
Asn Trp Ala Tyr Glu Phe Asp Lys Trp Ala Pro Ser Val Val Lys Val
                820                 825                 830
Ser Tyr Lys Gly Ser Pro Ala Ala Arg Arg Ala Phe Val Pro Gln Leu
        835                 840                 845
Arg Ser Gly Lys Phe Asn Val Leu Leu Thr Thr Tyr Glu Tyr Ile Ile
850                 855                 860
```

```
Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
            885                 890                 895

Leu Asn Thr His Tyr Val Ala Pro Arg Leu Leu Leu Thr Gly Thr
        900                 905                 910

Pro Leu Gln Asn Lys Leu Pro Glu Leu Trp Ala Leu Leu Asn Phe Leu
    915                 920                 925

Leu Pro Thr Ile Phe Lys Ser Cys Ser Thr Phe Glu Gln Trp Phe Asn
    930                 935                 940

Ala Pro Phe Ala Met Thr Gly Glu Lys Val Asp Leu Asn Glu Glu Glu
945                 950                 955                 960

Thr Ile Leu Ile Ile Arg Arg Leu His Lys Val Leu Arg Pro Phe Leu
                965                 970                 975

Leu Arg Arg Leu Lys Lys Glu Val Glu Ala Gln Leu Pro Glu Lys Val
            980                 985                 990

Glu Tyr Val Ile Lys Cys Asp Met Ser Ala Leu Gln Arg Val Leu Tyr
        995                 1000                1005

Arg His Met Gln Ala Lys Gly Val Leu Leu Thr Asp Gly Ser Glu Lys
    1010                1015                1020

Asp Lys Lys Gly Lys Gly Gly Thr Lys Thr Leu Met Asn Thr Ile Met
1025                1030                1035                1040

Gln Leu Arg Lys Ile Cys Asn His Pro Tyr Met Phe Gln His Ile Glu
                1045                1050                1055

Glu Ser Phe Ser Glu His Leu Gly Phe Thr Gly Gly Ile Val Gln Gly
            1060                1065                1070

Leu Asp Leu Tyr Arg Ala Ser Gly Lys Phe Glu Leu Leu Asp Arg Ile
        1075                1080                1085

Leu Pro Lys Leu Arg Ala Thr Asn His Lys Val Leu Leu Phe Cys Gln
    1090                1095                1100

Met Thr Ser Leu Met Thr Ile Met Glu Asp Tyr Phe Ala Tyr Arg Gly
1105                1110                1115                1120

Phe Lys Tyr Leu Arg Leu Asp Gly Thr Thr Lys Ala Glu Asp Arg Gly
                1125                1130                1135

Met Leu Leu Lys Thr Phe Asn Glu Pro Gly Ser Glu Tyr Phe Ile Phe
            1140                1145                1150

Leu Leu Ser Thr Arg Ala Gly Gly Leu Gly Leu Asn Leu Gln Ser Ala
        1155                1160                1165

Asp Thr Val Ile Ile Phe Asp Ser Asp Trp Asn Pro His Gln Asp Leu
    1170                1175                1180

Gln Ala Gln Asp Arg Ala His Arg Ile Gly Gln Gln Asn Glu Val Arg
1185                1190                1195                1200

Val Leu Arg Leu Cys Thr Val Asn Ser Val Glu Glu Lys Ile Leu Ala
                1205                1210                1215

Ala Ala Lys Tyr Lys Leu Asn Val Asp Gln Lys Val Ile Gln Ala Gly
            1220                1225                1230

Met Phe Asp Gln Lys Ser Ser His Glu Arg Arg Ala Phe Leu Gln
        1235                1240                1245

Ala Ile Leu Glu His Glu Glu Gln Asp Glu Glu Asp Glu Val Pro
    1250                1255                1260

Asp Asp Glu Thr Val Asn Gln Met Ile Ala Arg His Glu Glu Glu Phe
1265                1270                1275                1280

Asp Leu Phe Met Arg Met Asp Leu Asp Arg Arg Arg Glu Glu Ala Arg
```

Asn Pro Lys Arg Lys Pro Arg Leu Met Glu Glu Asp Glu Leu Pro Ser
            1285                1290                1295
                1300                1305                1310

Trp Ile Ile Lys Asp Asp Ala Glu Val Glu Arg Leu Thr Cys Glu Glu
        1315                1320                1325

Glu Glu Glu Lys Met Phe Gly Arg Gly Ser Arg His Arg Lys Glu Val
    1330                1335                1340

Asp Tyr Ser Asp Ser Leu Thr Glu Lys Gln Trp Leu Lys Ala Ile Glu
1345                1350                1355                1360

Glu Gly Thr Leu Glu Glu Ile Glu Glu Glu Val Arg Gln Lys Lys Ser
            1365                1370                1375

Ser Arg Lys Arg Lys Arg Asp Ser Asp Ala Gly Ser Ser Thr Pro Thr
        1380                1385                1390

Thr Ser Thr Arg Ser Arg Asp Lys Asp Asp Glu Ser Lys Lys Gln Lys
    1395                1400                1405

Lys Arg Gly Arg Pro Pro Ala Glu Lys Leu Ser Pro Asn Pro Pro Asn
1410                1415                1420

Leu Thr Lys Lys Met Lys Lys Ile Val Asp Ala Val Ile Lys Tyr Lys
1425            1430                1435                1440

Asp Ser Ser Ser Gly Arg Gln Leu Ser Glu Val Phe Ile Gln Leu Pro
        1445                1450                1455

Ser Arg Lys Glu Leu Pro Glu Tyr Tyr Glu Leu Ile Arg Lys Pro Val
    1460                1465                1470

Asp Phe Lys Lys Ile Lys Glu Arg Ile Arg Asn His Lys Tyr Arg Ser
1475                1480                1485

Leu Asn Asp Leu Glu Lys Asp Val Met Leu Leu Cys Gln Asn Ala Gln
    1490                1495                1500

Thr Phe Asn Leu Glu Gly Ser Leu Ile Tyr Glu Asp Ser Ile Val Leu
1505                1510                1515                1520

Gln Ser Val Phe Thr Ser Val Arg Gln Lys Ile Glu Lys Glu Asp Asp
        1525                1530                1535

Ser Glu Gly Glu Glu Ser Glu Glu Glu Glu Gly Glu Glu Glu Gly
    1540                1545                1550

Ser Glu Ser Glu Ser Arg Ser Val Lys Val Lys Ile Lys Leu Gly Arg
    1555                1560                1565

Lys Glu Lys Ala Gln Asp Arg Leu Lys Gly Gly Arg Arg Arg Pro Ser
    1570                1575                1580

Arg Gly Ser Arg Ala Lys Pro Val Val Ser Asp Asp Asp Ser Glu Glu
1585                1590                1595                1600

Glu Gln Glu Glu Asp Arg Ser Gly Ser Gly Ser Glu Glu Asp
    1605                1610

<210> SEQ ID NO 10
<211> LENGTH: 4845
<212> TYPE: DNA
<213> ORGANISM: Homo sapiens

<400> SEQUENCE: 10
atgtccactc cagacccacc cctgggcgga actcctcggc caggtccttc cccgggccct      60
ggcccttccc ctggagccat gctgggccct agcccgggtc cctcgccggg ctccgcccac     120
agcatgatgg ggcccagccc agggccgccc tcagcaggac accccatccc cacccagggg     180
cctggagggt accctcagga caacatgcac cagatgcaca gcccatggga gtccatgcat     240
gagaagggca tgtcggacga cccgcgctac aaccagatga aggaatggga tgcgcggtca     300

```
ggggggccatg ctgggatggg gcccccgccc agccccatgg accagcactc ccaaggttac    360
ccctcgcccc tgggtggctc tgagcatgcc tctagtccag ttccagccag tggcccgtct    420
tcggggcccc agatgtcttc cgggccagga ggtgccccgc tggatggtgc tgaccccag     480 gccttggggc agcagaaccg ggcccaacc ccatttaacc agaaccagct gcaccagctc     540
agagctcaga tcatggccta caagatgctg gccaggggc agcccctccc cgaccacctg     600
cagatggcgg tgcagggcaa gcggccgatg cccgggatgc agcagcagat gccaacgcta    660
cctccaccct cggtgtccgc aacaggaccc ggccctggcc ctggccctgg cccggcccg    720 ggtcccggcc cggcacctcc aaattacagc aggcctcatg gtatgggagg gcccaacatg    780
cctcccccag accctcggg cgtgccccc gggatgccag gccagcctcc tggagggcct     840
cccaagccct ggcctgaagg acccatggcg aatgctgctg cccccacgag cacccctcag    900
aagctgattc ccccgcagcc aacgggccgc ccttccccg cgcccctgc cgtcccaccc     960 gccgcctcgc ccgtgatgcc accgcagacc cagtccccg ggcagccggc ccagcccgcg    1020
cccatggtgc cactgcacca gaagcagagc cgcatcaccc ccatccagaa gccgcgggc    1080 ctcgaccctg tggagatcct gcaggagcgc gagtacaggc tgcaggctcg catcgcacac    1140
cgaattcagg aacttgaaaa ccttcccggg tccctggccg gggatttgcg aaccaaagcg    1200
accattgagc tcaaggccct caggctgctg aacttccaga ggcagctgcg ccaggaggtg    1260
gtggtgtgca tgcggaggga cacagcgctg gagacagccc tcaatgctaa ggcctacaag    1320
cgcagcaagc gccagtccct gcgcgaggcc cgcatcactg agaagctgga gaagcagcag    1380
aagatcgagc aggagcgcaa gcgccggcag aagcaccagg aatacctcaa tagcattctc    1440
cagcatgcca aggatttcaa ggaatatcac agatccgtca caggcaaaat ccagaagctg    1500
accaaggcag tggccacgta ccatgccaac acggagcggg agcagaagaa agagaacgag    1560
cggatcgaga aggagcgcat gcggaggctc atggctgaag atgaggaggg gtaccgcaag    1620
ctcatcgacc agaagaagga caagcgcctg gcctacctct tgcagcagac agacgagtac    1680
gtggctaacc tcacggagct ggtgcggcag cacaaggctg cccaggtcgc caaggagaaa    1740
aagaagaaaa agaaaaagaa gaaggcagaa aatgcagaag gacagacgcc tgccattggg    1800
ccggatggcg agcctctgga cgagaccagc cagatgagcg acctcccggt gaaggtgatc    1860
cacgtggaga gtgggaagat cctcacaggc acagatgccc ccaaagccgg gcagctggag    1920
gcctggctcg agatgaaccc ggggtatgaa gtagctccga ggtctgatag tgaagaaagt    1980
ggctcagaag aagaggaaga ggaggaggag gaagagcagc cgcaggcagc acagcctccc    2040
accctgcccg tggaggagaa gaagaagatt ccagatccag acagcgatga cgtctctgag    2100
gtggacgcgc ggcacatcat tgagaatgcc aagcaagatg tcgatgatga atatggcgtg    2160
tcccaggccc ttgcacgtgg cctgcagtcc tactatgccg tggcccatgc tgtcactgag    2220
agagtggaca gcagtcagc gcttatggtc aatggtgtcc tcaaacagta ccagatcaaa    2280
ggtttggagt ggctggtgtc cctgtacaac aacaacctga acggcatcct ggccgacgag    2340
atgggcctgg ggaagaccat ccagaccatc gcgctcatca cgtacctcat ggagcacaaa    2400
cgcatcaatg ggccttcct catcatcgtg cctctctcaa cgctgtccaa ctgggcgtac    2460
gagtttgaca gtgggccccc ctccgtggtg aaggtgtctt acaagggatc cccagcagca    2520
agacgggcct ttgtccccca gctccggagt gggaagttca acgtcttgct gacgacgtac    2580
gagtacatca tcaaagacaa gcacatcctc gccaagatcc gttggaagta catgattgtg    2640
```

```
gacgaaggtc accgcatgaa gaaccaccac tgcaagctga cgcaggtgct caacacgcac      2700
tatgtggcac cccgccgcct gctgctgacg ggcacaccgc tgcagaacaa gcttcccgag      2760
ctctgggcgc tgctcaactt cctgctgccc accatcttca agagctgcag caccttcgag      2820
cagtggttta acgcaccctt tgccatgacc ggggaaaagg tggacctgaa tgaggaggaa      2880
accattctca tcatccggcg tctccacaaa gtgctgcggc ccttcttgct ccgacgactc      2940
aagaaggaag tcgaggccca gttgcccgaa aaggtggagt acgtcatcaa gtgcgacatg      3000
tctgcgctgc agcgagtgct ctaccgccac atgcaggcca agggcgtgct gctgactgat      3060
ggctccgaga aggacaagaa gggcaaaggc ggcaccaaga ccctgatgaa caccatcatg      3120
cagctgcgga agatctgcaa ccaccnctac atgttccagc acatcgagga gtccttttcc      3180
gagcacttgg ggttcactgg cggcattgtc aagggctgg acctgtaccg agcctcgggt      3240
aaatttgagc ttcttgatag aattcttccc aaactccgag caaccaacca caaagtgctg      3300
ctgttctgcc aaatgacctc cctcatgacc atcatggaag attactttgc gtatcgcggc      3360
tttaaatacc tcaggcttga tggaaccacg aaggcggagg accggggcat gctgctgaaa      3420
accttcaacg agcccggctc tgagtacttc atcttcctgc tcagcacccg ggctgggggg      3480
ctcggcctga acctccagtc ggcagacact gtgatcattt ttgacagcga ctggaatcct      3540
caccaggacc tgcaagcgca ggaccgagcc caccgcatcg ggcagcagaa cgaggtgcgt      3600
gtgctccgcc tctgcaccgt caacagcgtg gaggagaaga tcctagctgc agccaagtac      3660
aagctcaacg tggaccagaa ggtgatccag gccggcatgt tcgaccagaa gtcctccagc      3720
catgagcggc gcgccttcct gcaggccatc ctggagcacg aggagcagga tgaggaggaa      3780
gacgaggtgc ccgacgacga gaccgtcaac cagatgatcg cccggcacga ggaggagttt      3840
gatctgttca tgcgcatgga cctggaccgc aggcgcgagg aggcccgcaa ccccaagcgg      3900
aagccgcgcc tcatggagga ggacgagctc ccctcgtgga tcatcaagga cgacgcggag      3960
gtggagcggc tgacctgtga ggaggaggag gagaagatgt tcggccgtgg ctcccgccac      4020
cgcaaggagg tggactacag cgactcactg acggagaagc agtggctcaa ggccatcgag      4080
gagggcacgc tggaggagat cgaagaggag gtccggcaga gaaatcatc acggaagcgc      4140 aagcgagaca gcgacgccgg ctcctccacc ccgaccacca gcacccgcag ccgcgacaag      4200
gacgacgaga gcaagaagca gaagaagcgc gggcggccgc ctgccgagaa actctcccct      4260
aacccaccca acctcaccaa gaagatgaag aagattgtgg atgccgtgat caagtacaag      4320
gacagcagca gtggacgtca gctcagcgag gtcttcatcc agctgccctc gcgaaaggag      4380
ctgcccgagt actacgagct catccgcaag cccgtggact tcaagaagat aaaggagcgc      4440
attcgcaacc acaagtaccg cagcctcaac gacctagaga aggacgtcat gctcctgtgc      4500
cagaacgcac agaccttcaa cctggagggc tccctgatct atgaagactc catcgtcttg      4560
cagtcggtct tcaccagcgt gcggcagaaa atcgagaagg aggatgacag tgaaggcgag      4620
gagagtgagg aggaggaaga gggcgaggag gaaggctccg aatccgaatc tcggtccgtc      4680
aaagtgaaga tcaagcttgg ccggaaggag aaggcacagg accggctgaa gggcggccgg      4740
cggcggccga gccgagggtc ccgagccaag ccggtcgtga gtgacgatga cagtgaggag      4800
gaacaagagg aggaccgctc aggaagtggc agcgaagaag actga                      4845
```

<210> SEQ ID NO 11
<211> LENGTH: 454
<212> TYPE: PRT
<213> ORGANISM: Homo sapiens

<400> SEQUENCE: 11

```
Met Ser Ala Gly Gly Pro Cys Pro Ala Ala Gly Gly Pro Gly
1               5                   10                  15
Gly Ala Ser Cys Ser Val Gly Ala Pro Gly Gly Val Ser Met Phe Arg
                20                  25                  30
Trp Leu Glu Val Leu Glu Lys Glu Phe Asp Lys Ala Phe Val Asp Val
            35                  40                  45
Asp Leu Leu Gly Glu Ile Asp Pro Asp Gln Ala Asp Ile Thr Tyr
        50                  55                  60
Glu Gly Arg Gln Lys Met Thr Ser Leu Ser Ser Cys Phe Ala Gln Leu
65                  70                  75                  80
Cys His Lys Ala Gln Ser Val Ser Gln Ile Asn His Lys Leu Glu Ala
                85                  90                  95
Gln Leu Val Asp Leu Lys Ser Glu Leu Thr Glu Thr Gln Ala Glu Lys
                100                 105                 110
Val Val Leu Glu Lys Glu Val His Asp Gln Leu Leu Gln Leu His Ser
            115                 120                 125
Ile Gln Leu Gln Leu His Ala Lys Thr Gly Gln Ser Ala Asp Ser Gly
        130                 135                 140
Thr Ile Lys Ala Lys Leu Glu Arg Glu Leu Glu Ala Asn Lys Lys Glu
145                 150                 155                 160
Lys Met Lys Glu Ala Gln Leu Glu Ala Glu Val Lys Leu Leu Arg Lys
                165                 170                 175
Glu Asn Glu Ala Leu Arg Arg His Ile Ala Val Leu Gln Ala Glu Val
                180                 185                 190
Tyr Gly Ala Arg Leu Ala Ala Lys Tyr Leu Asp Lys Glu Leu Ala Gly
            195                 200                 205
Arg Val Gln Gln Ile Gln Leu Leu Gly Arg Asp Met Lys Gly Pro Ala
        210                 215                 220
His Asp Lys Leu Trp Asn Gln Leu Glu Ala Glu Ile His Leu His Arg
225                 230                 235                 240
His Lys Thr Val Ile Arg Ala Cys Arg Gly Arg Asn Asp Leu Lys Arg
                245                 250                 255
Pro Met Gln Ala Pro Pro Gly His Asp Gln Asp Ser Leu Lys Lys Ser
                260                 265                 270
Gln Gly Val Gly Pro Ile Arg Lys Val Leu Leu Lys Glu Asp His
            275                 280                 285
Glu Gly Leu Gly Ile Ser Ile Thr Gly Gly Lys Glu His Gly Val Pro
        290                 295                 300
Ile Leu Ile Ser Glu Ile His Pro Gly Gln Pro Ala Asp Arg Cys Gly
305                 310                 315                 320
Gly Leu His Val Gly Asp Ala Ile Leu Ala Val Asn Gly Val Asn Leu
                325                 330                 335
Arg Asp Thr Lys His Lys Glu Ala Val Thr Ile Leu Ser Gln Gln Arg
                340                 345                 350
Gly Glu Ile Glu Phe Glu Val Val Tyr Val Ala Pro Glu Val Asp Ser
            355                 360                 365
Asp Asp Glu Asn Val Glu Tyr Glu Asp Glu Ser Gly His Arg Tyr Arg
        370                 375                 380
Leu Tyr Leu Asp Glu Leu Glu Gly Gly Asn Pro Gly Ala Ser Cys
385                 390                 395                 400
Lys Asp Thr Ser Gly Glu Ile Lys Val Leu Gln Gly Phe Asn Lys Lys
```

```
                    405                 410                 415
Ala Val Thr Asp Thr His Glu Asn Gly Asp Leu Gly Thr Ala Ser Glu
            420                 425                 430

Thr Pro Leu Asp Asp Gly Ala Ser Lys Leu Asp Asp Leu His Thr Leu
        435                 440                 445

Tyr His Lys Lys Ser Tyr
        450

<210> SEQ ID NO 12
<211> LENGTH: 1365
<212> TYPE: DNA
<213> ORGANISM: Homo sapiens

<400> SEQUENCE: 12
```

| | | | | | |
|---|---|---|---|---|---|
| ccatgtcggc | gggcggtcca | tgcccagcag | cagccggagg | gggcccaggg | ggcgcctcct | 60 |
| gctccgtggg | ggcccctggc | ggggtatcca | tgttccggtg | gctggaggtg | ctggagaagg | 120 |
| agttcgacaa | agcttttgtg | gatgtggatc | tgctcctggg | agagatcgat | ccagaccaag | 180 |
| cggacatcac | ttatgagggg | cgacagaaga | tgaccagcct | gagctcctgc | tttgcacagc | 240 |
| tttgccacaa | agcccagtct | gtgtctcaaa | tcaaccacaa | gctggaggca | cagttggtgg | 300 |
| atctgaaatc | tgaactgaca | gaaacccaag | cagagaaagt | tgttttggag | aaagaagtac | 360 |
| atgatcagct | tttacagctg | cactctattc | agctgcagct | tcatgctaaa | actggtcaaa | 420 |
| gtgctgactc | tggtaccatt | aaggcaaaat | tggaaagaga | gcttgaggca | aacaaaaaag | 480 |
| aaaaaatgaa | agaagcacaa | cttgaagctg | aagtgaaatt | gttgagaaaa | gagaatgaag | 540 |
| cccttcgtag | acatatagct | gttctccagg | ctgaagtata | tggggcgaga | ctagctgcca | 600 |
| agtacttgga | taaggaactg | gcaggaaggg | tccaacagat | acaattgcta | ggacgagata | 660 |
| tgaagggacc | tgctcatgat | aagctttgga | accaattaga | agctgaaata | catttgcatc | 720 |
| gtcacaaaac | tgtgatccga | gcctgcagag | gacgtaatga | cttgaaacga | ccaatgcaag | 780 |
| caccaccagg | ccatgatcaa | gattccctaa | agaaaagcca | aggtgttggt | ccaattagaa | 840 |
| aagttctcct | ccttaaggaa | gatcatgaag | gccttggcat | ttcaattaca | ggtgggaaag | 900 |
| aacatggtgt | tccaatcctc | atctctgaga | tccatccggg | gcaacctgct | gatagatgcg | 960 |
| gagggctgca | cgttggggat | gctattttgg | cagtcaacgg | agttaaccta | agggacacaa | 1020 |
| agcataaaga | agctgtaact | attctttctc | agcagagagg | agagattgaa | tttgaagtag | 1080 |
| tttatgtggc | tcctgaagtg | gattctgatg | atgaaaacgt | agagtatgaa | gatgagagtg | 1140 |
| gacatcgtta | ccgtttgtac | cttgatgagt | tagaaggagg | tggtaaccct | ggtgctagtt | 1200 |
| gcaaagacac | aagtggggaa | atcaaagtat | tacaaggatt | taataagaag | gcagtaactg | 1260 |
| acacacatga | aaatggagac | ctgggcactg | caagtgaaac | tccgctagat | gacggtgctt | 1320 |
| caaaattaga | tgatctgcac | actctgtatc | ataaaaaatc | ttatt | | 1365 |

```
<210> SEQ ID NO 13
<211> LENGTH: 2517
<212> TYPE: PRT
<213> ORGANISM: Homo sapiens

<400> SEQUENCE: 13

Met Val Gly Glu Arg His Ala Gly Asp Leu Met Val Pro Leu Gly Pro
1               5                   10                  15

Arg Leu Gln Ala Tyr Pro Glu Glu Leu Ile Arg Gln Arg Pro Gly His
                20                  25                  30
```

```
Asp Gly His Pro Glu Tyr Leu Ile Arg Trp Ser Val Leu Lys Cys Gly
         35                  40                  45

Glu Val Gly Lys Val Gly Val Glu Glu Gly Lys Ala Glu His Ile Leu
 50                  55                  60

Met Trp Leu Ser Ala Pro Glu Val Tyr Ala Asn Cys Pro Gly Leu Leu
 65              70                  75                      80

Gly Glu Arg Ala Leu Ser Lys Gly Leu Gln His Glu Pro Ala Gly Val
                 85                  90                  95

Ser Gly Ser Phe Pro Arg Asp Pro Gly Gly Leu Asp Glu Val Ala Met
            100                 105                 110

Gly Glu Met Glu Ala Asp Val Gln Ala Leu Val Arg Arg Ala Ala Arg
        115                 120                 125

Gln Leu Ala Glu Ser Gly Thr Pro Ser Leu Thr Ala Ala Val Leu His
    130                 135                 140

Thr Ile His Val Leu Ser Ala Tyr Ala Ser Ile Gly Pro Leu Thr Gly
145                 150                 155                 160

Val Phe Arg Glu Thr Gly Ala Leu Asp Leu Leu Met His Met Leu Cys
                165                 170                 175

Asn Pro Glu Pro Gln Ile Arg Arg Ser Ala Gly Lys Met Leu Gln Ala
            180                 185                 190

Leu Ala Ala His Asp Ala Gly Ser Arg Ala His Val Leu Leu Ser Leu
        195                 200                 205

Ser Gln Gln Asp Gly Ile Glu Gln His Met Asp Phe Asp Ser Arg Tyr
    210                 215                 220

Thr Leu Leu Glu Leu Phe Ala Glu Thr Thr Ser Ser Glu Glu His Cys
225                 230                 235                 240

Met Ala Phe Glu Gly Ile His Leu Pro Gln Ile Pro Gly Lys Leu Leu
                245                 250                 255

Phe Ser Leu Val Lys Arg Tyr Leu Cys Val Thr Ser Leu Leu Asp Gln
            260                 265                 270

Leu Asn Ser Ser Pro Glu Leu Gly Ala Gly Asp Gln Ser Ser Pro Cys
        275                 280                 285

Ala Thr Arg Glu Lys Ser Arg Gly Gln Arg Glu Leu Glu Phe Ser Met
290                 295                 300

Ala Val Gly Asn Leu Ile Ser Glu Leu Val Arg Ser Met Gly Trp Ala
305                 310                 315                 320

Arg Asn Leu Ser Glu Gln Gly Met Ser Pro Pro Arg Pro Thr Arg Ser
                325                 330                 335

Ile Phe Gln Pro Tyr Ile Ser Gly Pro Ser Leu Leu Leu Pro Thr Ile
            340                 345                 350

Val Thr Thr Pro Arg Arg Gln Gly Trp Val Phe Arg Gln Arg Ser Glu
        355                 360                 365

Phe Ser Ser Arg Ser Gly Tyr Gly Glu Tyr Val Gln Gln Thr Leu Gln
    370                 375                 380

Pro Gly Met Arg Val Arg Met Leu Asp Asp Tyr Glu Glu Ile Ser Ala
385                 390                 395                 400

Gly Asp Glu Gly Glu Phe Arg Gln Ser Asn Asn Gly Ile Pro Pro Val
                405                 410                 415

Gln Val Phe Trp Gln Ser Thr Gly Arg Thr Tyr Trp Val His Trp His
            420                 425                 430

Met Leu Glu Ile Leu Gly Pro Glu Glu Ala Thr Glu Asp Lys Ala Ser
        435                 440                 445

Ala Ala Val Glu Lys Gly Ala Gly Ala Thr Val Leu Gly Thr Ala Phe
```

```
            450                 455                 460
Pro Ser Trp Asp Trp Asn Pro Met Asp Gly Leu Tyr Pro Leu Pro Tyr
465                 470                 475                 480

Leu Gln Pro Glu Pro Gln Lys Asn Glu Arg Val Gly Tyr Leu Thr Gln
                485                 490                 495

Ala Glu Trp Trp Glu Leu Leu Phe Phe Ile Lys Lys Leu Asp Leu Cys
            500                 505                 510

Glu Gln Gln Pro Ile Phe Gln Asn Leu Trp Lys Asn Leu Asp Glu Thr
            515                 520                 525

Leu Gly Glu Lys Ala Leu Gly Glu Ile Ser Val Ser Val Glu Met Ala
            530                 535                 540

Glu Ser Leu Leu Gln Val Leu Ser Ser Arg Phe Glu Gly Ser Thr Leu
545                 550                 555                 560

Asn Asp Leu Leu Asn Ser Gln Ile Tyr Thr Lys Tyr Gly Leu Leu Ser
                565                 570                 575

Asn Glu Pro Ser Ser Ser Thr Ser Arg Asn His Ser Cys Thr Pro
            580                 585                 590

Asp Pro Glu Glu Ser Lys Ser Glu Ala Ser Phe Ser Glu Glu Glu
            595                 600                 605

Thr Glu Ser Leu Lys Ala Lys Ala Glu Ala Pro Lys Thr Glu Ala Glu
            610                 615                 620

Pro Thr Lys Thr Arg Thr Glu Thr Pro Met Ala Gln Ser Asp Ser Gln
625                 630                 635                 640

Leu Phe Asn Gln Leu Leu Val Thr Glu Gly Met Thr Leu Pro Thr Glu
                645                 650                 655

Met Lys Glu Ala Ala Ser Glu Met Ala Arg Ala Leu Arg Gly Pro Gly
            660                 665                 670

Pro Arg Ser Ser Leu Asp Gln His Val Ala Ala Val Ala Thr Val
            675                 680                 685

Gln Ile Ser Ser Leu Asp Thr Asn Leu Gln Leu Ser Gly Leu Ser Ala
            690                 695                 700

Leu Ser Gln Ala Val Glu Glu Val Thr Glu Arg Asp His Pro Leu Val
705                 710                 715                 720

Arg Pro Asp Arg Ser Leu Arg Glu Lys Leu Val Lys Met Leu Val Glu
                725                 730                 735

Leu Leu Thr Asn Gln Val Gly Glu Lys Met Val Val Gln Ala Leu
                740                 745                 750

Arg Leu Leu Tyr Leu Leu Met Thr Lys His Glu Trp Arg Pro Leu Phe
            755                 760                 765

Ala Arg Glu Gly Gly Ile Tyr Ala Val Leu Val Cys Met Gln Glu Tyr
            770                 775                 780

Lys Thr Ser Val Leu Val Gln Gln Ala Gly Leu Ala Ala Leu Lys Met
785                 790                 795                 800

Leu Ala Val Ala Ser Ser Glu Ile Pro Thr Phe Val Thr Gly Arg
                805                 810                 815

Asp Ser Ile His Ser Leu Phe Asp Ala Gln Met Thr Arg Glu Ile Phe
            820                 825                 830

Ala Ser Ile Asp Ser Ala Thr Arg Pro Gly Ser Glu Ser Leu Leu Leu
            835                 840                 845

Thr Val Pro Ala Ala Val Ile Leu Met Leu Asn Thr Glu Gly Cys Ser
            850                 855                 860

Ser Ala Ala Arg Asn Gly Leu Leu Leu Leu Asn Leu Leu Leu Cys Asn
865                 870                 875                 880
```

```
His His Thr Leu Gly Asp Gln Ile Ile Thr Gln Glu Leu Arg Asp Thr
                885                 890                 895

Leu Phe Arg His Ser Gly Ile Ala Pro Arg Thr Glu Pro Met Pro Thr
            900                 905                 910

Thr Arg Thr Ile Leu Met Met Leu Leu Asn Arg Tyr Ser Glu Pro Pro
        915                 920                 925

Gly Ser Pro Glu Arg Ala Ala Leu Glu Thr Pro Ile Ile Gln Gly Gln
    930                 935                 940

Asp Gly Ser Pro Glu Leu Leu Ile Arg Ser Leu Val Gly Pro Ser
945                 950                 955                 960

Ala Glu Leu Leu Leu Asp Leu Glu Arg Val Leu Cys Arg Glu Gly Ser
                965                 970                 975

Pro Gly Gly Ala Val Arg Pro Leu Leu Lys Arg Leu Gln Gln Glu Thr
            980                 985                 990

Gln Pro Phe Leu Leu Leu Leu Arg Thr Leu Asp Ala Pro Gly Pro Asn
        995                 1000                1005

Lys Thr Leu Leu Leu Ser Val Leu Arg Val Ile Thr Arg Leu Leu Asp
    1010                1015                1020

Phe Pro Glu Ala Met Val Leu Pro Trp His Glu Val Leu Glu Pro Cys
1025                1030                1035                1040

Leu Asn Cys Leu Ser Gly Pro Ser Ser Asp Ser Glu Ile Val Gln Glu
                1045                1050                1055

Leu Thr Cys Phe Leu His Arg Leu Ala Ser Met His Lys Asp Tyr Ala
            1060                1065                1070

Val Val Leu Cys Cys Leu Gly Ala Lys Glu Ile Leu Ser Lys Val Leu
        1075                1080                1085

Asp Lys His Ser Ala Gln Leu Leu Leu Gly Cys Glu Leu Arg Asp Leu
    1090                1095                1100

Val Thr Glu Cys Glu Lys Tyr Ala Gln Leu Tyr Ser Asn Leu Thr Ser
1105                1110                1115                1120

Ser Ile Leu Ala Gly Cys Ile Gln Met Val Leu Gly Gln Ile Glu Asp
                1125                1130                1135

His Arg Arg Thr His Gln Pro Ile Asn Ile Pro Phe Phe Asp Val Phe
            1140                1145                1150

Leu Arg His Leu Cys Gln Gly Ser Ser Val Glu Val Lys Glu Asp Lys
        1155                1160                1165

Cys Trp Glu Lys Val Glu Val Ser Ser Asn Pro His Arg Ala Ser Lys
    1170                1175                1180

Leu Thr Asp His Asn Pro Lys Thr Tyr Trp Glu Ser Asn Gly Ser Thr
1185                1190                1195                1200

Gly Ser His Tyr Ile Thr Leu His Met His Arg Gly Val Leu Val Arg
                1205                1210                1215

Gln Leu Thr Leu Leu Val Ala Ser Glu Asp Ser Ser Tyr Met Pro Ala
            1220                1225                1230

Arg Val Val Val Phe Gly Gly Asp Ser Thr Ser Cys Ile Gly Thr Glu
        1235                1240                1245

Leu Asn Thr Val Asn Val Met Pro Ser Ala Ser Arg Val Ile Leu Leu
    1250                1255                1260

Glu Asn Leu Asn Arg Phe Trp Pro Ile Ile Gln Ile Arg Ile Lys Arg
1265                1270                1275                1280

Cys Gln Gln Gly Gly Ile Asp Thr Arg Val Arg Gly Val Glu Val Leu
                1285                1290                1295
```

```
Gly Pro Lys Pro Thr Phe Trp Pro Leu Phe Arg Glu Gln Leu Cys Arg
            1300                1305                1310

Arg Thr Cys Leu Phe Tyr Thr Ile Arg Ala Gln Ala Trp Ser Arg Asp
        1315                1320                1325

Ile Ala Glu Asp His Arg Arg Leu Leu Gln Leu Cys Pro Arg Leu Asn
            1330                1335                1340

Arg Val Leu Arg His Glu Gln Asn Phe Ala Asp Arg Phe Leu Pro Asp
1345                1350                1355                1360

Asp Glu Ala Ala Gln Ala Leu Gly Lys Thr Cys Trp Glu Ala Leu Val
                1365                1370                1375

Ser Pro Leu Val Gln Asn Ile Thr Ser Pro Asp Ala Glu Gly Val Ser
            1380                1385                1390

Ala Leu Gly Trp Leu Leu Asp Gln Tyr Leu Glu Gln Arg Glu Thr Ser
            1395                1400                1405

Arg Asn Pro Leu Ser Arg Ala Ala Ser Phe Ala Ser Arg Val Arg Arg
        1410                1415                1420

Leu Cys His Leu Leu Val His Val Glu Pro Pro Gly Pro Ser Pro
1425                1430                1435                1440

Glu Pro Ser Thr Arg Pro Phe Ser Lys Asn Ser Lys Gly Arg Asp Arg
                1445                1450                1455

Ser Pro Ala Pro Ser Pro Val Leu Pro Ser Ser Ser Leu Arg Asn Ile
            1460                1465                1470

Thr Gln Cys Trp Leu Ser Val Val Gln Glu Gln Val Ser Arg Phe Leu
        1475                1480                1485

Ala Ala Ala Trp Arg Ala Pro Asp Phe Val Pro Arg Tyr Cys Lys Leu
    1490                1495                1500

Tyr Glu His Leu Gln Arg Ala Gly Ser Glu Leu Phe Gly Pro Arg Ala
1505                1510                1515                1520

Ala Phe Met Leu Ala Leu Arg Ser Gly Phe Ser Gly Ala Leu Leu Gln
            1525                1530                1535

Gln Ser Phe Leu Thr Ala Ala His Met Ser Glu Gln Phe Ala Arg Tyr
        1540                1545                1550

Ile Asp Gln Gln Ile Gln Gly Gly Leu Ile Gly Gly Ala Pro Gly Val
            1555                1560                1565

Glu Met Leu Gly Gln Leu Gln Arg His Leu Glu Pro Ile Met Val Leu
    1570                1575                1580

Ser Gly Leu Glu Leu Ala Thr Thr Phe Glu His Phe Tyr Gln His Tyr
1585                1590                1595                1600

Met Ala Asp Arg Leu Leu Ser Phe Gly Ser Ser Trp Leu Glu Gly Ala
            1605                1610                1615

Val Leu Glu Gln Ile Gly Leu Cys Phe Pro Asn Arg Leu Pro Gln Leu
        1620                1625                1630

Met Leu Gln Ser Leu Ser Thr Ser Glu Glu Leu Gln Arg Gln Phe His
    1635                1640                1645

Leu Phe Gln Leu Gln Arg Leu Asp Lys Leu Phe Leu Glu Gln Glu Asp
1650                1655                1660

Glu Glu Glu Lys Arg Leu Glu Glu Glu Glu Glu Glu Glu Glu Glu
1665                1670                1675                1680

Glu Ala Glu Lys Glu Leu Phe Ile Glu Asp Pro Ser Pro Ala Ile Ser
            1685                1690                1695

Ile Leu Val Leu Ser Pro Arg Cys Trp Pro Val Ser Pro Leu Cys Tyr
        1700                1705                1710

Leu Tyr His Pro Arg Lys Cys Leu Pro Thr Glu Phe Cys Asp Ala Leu
```

-continued

```
            1715                1720                1725

Asp Arg Phe Ser Ser Phe Tyr Ser Gln Ser Gln Asn His Pro Val Leu
            1730                1735            1740

Asp Met Gly Pro His Arg Arg Leu Gln Trp Thr Trp Leu Gly Arg Ala
1745                1750                1755                1760

Glu Leu Gln Phe Gly Lys Gln Ile Leu His Val Ser Thr Val Gln Met
                1765                1770                1775

Trp Leu Leu Leu Lys Phe Asn Gln Thr Glu Glu Val Ser Val Glu Thr
            1780                1785                1790

Leu Leu Lys Asp Ser Asp Leu Ser Pro Glu Leu Leu Gln Ala Leu
            1795                1800                1805

Val Pro Leu Thr Ser Gly Asn Gly Pro Leu Thr Leu His Glu Gly Gln
            1810                1815                1820

Asp Phe Pro His Gly Gly Val Leu Arg Leu His Glu Pro Gly Pro Gln
1825                1830                1835                1840

Arg Ser Gly Glu Ala Leu Trp Leu Ile Pro Pro Gln Ala Tyr Leu Asn
                1845                1850                1855

Val Glu Lys Asp Glu Gly Arg Thr Leu Glu Gln Lys Arg Asn Leu Leu
                1860                1865                1870

Ser Cys Leu Leu Val Arg Ile Leu Lys Ala His Gly Glu Lys Gly Leu
            1875                1880                1885

His Ile Asp Gln Leu Val Cys Leu Val Leu Glu Ala Trp Gln Lys Gly
            1890                1895                1900

Pro Asn Pro Pro Gly Thr Leu Gly His Thr Val Ala Gly Gly Val Ala
1905                1910                1915                1920

Cys Thr Ser Thr Asp Val Leu Ser Cys Ile Leu His Leu Leu Gly Gln
                1925                1930                1935

Gly Tyr Val Lys Arg Arg Asp Asp Arg Pro Gln Ile Leu Met Tyr Ala
            1940                1945                1950

Ala Pro Glu Pro Met Gly Pro Cys Arg Gly Gln Ala Asp Val Pro Phe
            1955                1960                1965

Cys Gly Ser Gln Ser Glu Thr Ser Lys Pro Ser Pro Glu Ala Val Ala
            1970                1975                1980

Thr Leu Ala Ser Leu Gln Leu Pro Ala Gly Arg Thr Met Ser Pro Gln
1985                1990                1995                2000

Glu Val Glu Gly Leu Met Lys Gln Thr Val Arg Gln Val Gln Glu Thr
                2005                2010                2015

Leu Asn Leu Glu Pro Asp Val Ala Gln His Leu Leu Ala His Ser His
            2020                2025                2030

Trp Gly Ala Glu Gln Leu Leu Gln Ser Tyr Ser Glu Asp Pro Glu Pro
            2035                2040                2045

Leu Leu Leu Ala Ala Gly Leu Cys Val His Gln Ala Gln Ala Val Pro
            2050                2055                2060

Val Arg Pro Asp His Cys Pro Val Cys Val Ser Pro Leu Gly Cys Asp
2065                2070                2075                2080

Asp Asp Leu Pro Ser Leu Cys Cys Met His Tyr Cys Cys Lys Ser Cys
            2085                2090                2095

Trp Asn Glu Tyr Leu Thr Thr Arg Ile Glu Gln Asn Leu Val Leu Asn
            2100                2105                2110

Cys Thr Cys Pro Ile Ala Asp Cys Pro Ala Gln Pro Thr Gly Ala Phe
            2115                2120                2125

Ile Arg Ala Ile Val Ser Ser Pro Glu Val Ile Ser Lys Tyr Glu Lys
            2130                2135                2140
```

Ala Leu Leu Arg Gly Tyr Val Glu Ser Cys Ser Asn Leu Thr Trp Cys
2145                2150                2155                2160

Thr Asn Pro Gln Gly Cys Asp Arg Ile Leu Cys Arg Gln Gly Leu Gly
            2165                2170                2175

Cys Gly Thr Thr Cys Ser Lys Cys Gly Trp Ala Ser Cys Phe Asn Cys
        2180                2185                2190

Ser Phe Pro Glu Ala His Tyr Pro Ala Ser Cys Gly His Met Ser Gln
    2195                2200                2205

Trp Val Asp Asp Gly Gly Tyr Tyr Asp Gly Met Ser Val Glu Ala Gln
2210                2215                2220

Ser Lys His Leu Ala Lys Leu Ile Ser Lys Arg Cys Pro Ser Cys Gln
2225                2230                2235                2240

Ala Pro Ile Glu Lys Asn Glu Gly Cys Leu His Met Thr Cys Ala Lys
            2245                2250                2255

Cys Asn His Gly Phe Cys Trp Arg Cys Leu Lys Ser Trp Lys Pro Asn
        2260                2265                2270

His Lys Asp Tyr Tyr Asn Cys Ser Ala Met Val Ser Lys Ala Ala Arg
    2275                2280                2285

Gln Glu Lys Arg Phe Gln Asp Tyr Asn Glu Arg Cys Thr Phe His His
2290                2295                2300

Gln Ala Arg Glu Phe Ala Val Asn Leu Arg Asn Arg Val Ser Ala Ile
2305                2310                2315                2320

His Glu Val Pro Pro Pro Arg Ser Phe Thr Phe Leu Asn Asp Ala Cys
            2325                2330                2335

Gln Gly Leu Glu Gln Ala Arg Lys Val Leu Ala Tyr Ala Cys Val Tyr
        2340                2345                2350

Ser Phe Tyr Ser Gln Asp Ala Glu Tyr Met Asp Val Val Glu Gln Gln
    2355                2360                2365

Thr Glu Asn Leu Glu Leu His Thr Asn Ala Leu Gln Ile Leu Leu Glu
2370                2375                2380

Glu Thr Leu Leu Arg Cys Arg Asp Leu Ala Ser Ser Leu Arg Leu Leu
2385                2390                2395                2400

Arg Ala Asp Cys Leu Ser Thr Gly Met Glu Leu Leu Arg Arg Ile Gln
            2405                2410                2415

Glu Arg Leu Leu Ala Ile Leu Gln His Ser Ala Gln Asp Phe Arg Val
        2420                2425                2430

Gly Leu Gln Ser Pro Ser Val Glu Ala Trp Glu Ala Lys Gly Pro Asn
    2435                2440                2445

Met Pro Gly Ser Gln Pro Gln Ala Ser Ser Gly Pro Glu Ala Glu Glu
2450                2455                2460

Glu Glu Glu Asp Asp Glu Asp Val Pro Glu Trp Gln Gln Asp Glu
2465                2470                2475                2480

Phe Asp Glu Glu Leu Asp Asn Asp Ser Phe Ser Tyr Asp Glu Ser Glu
    2485                2490                2495

Asn Leu Asp Gln Glu Thr Phe Phe Phe Gly Asp Glu Glu Glu Asp Glu
        2500                2505                2510

Asp Glu Ala Tyr Asp
        2515

<210> SEQ ID NO 14
<211> LENGTH: 7554
<212> TYPE: DNA
<213> ORGANISM: Homo sapiens

<400> SEQUENCE: 14

```
atggtggggg aacggcatgc tggggacctc atggtgccct tagggcctcg gctgcaggca      60
tatcctgaag aactcattcg acagaggcct gggcatgacg ggcatcctga atacctgatc     120
cgatggagtg tcctgaagtg tggggaagtg ggcaaagtgg gtgtggaaga aggcaaagca     180
gagcacatcc tcatgtggct gtcggctcct gaggtctacg ccaactgccc tgggctgtta     240
ggtgagcggg cactatctaa gggacttcag cacgaaccag ctggggtttc aggaagcttt     300
cctcgagatc caggaggcct ggatgaagtg gcaatgggag agatggaggc tgatgttcag     360
gcgctggtac gcagggcggc caggcagctg gcagaaagtg ggaccccaag cctcacggcc     420
gctgtgcttc acaccatcca cgtgctcagt gcctacgcca gcatcgggcc cctcactggt     480
gtcttcaggg agacaggagc cctggacctg ctcatgcaca tgttatgcaa tcctgagcct     540
cagatccgcc ggagtgcagg caaaatgctg caggctctgg cagcccacga tgctgggagt     600
cgggctcacg tccttctatc actgagccag caagatggca tcgagcagca catggatttt     660
gacagtcgct atacattgct ggagctgttt gcagaaacca catcctctga agaacactgc     720
atggcctttg agggcattca tctgcctcag atcccaggaa agctgctttt ctccttggtg     780
aagcgctacc tttgtgtcac gtccctcctg gatcagctga atagcagtcc agagctggga     840
gctggagacc aaagctcccc atgtgccaca agagagaaaa gccggggaca gcgggaactg     900
gagttcagca tggctgtggg caacctcatc tctgagcttg tgcggagcat gggctgggcc     960
cggaacctca gcgaacaggg catgtcacct cccggccaa cccggtccat ctttcagccc    1020
tacatttcag gccccagcct tttactcccc accattgtca ccaccccag aagacaaggg    1080
tgggtcttcc gccagcgctc tgaattctcc agccgtagtg gctatggaga atatgtgcag    1140
cagacactcc agccagggat gcgagtgcgg atgctggatg attatgagga gatcagtgct    1200
ggggacgagg gcgagttccg gcagagcaac aacggcattc cccctgtgca ggttttctgg    1260
cagtcgacag gccgcactta ctgggtgcac tggcacatgc tggagatcct gggccctgag    1320
gaagccactg aggataaggc ttcagcagct gtggagaagg gggcaggggc tactgtgttg    1380
ggcacagcat ttccctcctg ggactggaat cctatggatg gctgtacccc tttgccgtac    1440
ctccagcccg aacctcagaa gaatgagaga gtgggatatc tgacccaggc tgaatggtgg    1500
gagctgcttt tctttatcaa aaagttggac ttgtgtgagc agcagccaat tttccagaat    1560
cttttggaaga acctggatga gaccctgggt gaaaaggccc taggtgagat ctctgtgtcc    1620
gtggaaatgg ccgagagtct gctgcaggtt tcagtagtc gatttgaggg cagcactctc    1680
aatgacctgc tcaactccca gatctacacc aagtatgggc tgctgtctaa tgaaccaagc    1740
agctcgtcta cttcacgaaa tcactcctgt accccagatc cagaagagga gtccaagtcg    1800
gaggccagct tctcagagga agagactgag tccctcaaag caaaggccga ggcccctaag    1860
acagaggccg agcccaccaa gacaaggacc gagaccccca tggcacagag tgattctcag    1920
ctgtttaacc agcttctggt gactgagggg atgaccctgc ccactgagat gaaggaggca    1980
gccagtgaaa tggccagagc cttgcggggt cccggtcctc gcagctccct ggatcagcat    2040
gtggcagcgc tcgtggccac tgtgcagata tccagcttgg acacaaacct gcagctttca    2100
gggctctctg ccctctctca ggctgtggag gaggtcactg agcgggacca ccctctggtc    2160
cgtcctgaca gatcgctgag agagaagcta gtgaagatgc tggtggagct gctgaccaac    2220
caggtgggag agaagatggt ggtcgtgcag gccctgcgcc tccttaccctg ctcatgacc    2280
aagcacgagt ggcggccgct cttttgccagg gagggtggca tctatgctgt gctggtctgc    2340
```

```
atgcaagaat ataagacttc tgtcttggtg cagcaggctg ggctggcggc actgaagatg    2400
ctggccgtcg ccagctcctc ggagatcccc acttttgtta ctggccgaga ttctatccac    2460
tctttgtttg atgctcagat gaccagagag atcttcgcca gcatcgactc agccacacgc    2520
ccgggctctg agagcctgct cctcactgtc cctgcagccg tgatcctgat gctgaatact    2580 gagggggtgct cttctgcagc gagaaatggc ttactcctgc tcaacctact tttgtgcaac    2640
caccacactc tgggagacca gattataacc caagagctga gagacacgtt gtttaggcac    2700
tcagggatag caccaagaac agaacctatg cctaccacac gcaccatcct catgatgctt    2760
ctcaatcgct actcagagcc gccgggcagc cctgagcgtg cagcactaga gaccccatc    2820 atccagggtc aggatgggtc ccctgagcta ctgattcgat ccctggttgg gggcccatct    2880
gcagaactac tcctggactt ggagcgtgtg ctgtgccgtg agggcagccc cggaggtgcc    2940
gtgaggcccc tcctcaagcg cctccagcag gagacccagc ctttcctcct gttgctgcgg    3000
actctggatg ctccggggcc caacaagact ctgctgctgt ctgtgctgag ggtcataacc    3060
cgactgctgg atttccctga ggcaatggtc ctccctggc acgaggtctt ggagccctgc    3120
ctcaactgcc tgagtggccc tagcagtgac tccgagattg ttcaggagct gacctgcttc    3180
ctacatcgcc tggcctcgat gcataaggac tatgctgtgg tgctctgctg cctgggagca    3240
aaagagatcc tctccaaagt cctggacaag cactcagctc agctgctgct gggctgtgag    3300
cttcgggacc tggtgacaga gtgtgagaag tacgcacagc tctatagcaa cctcacctcc    3360
agcatcctgg ccggctgcat tcagatggtg ctgggccaga tcgaagacca cagacgaacc    3420
caccaaccca tcaatatccc cttctttgat gtgttcctca ggcatctctg ccagggctcc    3480
agtgtggaag tgaaggagga caagtgctgg gagaaggtgg aggtgtcctc caacccgcac    3540
cgagccagca agctgacgga ccacaacccc aagacctact gggagtccaa cggcagcacc    3600
ggctcccact acatcaccct gcacatgcac cgtggtgttc ttgttaggca gctcactttg    3660
ctggtggcca gtgaggactc aagctacatg ccagccaggg tggtggtgtt tgggggtgac    3720
agcaccagct gcatcggcac tgagctcaac acggtgaatg tgatgccctc tgccagccgg    3780
gtgatcctct tggagaacct gaaccgcttc tggcccatca tccagatccg cataaagcgc    3840
tgccagcagg gcggcattga cacccggggtt cggggtgtgg aggtcctggg ccctaagccc    3900
acattctggc cactgttccg ggagcagctg tgtcgccgaa catgtctctt ctacacaatt    3960
cgggcacaag cctggagccg ggacatagca gaggaccacc ggcgcctcct ccagctctgt    4020
cccagactga acagggtttt gcgccacgag cagaattttg ctgaccgctt cctccctgat    4080
gatgaggccg cccaggcact gggcaagacc tgctggagg ccctggtcag cccctggtg    4140 cagaacatca cctctcccga tgcggaaggc gtgagtgccc tgggatggct gctggatcag    4200
tacttagaac agagagagac ctctcggaac cccttgagtc gagcagcgtc ctttgcttct    4260
cgagttcgtc gcctttgcca cttgctggtg catgtgaaac ctcctcctgg gccttctcct    4320
gagccatcca ctcggcccctt cagcaagaac agcaagggtc gggaccggag cccggcgcct    4380
tcgccagtgc ttccaagcag cagcctgagg aacataaccc agtgctggct gagcgtggtg    4440
caggagcagg tcagcagatt cctggctgca gcttggaggg cccagacttt gtgcctcgt    4500 tactgtaaac tctatgagca cttgcagaga gcaggctccg agctgtttgg gcctcgggca    4560
gccttcatgt ggctctgcg cagtggcttc tctggcgcct tgctgcagca gtccttcctc    4620
actgctgctc acatgagtga gcagtttgcc aggtacattg accaacagat ccagggtggc    4680
```

```
ctgattggtg gagcccctgg agtggaaatg ctggggcagc ttcagcggca cctggaaccc    4740
attatggtcc tttctggtct ggaactggcc acaactttg agcacttcta tcagcattat    4800
atggcggacc gtctcctgag cttgtgttcg agctggctgg aggggctgt gctagagcag    4860 attggcctct gttttcccaa ccgcctccca cagctgatgc tgcagagcct gagcacctct    4920
gaggagctgc agcgccagtt ccacctcttc cagctccagc ggctcgacaa gttgttcttg    4980
gagcaggaag atgaggagga aaagagacta gaggaagagg aggaggaaga ggaggaagag    5040
gaagctgaga agaattatt tatcgaagat ccaagtccag ccatttctat actggtcctg     5100
tcaccacgct gctggcccgt ctccccactc tgctacctgt accatcccag aaagtgcctt    5160
cccacagaat tctgtgatgc ccttgaccgt ttctccagtt tctacagcca gagtcagaac    5220
catccagtcc tggacatggg accacatcgg cgactgcagt ggacgtggct gggccgggct    5280
gagctgcagt ttgggaagca gatactgcat gtgtccaccg tgcagatgtg gctgctgctg    5340
aaattcaatc agacagagga ggtgtcagta gagaccttgc tgaaggattc tgacctctcc    5400
ccagagctgc tgctccaggc actcgtgccc ctcacctcag ggaatggccc tttgaccctg    5460
catgagggcc aggactttcc acacgggggt gtgctgcggc ttcatgagcc tgggccccag    5520
cgcagtgggg aggccctgtg gctgatacct ccccaggcat acctgaacgt agagaaggat    5580
gaaggccgaa ccctggaaca gaagaggaat ctcttgagct gtcttcttgt tcgtattctc    5640
aaagcccatg gggaaaaggg cctccacatt gatcagctgg ttttgtctggt gctggaggcc    5700 tggcagaagg gtccaaatcc tcctggaacc ctgggccaca ctgttgctgg ggtgtggcc     5760 tgtaccagta cagatgtcct ctcttgcatc ctgcacctct taggccaggg ctacgtgaaa    5820
cggcgtgatg accggcccca gatcctgatg tatgccgctc cagagcccat ggggccctgc    5880
cggggtcagg cagatgtccc ttctgtggc agccagagcg aaacctccaa gcccagccca    5940
gaagctgtgg ctaccctggc atctctacag ctgcctgcag gccgcaccat gagcccccag    6000
gaagtagaag ggttgatgaa gcagacggtg cgtcaggtgc aggagacgct gaacttagag    6060
ccagatgtcg ctcagcacct tttggctcat tcccactggg gcgctgaaca gctgctgcag    6120
agctacagtg aggaccctga gccactgctg ctggcagctg gctgtgcgt acaccaggct    6180 caggctgtac ccgtacggcc tgaccactgc cccgtctgtg tgagccccct ggggtgtgac    6240
gacgacctgc cctctctctg ctgcatgcac tattgctgta agtcttgctg gaatgagtac    6300
ctgacaactc ggatcgagca gaaccttgtt ttgaattgca cctgccccat tgccgactgc    6360
cccgcccagc ccaccggagc cttcattcgt gccatcgtct cctcgccaga ggtcatctcc    6420
aagtatgaga aggcgctcct gcgtggctat gtggagagct gctccaacct gacctggtgc    6480
accaaccccc agggctgcga ccgcatcctg tgccgcagg gcctgggctg tgggaccacc    6540
tgctccaagt gtggctgggc ctcttgcttc aactgtagct tccctgaggc acactaccct    6600
gctagctgtg ccatatgtc tcagtgggtc gacgacggtg gctactatga cggcatgagc    6660
gtggaggcgc agagcaagca cctggccaag ctcatctcca agcgctgtcc cagctgtcag    6720
gctcccatcg agaagaacga ggggtgcctg cacatgacct gtgccaaatg taaccatgga    6780
ttctgctggg gctgcctcaa gtcctggaag ccaaatcaca aagactatta caactgctct    6840
gccatggtaa gcaaggcagc tcgccaggag aagcggtttc aggactataa tgagaggtgc    6900
actttccatc accaggcgcg ggagtttgct gtgaacttgc ggaaccgggt gtctgccatc    6960
catgaagtgc ccccgcccag atccttcacc ttcctcaatg atgcctgcca gggactggag    7020
caggctcgga aggtgctggc ctacgcctgc gtgtacagct tctacagcca ggacgcagag    7080
```

-continued

```
tacatggatg tggtggagca gcagacagag aacctggagc tgcacaccaa tgccctgcag    7140
atcctcctgg aggaaaccct gctgcggtgc agagacctgg cctcctccct gcgcctcctg    7200
cgggccgact gcctcagcac gggcatggag ctgctccggc ggatccagga gaggctgctt    7260
gccatcctgc agcattctgc ccaggatttc cgggttggtc ttcagagtcc atcagtagag    7320
gcctgggagg caaaaggacc caacatgcct ggcagtcagc cccaggcctc ctcagggcca    7380
gaggcagaag aggaggagga agacgatgag gatgatgtgc ccgagtggca gcaggatgag    7440
tttgatgagg agctggacaa tgacagcttc tcctacgatg agtctgagaa cctggaccaa    7500
gagactttct tctttggtga tgaggaagag gatgaagatg aggcctatga ctga           7554
```

<210> SEQ ID NO 15
<211> LENGTH: 2048
<212> TYPE: PRT
<213> ORGANISM: Homo sapiens

<400> SEQUENCE: 15

```
Met Leu Arg Val Ile Val Glu Ser Ala Ser Asn Ile Pro Lys Thr Lys
1               5                   10                  15

Phe Gly Lys Pro Asp Pro Ile Val Ser Val Ile Phe Lys Asp Glu Lys
                20                  25                  30

Lys Lys Thr Lys Lys Val Asp Asn Glu Leu Asn Pro Val Trp Asn Glu
            35                  40                  45

Ile Leu Glu Phe Asp Leu Arg Gly Ile Pro Leu Asp Phe Ser Ser Ser
        50                  55                  60

Leu Gly Ile Ile Val Lys Asp Phe Glu Thr Ile Gly Gln Asn Lys Leu
65                  70                  75                  80

Ile Gly Thr Ala Thr Val Ala Leu Lys Asp Leu Thr Gly Asp Gln Ser
                85                  90                  95

Arg Ser Leu Pro Tyr Lys Leu Ile Ser Leu Leu Asn Glu Lys Gly Gln
                100                 105                 110

Asp Thr Gly Ala Thr Ile Asp Leu Val Ile Gly Tyr Asp Pro Pro Ser
            115                 120                 125

Ala Pro His Pro Asn Asp Leu Ser Gly Pro Ser Val Pro Gly Met Gly
        130                 135                 140

Gly Asp Gly Glu Glu Asp Glu Gly Asp Glu Asp Arg Leu Asp Asn Ala
145                 150                 155                 160

Val Arg Gly Pro Gly Pro Lys Gly Pro Val Gly Thr Val Ser Glu Ala
                165                 170                 175

Gln Leu Ala Arg Arg Leu Thr Lys Val Lys Asn Ser Arg Arg Met Leu
            180                 185                 190

Ser Asn Lys Pro Gln Asp Phe Gln Ile Arg Val Arg Val Ile Glu Gly
        195                 200                 205

Arg Gln Leu Ser Gly Asn Asn Ile Arg Pro Val Val Lys Val His Val
    210                 215                 220

Cys Gly Gln Thr His Arg Thr Arg Ile Lys Arg Gly Asn Asn Pro Phe
225                 230                 235                 240

Phe Asp Glu Leu Phe Phe Tyr Asn Val Asn Met Thr Pro Ser Glu Leu
                245                 250                 255

Met Asp Glu Ile Ile Ser Ile Arg Val Tyr Asn Ser His Ser Leu Arg
            260                 265                 270

Ala Asp Cys Leu Met Gly Glu Phe Lys Ile Asp Val Gly Phe Val Tyr
        275                 280                 285
```

-continued

```
Asp Glu Pro Gly His Ala Val Met Arg Lys Trp Leu Leu Asn Asp
    290                 295                 300
Pro Glu Asp Thr Ser Ser Gly Ser Lys Gly Tyr Met Lys Val Ser Met
305                 310                 315                 320
Phe Val Leu Gly Thr Gly Asp Glu Pro Pro Glu Arg Arg Asp Arg
                325                 330                 335
Asp Asn Asp Ser Asp Asp Val Glu Ser Asn Leu Leu Leu Pro Ala Gly
                340                 345                 350
Ile Ala Leu Arg Trp Val Thr Phe Leu Leu Lys Ile Tyr Arg Ala Glu
            355                 360                 365
Asp Ile Pro Gln Met Asp Asp Ala Phe Ser Gln Thr Val Lys Glu Ile
    370                 375                 380
Phe Gly Gly Asn Ala Asp Lys Lys Asn Leu Val Asp Pro Phe Val Glu
385                 390                 395                 400
Val Ser Phe Ala Gly Lys Lys Val Cys Thr Asn Ile Ile Glu Lys Asn
                405                 410                 415
Ala Asn Pro Glu Trp Asn Gln Val Val Asn Leu Gln Ile Lys Phe Pro
                420                 425                 430
Ser Val Cys Glu Lys Ile Lys Leu Thr Ile Tyr Asp Trp Asp Arg Leu
            435                 440                 445
Thr Lys Asn Asp Val Val Gly Thr Thr Tyr Leu His Leu Ser Lys Ile
    450                 455                 460
Ala Ala Ser Gly Gly Glu Val Glu Val Asn Thr Gly Glu Thr Glu Val
465                 470                 475                 480
Gly Phe Val Pro Thr Phe Gly Pro Cys Tyr Leu Asn Leu Tyr Gly Ser
                485                 490                 495
Pro Arg Glu Tyr Thr Gly Phe Pro Asp Pro Tyr Asp Glu Leu Asn Thr
            500                 505                 510
Gly Lys Gly Glu Gly Val Ala Tyr Arg Gly Arg Ile Leu Val Glu Leu
    515                 520                 525
Ala Thr Phe Leu Glu Lys Thr Pro Pro Asp Lys Lys Leu Glu Pro Ile
530                 535                 540
Ser Asn Asp Asp Leu Leu Val Val Glu Lys Tyr Gln Arg Arg Lys
545                 550                 555                 560
Tyr Ser Leu Ser Ala Val Phe His Ser Ala Thr Met Leu Gln Asp Val
                565                 570                 575
Gly Glu Ala Ile Gln Phe Glu Val Ser Ile Gly Asn Tyr Gly Asn Lys
            580                 585                 590
Phe Asp Thr Thr Cys Lys Pro Leu Ala Ser Thr Thr Gln Tyr Ser Arg
    595                 600                 605
Ala Val Phe Asp Gly Asn Tyr Tyr Tyr Leu Pro Trp Ala His Thr
610                 615                 620
Lys Pro Val Val Thr Leu Thr Ser Tyr Trp Glu Asp Ile Ser His Arg
625                 630                 635                 640
Leu Asp Ala Val Asn Thr Leu Leu Ala Met Ala Glu Arg Leu Gln Thr
                645                 650                 655
Asn Ile Glu Ala Leu Lys Ser Gly Ile Gln Gly Lys Ile Pro Ala Asn
                660                 665                 670
Gln Leu Ala Glu Leu Trp Leu Lys Leu Ile Asp Glu Val Ile Glu Asp
            675                 680                 685
Thr Arg Tyr Thr Leu Pro Leu Thr Glu Gly Lys Ala Asn Val Thr Val
    690                 695                 700
Leu Asp Thr Gln Ile Arg Lys Leu Arg Ser Arg Ser Leu Ser Gln Ile
```

```
              705                 710                 715                 720
        His Glu Ala Ala Val Arg Met Arg Ser Glu Ala Thr Asp Val Lys Ser
                            725                 730                 735
        Thr Leu Ala Glu Ile Glu Asp Trp Leu Asp Lys Leu Met Gln Leu Thr
                            740                 745                 750
        Glu Glu Pro Gln Asn Ser Met Pro Asp Ile Ile Ile Trp Met Ile Arg
                            755                 760                 765
        Gly Glu Lys Arg Leu Ala Tyr Ala Arg Ile Pro Ala His Gln Val Leu
                            770                 775                 780
        Tyr Ser Thr Ser Gly Glu Asn Ala Ser Gly Lys Tyr Cys Gly Lys Thr
        785                 790                 795                 800
        Gln Thr Ile Phe Leu Lys Tyr Pro Gln Glu Lys Asn Asn Gly Pro Lys
                            805                 810                 815
        Val Pro Val Glu Leu Arg Val Asn Ile Trp Leu Gly Leu Ser Ala Val
                            820                 825                 830
        Glu Lys Lys Phe Asn Ser Phe Ala Glu Gly Thr Phe Thr Val Phe Ala
                            835                 840                 845
        Glu Met Tyr Glu Asn Gln Ala Leu Met Phe Gly Lys Trp Gly Thr Ser
                            850                 855                 860
        Gly Leu Val Gly Arg His Lys Phe Ser Asp Val Thr Gly Lys Ile Lys
        865                 870                 875                 880
        Leu Lys Arg Glu Phe Phe Leu Pro Pro Lys Gly Trp Glu Trp Glu Gly
                            885                 890                 895
        Glu Trp Ile Val Asp Pro Glu Arg Ser Leu Leu Thr Glu Ala Asp Ala
                            900                 905                 910
        Gly His Thr Glu Phe Thr Asp Glu Val Tyr Gln Asn Glu Ser Arg Tyr
                            915                 920                 925
        Pro Gly Gly Asp Trp Lys Pro Ala Glu Asp Thr Tyr Thr Asp Ala Asn
                            930                 935                 940
        Gly Asp Lys Ala Ala Ser Pro Ser Glu Leu Thr Cys Pro Pro Gly Trp
        945                 950                 955                 960
        Glu Trp Glu Asp Asp Ala Trp Ser Tyr Asp Ile Asn Arg Ala Val Asp
                            965                 970                 975
        Glu Lys Gly Trp Glu Tyr Gly Ile Thr Ile Pro Asp His Lys Pro
                            980                 985                 990
        Lys Ser Trp Val Ala Ala Glu Lys Met Tyr His Thr His Arg Arg
                            995                 1000                1005
        Arg Leu Val Arg Lys Arg Lys Asp Leu Thr Gln Thr Ala Ser Ser
                1010                1015                1020
        Thr Ala Arg Ala Met Glu Glu Leu Gln Asp Gln Glu Gly Trp Glu Tyr
        1025                1030                1035                1040
        Ala Ser Leu Ile Gly Trp Lys Phe His Trp Lys Gln Arg Ser Ser Asp
                            1045                1050                1055
        Thr Phe Arg Arg Arg Arg Trp Arg Arg Lys Met Ala Pro Ser Glu Thr
                            1060                1065                1070
        His Gly Ala Ala Ala Ile Phe Lys Leu Glu Gly Ala Leu Gly Ala Asp
                            1075                1080                1085
        Thr Thr Glu Asp Gly Asp Glu Lys Ser Leu Glu Lys Gln Lys His Ser
                            1090                1095                1100
        Ala Thr Thr Val Phe Gly Ala Asn Thr Pro Ile Val Ser Cys Asn Phe
        1105                1110                1115                1120
        Asp Arg Val Tyr Ile Tyr His Leu Arg Cys Tyr Val Tyr Gln Ala Arg
                            1125                1130                1135
```

```
Asn Leu Leu Ala Leu Asp Lys Asp Ser Phe Ser Asp Pro Tyr Ala His
            1140                1145                1150
Ile Cys Phe Leu His Arg Ser Lys Thr Thr Glu Ile His Ser Thr
            1155                1160                1165
Leu Asn Pro Thr Trp Asp Gln Thr Ile Ile Phe Asp Glu Val Glu Ile
    1170                1175                1180
Tyr Gly Glu Pro Gln Thr Val Leu Gln Asn Pro Pro Lys Val Ile Met
1185                1190                1195                1200
Glu Leu Phe Asp Asn Asp Gln Val Gly Lys Asp Glu Phe Leu Gly Arg
            1205                1210                1215
Ser Ile Phe Ser Pro Val Val Lys Leu Asn Ser Glu Met Asp Ile Thr
            1220                1225                1230
Pro Lys Leu Leu Trp His Pro Val Met Asn Gly Asp Lys Ala Cys Gly
            1235                1240                1245
Asp Val Leu Val Thr Ala Glu Leu Ile Leu Arg Gly Lys Asp Gly Ser
            1250                1255                1260
Asn Leu Pro Ile Leu Pro Pro Gln Arg Ala Pro Asn Leu Tyr Met Val
1265                1270                1275                1280
Pro Gln Gly Ile Arg Pro Val Val Gln Leu Thr Ala Ile Glu Ile Leu
            1285                1290                1295
Ala Trp Gly Leu Arg Asn Met Lys Asn Phe Gln Met Ala Ser Ile Thr
            1300                1305                1310
Ser Pro Ser Leu Val Val Glu Cys Gly Gly Glu Arg Val Glu Ser Val
            1315                1320                1325
Val Ile Lys Asn Leu Lys Lys Thr Pro Asn Phe Pro Ser Ser Val Leu
            1330                1335                1340
Phe Met Lys Val Phe Leu Pro Lys Glu Glu Leu Tyr Met Pro Pro Leu
1345                1350                1355                1360
Val Ile Lys Val Ile Asp His Arg Gln Phe Gly Arg Lys Pro Val Val
            1365                1370                1375
Gly Gln Cys Thr Ile Glu Arg Leu Asp Arg Phe Arg Cys Asp Pro Tyr
            1380                1385                1390
Ala Gly Lys Glu Asp Ile Val Pro Gln Leu Lys Ala Ser Leu Leu Ser
            1395                1400                1405
Ala Pro Pro Cys Arg Asp Ile Val Ile Glu Met Glu Asp Thr Lys Pro
            1410                1415                1420
Leu Leu Ala Ser Lys Leu Thr Glu Lys Glu Glu Ile Val Asp Trp
1425                1430                1435                1440
Trp Ser Lys Phe Tyr Ala Ser Ser Gly Glu His Glu Lys Cys Gly Gln
            1445                1450                1455
Tyr Ile Gln Lys Gly Tyr Ser Leu Lys Ile Tyr Asn Cys Glu Leu
            1460                1465                1470
Glu Asn Val Ala Glu Phe Glu Gly Leu Thr Asp Phe Ser Asp Thr Phe
    1475                1480                1485
Lys Leu Tyr Arg Gly Lys Ser Asp Glu Asn Glu Asp Pro Ser Val Val
            1490                1495                1500
Gly Glu Phe Lys Gly Ser Phe Arg Ile Tyr Pro Leu Pro Asp Asp Pro
1505                1510                1515                1520
Ser Val Pro Ala Pro Pro Arg Gln Phe Arg Glu Leu Pro Asp Ser Val
            1525                1530                1535
Pro Gln Glu Cys Thr Val Arg Ile Tyr Ile Val Arg Gly Leu Glu Leu
            1540                1545                1550
```

-continued

Gln Pro Gln Asp Asn Asn Gly Leu Cys Asp Pro Tyr Ile Lys Ile Thr
        1555                1560                1565

Leu Gly Lys Lys Val Ile Glu Asp Arg Asp His Tyr Ile Pro Asn Thr
1570                1575                1580

Leu Asn Pro Val Phe Gly Arg Met Tyr Glu Leu Ser Cys Tyr Leu Pro
1585                1590                1595                1600

Gln Glu Lys Asp Leu Lys Ile Ser Val Tyr Asp Tyr Asp Thr Phe Thr
        1605                1610                1615

Arg Asp Glu Lys Val Gly Glu Thr Ile Ile Asp Leu Glu Asn Arg Phe
        1620                1625                1630

Leu Ser Arg Phe Gly Ser His Cys Gly Ile Pro Glu Glu Tyr Cys Val
        1635                1640                1645

Ser Gly Val Asn Thr Trp Arg Asp Gln Leu Arg Pro Thr Gln Leu Leu
        1650                1655                1660

Gln Asn Val Ala Arg Phe Lys Gly Phe Pro Gln Pro Ile Leu Ser Glu
1665                1670                1675                1680

Asp Gly Ser Arg Ile Arg Tyr Gly Gly Arg Asp Tyr Ser Leu Asp Glu
        1685                1690                1695

Phe Glu Ala Asn Lys Ile Leu His Gln His Leu Gly Ala Pro Glu Glu
        1700                1705                1710

Arg Leu Ala Leu His Ile Leu Arg Thr Gln Gly Leu Val Pro Glu His
        1715                1720                1725

Val Glu Thr Arg Thr Leu His Ser Thr Phe Gln Pro Asn Ile Ser Gln
        1730                1735                1740

Gly Lys Leu Gln Met Trp Val Asp Val Phe Pro Lys Ser Leu Gly Pro
1745                1750                1755                1760

Pro Gly Pro Pro Phe Asn Ile Thr Pro Arg Lys Ala Lys Lys Tyr Tyr
        1765                1770                1775

Leu Arg Val Ile Ile Trp Asn Thr Lys Asp Val Ile Leu Asp Glu Lys
        1780                1785                1790

Ser Ile Thr Gly Glu Glu Met Ser Asp Ile Tyr Val Lys Gly Trp Ile
        1795                1800                1805

Pro Gly Asn Glu Glu Asn Lys Gln Lys Thr Asp Val His Tyr Arg Ser
        1810                1815                1820

Leu Asp Gly Glu Gly Asn Phe Asn Trp Arg Phe Val Phe Pro Phe Asp
1825                1830                1835                1840

Tyr Leu Pro Ala Glu Gln Leu Cys Ile Val Ala Lys Lys Glu His Phe
        1845                1850                1855

Trp Ser Ile Asp Gln Thr Glu Phe Arg Ile Pro Pro Arg Leu Ile Ile
        1860                1865                1870

Gln Ile Trp Asp Asn Asp Lys Phe Ser Leu Asp Asp Tyr Leu Gly Phe
        1875                1880                1885

Leu Glu Leu Asp Leu Arg His Thr Ile Ile Pro Ala Lys Ser Pro Glu
        1890                1895                1900

Lys Cys Arg Leu Asp Met Ile Pro Asp Leu Lys Ala Met Asn Pro Leu
1905                1910                1915                1920

Lys Ala Lys Thr Ala Ser Leu Phe Glu Gln Lys Ser Met Lys Gly Trp
        1925                1930                1935

Trp Pro Cys Tyr Ala Glu Lys Asp Gly Ala Arg Val Met Ala Gly Lys
        1940                1945                1950

Val Glu Met Thr Leu Glu Ile Leu Asn Glu Lys Glu Ala Asp Glu Arg
        1955                1960                1965

Pro Ala Gly Lys Gly Arg Asp Glu Pro Asn Met Asn Pro Lys Leu Asp

Leu Pro Asn Arg Pro Glu Thr Ser Phe Leu Trp Phe Thr Asn Pro Cys
1985                1990                1995                2000

Lys Thr Met Lys Phe Ile Val Trp Arg Arg Phe Lys Trp Val Ile Ile
            2005                2010                2015

Gly Leu Leu Phe Leu Leu Ile Leu Leu Leu Phe Val Ala Val Leu Leu
            2020                2025                2030

Tyr Ser Leu Pro Asn Tyr Leu Ser Met Lys Ile Val Lys Pro Asn Val
            2035                2040                2045

<210> SEQ ID NO 16
<211> LENGTH: 6147
<212> TYPE: DNA
<213> ORGANISM: Homo sapiens

<400> SEQUENCE: 16

| | | | | | |
|---|---|---|---|---|---|
| catgctgcga | gtgattgtgg | aatctgccag | caatatccct | aaaacgaaat | ttggcaagcc | 60 |
| ggatcctatt | gtttctgtca | tttttaagga | tgagaaaaag | aaaacaaaga | aagttgataa | 120 |
| tgaattgaac | cctgtctgga | atgagatttt | ggagtttgac | ttgaggggta | taccactgga | 180 |
| cttttcatct | tcccttggga | ttattgtgaa | agattttgag | acaattggac | aaaataaatt | 240 |
| aattggcacg | gcgactgtag | ccctgaagga | cctgactggt | gaccagagca | gatccctgcc | 300 |
| gtacaagctg | atctccctgc | taaatgaaaa | agggcaagat | actggggcca | ccattgactt | 360 |
| ggtgatcggc | tatgatccgc | cttctgctcc | acatccaaat | gacctgagcg | ggcccagcgt | 420 |
| gccaggcatg | ggaggagatg | gggaagaaga | tgaaggtgat | gaagacaggt | tggacaatgc | 480 |
| agtcagggc | cctgggccca | aggggccagt | tgggacggtg | tcggaagctc | agcttgctcg | 540 |
| gaggctcacc | aaagtaaaga | acagccggcg | gatgctgtca | aataagccac | aggacttcca | 600 |
| gatccgcgtc | cgagtgattg | agggccgaca | gttaagtggt | aacaacataa | ggcctgtggt | 660 |
| caaagttcac | gtctgtggcc | agacacaccg | aacaagaatc | aagagaggaa | caaccccttt | 720 |
| ttttgatgag | ttgtttttct | acaatgtcaa | catgaccct | tctgaattga | tggatgagat | 780 |
| catcagcatc | cgggtttata | attctcactc | tctgcgggca | gattgtctga | tggggaatt | 840 |
| taagattgat | gttggatttg | tttatgatga | acctggccat | gctgtcatga | aaagtggct | 900 |
| tcttctcaat | gacccggaag | ataccagttc | aggttctaaa | ggttatatga | aagtcagcat | 960 |
| gtttgtcctg | ggaaccggag | atgagcctcc | tcctgagaga | cgagatcgtg | ataatgacag | 1020 |
| tgatgatgtg | gagagtaatt | tgttactccc | tgctggcatt | gccctccggt | gggtgacctt | 1080 |
| cttgctgaaa | atctaccgag | ctgaggacat | cccccagatg | gatgatgcct | tctcacagac | 1140 |
| agtaaaggaa | atatttggag | gcaatgcaga | taagaaaaat | ctcgtggatc | cttttgtaga | 1200 |
| agtttccttt | gctggaaaaa | aggtttgtac | aaacataatt | gagaaaatg | caaacccaga | 1260 |
| gtggaatcag | gtcgtcaatc | ttcagatcaa | gtttccttca | gtgtgtgaaa | aaataaaact | 1320 |
| aacaatatat | gactgggacc | gtcttactaa | aaatgatgta | gttggaacaa | catatctaca | 1380 |
| cctctctaaa | attgctgcct | ctggtgggga | agtggaagta | acacaggag | aaacagaggt | 1440 |
| aggctttgtt | ccaacgtttg | gaccttgtta | cctgaatctt | tatggaagcc | ccagggagta | 1500 |
| cacgggattc | ccagaccct | atgatgagct | gaatactgga | aaggggaag | gagttgccta | 1560 |
| cagaggcagg | atcttggttg | aattagccac | ttttcttgag | aagacaccac | cagataaaaa | 1620 |
| gcttgagccc | atttcaaatg | atgacctgct | ggttgttgag | aaataccagc | gaaggcgaaa | 1680 |
| gtacagcctg | tctgccgtgt | tcattcagc | caccatgttg | caagatgttg | gtgaggccat | 1740 |

```
tcagtttgaa gtcagcattg ggaactatgg caacaagttt gacaccacct gtaagccttt    1800
ggcatcaaca actcagtaca gccgtgctgt atttgatggc aactactatt attacttgcc    1860
ttgggcccac accaagccag ttgttaccct gacttcatac tgggaggata ttagtcatcg    1920
cctggatgcg gtgaacactc tcctagctat ggcagaacgg ctgcaaacaa atatagaagc    1980
tctaaaatca gggatacaag gtaaaattcc tgcaaccag ctggctgaat tgtggctgaa     2040
gctgatagat gaagttatag aagacacgag atacacgttg cctctcacag aaggaaaagc    2100
caacgtcaca gttctcgata ctcagatccg aaagctgcgg tccaggtctc tctcccaaat    2160
acatgaggcg gctgtgagga tgaggtcgga agccacagat gtgaagtcca cactggcaga    2220
aattgaggac tggcttgata aattaatgca gctgactgaa gagccacaga acagcatgcc    2280
tgacatcatc atctggatga tccggggaga aagagactg gcctatgcac gaattcccgc     2340
acatcaggtc ttgtactcca ccagtggtga gaatgcatct ggaaaatact gtgggaaaac    2400
ccaaaccatc tttctgaagt atccacagga gaaaaacaac gggccaaagg tgcctgtgga    2460
gttgcgagtg aacatctggc taggcttaag tgctgtggag aagaagttta acagcttcgc    2520
agaaggaact ttcaccgtct ttgctgaaat gtatgaaaat caagctctca tgtttggaaa    2580
atggggtact tctggattag taggacgtca taagttttct gatgtcacag aaaaataaa    2640 actcaagagg gaatttttc tgcctccaaa aggctgggaa tgggaaggag agtggatagt    2700
tgatcctgaa agaagcttgc tgactgaggc agatgcaggt cacacggagt tcactgatga    2760
agtctatcag aacagagagcc gctaccccgg gggcgactgg aagccggccg aggacaccta    2820 cacgatgcg aacggcgata agcagcatc acccagcgag ttgacttgtc ctccaggttg      2880
ggaatgggaa gatgatgcat ggtcttatga cataaatcga gcggtggatg agaaaggctg    2940
ggaatatgga atcaccattc ctcctgatca taagcccaaa tcctgggttg cagcagagaa    3000
aatgtaccac actcatagac ggcgaaggct ggtccgaaaa cgcaagaaag atttaacaca    3060
gactgcttca agcaccgcaa gggccatgga ggaattgcaa gaccaagagg ctgggaata    3120 tgcttctcta attggctgga aatttcactg gaaacaacgt agttcagata ccttccgccg    3180
cagacgctgg aggagaaaaa tggctcccttc agaaacacat ggtgcagctg ccatctttaa   3240
acttgaaggt gcccttgggg cagacactac cgaagatggg gatgagaaga gcctggagaa    3300
acagaagcac agtgccacca ctgtgttcgg agcaaacacc cccattgttt cctgcaattt    3360
tgacagagtc tacatctacc atctgcgctg ctatgtctat caagccagaa acctcttggc    3420
tttagataag gatagctttt cagatccata tgctcatatc tgtttcctcc atcggagcaa    3480
aaccactgag atcatccatt caaccctgaa tcccacgtgg gaccaaacaa ttatattcga    3540
tgaagttgaa atctatgggg aaccccaaac agttctacag aatccaccca agttatcat    3600 ggaactttt gacaatgacc aagtgggcaa agatgaattt ttaggacgaa gcattttctc    3660
tcctgtggta aaactgaact cagaaatgga catcacaccc aaacttctct ggcacccagt    3720
aatgaatgga gacaaagcct gcggggatgt tcttgtaact gcagagctga ttctgagggg    3780
caaggatggc tccaaccttc ccattcttcc ccctcaaagg gcgccaaatc tatacatggt    3840
cccccagggg atcaggcctg tggtccagct cactgccatt gagattctag cttgggcttt    3900
aagaaatatg aaaaacttcc agatggcttc tatcacatcc cccagtcttg ttgtggagtg    3960
tggaggagaa agggtggaat cggtggtgat caaaaacctt aagaagacac ccaactttcc    4020
aagttctgtt ctcttcatga aagtgttctt gcccaaggag gaattgtaca tgccccact    4080
```

-continued

```
ggtgatcaag gtcatcgacc acaggcagtt tgggcggaag cctgtcgtcg gccagtgcac    4140
catcgagcgc ctggaccgct tcgctgtga cccttatgca gggaaagagg acatcgtccc     4200
acagctcaaa gcctcccttc tgtctgcccc accatgccgg acatcgtta tcgaaatgga     4260 agacaccaaa ccattactgg cttctaagct gacagaaaag gaggaagaaa tcgtggactg    4320
gtggagtaaa ttttatgctt cctcagggga acatgaaaaa tgcggacagt atattcagaa    4380
aggctattcc aagctcaaga tatataattg tgaactagaa aatgtagcag aatttgaggg    4440
cctgacagac ttctcagata cgttcaagtt gtaccgaggc aagtcggatg aaaatgaaga    4500
tccttctgtg gttggagagt ttaagggctc ctttcggatc taccctctgc cggatgaccc    4560
cagcgtgcca gcccctccca gacagtttcg ggaattacct gacagcgtcc acaggaatg    4620 cacggttagg atttacattg ttcgaggctt agagctccag ccccaggaca caatggcct    4680 gtgtgaccct tacataaaaa taacactggg caaaaaagtc attgaagacc gagatcacta    4740
cattcccaac actctcaacc cagtctttgg caggatgtac gaactgagct gctacttacc    4800
tcaagaaaaa gacctgaaaa tttctgtcta tgattatgac acctttaccc gggatgaaaa    4860
agtaggagaa caattattg atctggaaaa ccgattcctt tcccgctttg gtcccactg     4920 cggcatacca gaggagtact gtgtttctgg agtcaatacc tggcgagatc aactgagacc    4980
aacacagctg cttcaaaatg tcgccagatt caaaggcttc ccacaaccca tcctttccga    5040
agatgggagt agaatcagat atggaggacg agactacagc ttggatgaat ttgaagccaa    5100
caaaatcctg caccagcacc tcggggcccc tgaagagcgg cttgctcttc acatcctcag    5160
gactcagggg ctggtccctg agcacgtgga acaaggact tgcacagca ccttccagcc     5220 caacatttcc cagggaaaac ttcagatgtg ggtggatgtt ttccccaaga gtttggggcc    5280
accaggccct ccttttcaaca tcacaccccg gaaagccaag aaatactacc tgcgtgtgat    5340
catctggaac accaaggacg ttatcttgga cgagaaaagc atcacaggag aggaaatgag    5400
tgacatctac gtcaaaggct ggattcctgg caatgaagaa acaaacaga aaacagatgt     5460 ccattacaga tctttggatg gtgaagggaa ttttaactgg cgatttgttt cccgtttga    5520 ctaccttcca gccgaacaac tctgtatcgt tgcgaaaaaa gagcatttct ggagtattga    5580
ccaaacggaa tttcgaatcc cacccaggct gatcattcag atatgggaca atgacaagtt    5640
ttctctggat gactacttgg gttttcctaga acttgacttg cgtcacacga tcattcctgc    5700
aaaatcacca gagaaatgca ggttggacat gattccggac ctcaaagcca tgaacccct     5760 taaagccaag acagcctccc tctttgagca gaagtccatg aaaggatggt ggccatgcta    5820
cgcagagaaa gatggcgccc gcgtaatggc tgggaaagtg gagatgacat ggaaatcct     5880 caacgagaag gaggccgacg agaggccagc cgggaagggg cgggacgaac caacatgaa     5940 ccccaagctg gacttaccaa atcgaccaga aacctccttc ctctggttca ccaacccatg    6000
caagaccatg aagttcatcg tgtggcgccg ctttaagtgg gtcatcatcg gcttgctgtt    6060
cctgcttatc ctgctgctct tcgtggccgt gctcctctac tctttgccga actatttgtc    6120
aatgaagatt gtaaagccaa atgtgta                                       6147
```

<210> SEQ ID NO 17
<211> LENGTH: 336
<212> TYPE: PRT
<213> ORGANISM: Homo sapiens

<400> SEQUENCE: 17

Met Glu Arg Lys Ile Ser Arg Ile His Leu Val Ser Glu Pro Ser Ile

```
  1               5                   10                  15
Thr His Phe Leu Gln Val Ser Trp Glu Lys Thr Leu Glu Ser Gly Phe
                20                  25                  30

Val Ile Thr Leu Thr Asp Gly His Ser Ala Trp Thr Gly Thr Val Ser
                35                  40                  45

Glu Ser Glu Ile Ser Gln Gly Ala Asp Asp Met Ala Met Glu Lys Gly
                50                  55                  60

Lys Tyr Val Gly Glu Leu Arg Lys Ala Leu Leu Ser Gly Ala Gly Pro
65                  70                  75                  80

Ala Asp Val Tyr Thr Phe Asn Phe Ser Lys Glu Ser Cys Tyr Phe Phe
                85                  90                  95

Phe Glu Lys Asn Leu Lys Asp Val Ser Phe Arg Leu Gly Ser Phe Asn
                100                 105                 110

Leu Glu Lys Val Glu Asn Pro Ala Glu Val Ile Arg Glu Leu Ile Cys
                115                 120                 125

Tyr Cys Leu Asp Thr Ile Ala Glu Asn Gln Ala Lys Asn Glu His Leu
                130                 135                 140

Gln Lys Glu Asn Glu Arg Leu Leu Arg Asp Trp Asn Asp Val Gln Gly
145                 150                 155                 160

Arg Phe Glu Lys Cys Val Ser Ala Lys Glu Ala Leu Glu Thr Asp Leu
                165                 170                 175

Tyr Lys Arg Phe Ile Leu Val Leu Asn Glu Lys Lys Thr Lys Ile Arg
                180                 185                 190

Ser Leu His Asn Lys Leu Leu Asn Ala Ala Gln Glu Arg Glu Lys Asp
                195                 200                 205

Ile Lys Gln Glu Gly Glu Thr Ala Ile Cys Ser Glu Met Thr Ala Asp
210                 215                 220

Arg Asp Pro Val Tyr Asp Glu Ser Thr Asp Glu Ser Glu Asn Gln
225                 230                 235                 240

Thr Asp Leu Ser Gly Leu Ala Ser Ala Ala Val Ser Lys Asp Ser
                245                 250                 255

Ile Ile Ser Ser Leu Asp Val Thr Asp Ile Ala Pro Ser Arg Lys Arg
                260                 265                 270

Arg Gln Arg Met Gln Arg Asn Leu Gly Thr Glu Pro Lys Met Ala Pro
                275                 280                 285

Gln Glu Asn Gln Leu Gln Glu Lys Glu Asn Ser Arg Pro Asp Ser Ser
                290                 295                 300

Leu Pro Glu Thr Ser Lys Lys Glu His Ile Ser Ala Glu Asn Met Ser
305                 310                 315                 320

Leu Glu Thr Leu Arg Asn Ser Ser Pro Glu Asp Leu Phe Asp Glu Ile
                325                 330                 335
```

<210> SEQ ID NO 18
<211> LENGTH: 1011
<212> TYPE: DNA
<213> ORGANISM: Homo sapiens

<400> SEQUENCE: 18

```
aatggagaga aaataagca gaatccacct tgtttctgaa cccagtataa ctcatttct    60 acaagtatct tgggagaaaa cactggaatc tggttttgtt attacactta ctgatggtca   120
ttcagcatgg actgggacag tttctgaatc agagatttcc caagaagctg atgacatggc   180
aatggaaaaa gggaaatatg ttggtgaact gagaaaagca ttgttgtcag agcaggacc    240 agctgatgta tacacgttta atttttctaa agagtcttgt tatttcttct ttgagaaaaa   300
```

```
cctgaaagat gtctcattca gacttggttc cttcaaccta gagaaagttg aaaacccagc    360
tgaagtcatt agagaactta tttgttattg cttggacacc attgcagaaa atcaagccaa    420
aaatgagcac ctgcagaaag aaaatgaaag gcttctgaga gattggaatg atgttcaagg    480
acgatttgaa aaatgtgtga gtgctaagga agctttggag actgatcttt ataagcggtt    540
tattctggtg ttgaatgaga agaaaacaaa aatcagaagt ttgcataata aattattaaa    600
tgcagctcaa gaacgagaaa aggacatcaa acaagaaggg gaaactgcaa tctgttctga    660
aatgactgct gaccgagatc cagtctatga tgagagtact gatgaggaaa gtgaaaacca    720
aactgatctc tctgggttgg cttcagctgc tgtaagtaaa gatgattcca ttatttcaag    780
tcttgatgtc actgatattg caccaagtag aaaaggaga cagcgaatgc aaagaaatct    840
tgggacagaa cctaaaatgg ctcctcagga gaatcagctt caagaaaagg aaaattctag    900
gcctgattct tcactacctg agacgtcgaa aaaggagcac atctcagctg aaaacatgtc    960
tttagaaact ctgagaaaca gcagcccaga agacctcttt gatgagattt a           1011
```

<210> SEQ ID NO 19
<211> LENGTH: 510
<212> TYPE: PRT
<213> ORGANISM: Homo sapiens

<400> SEQUENCE: 19

```
Met Asp Glu Lys Thr Lys Lys Ala Glu Glu Met Ala Leu Ser Leu Thr
1               5                   10                  15

Arg Ala Val Ala Gly Gly Asp Glu Gln Val Ala Met Lys Cys Ala Ile
            20                  25                  30

Trp Leu Ala Glu Gln Arg Val Pro Leu Ser Val Gln Leu Lys Pro Glu
        35                  40                  45

Val Ser Pro Thr Gln Asp Ile Arg Leu Trp Val Ser Val Glu Asp Ala
    50                  55                  60

Gln Met His Thr Val Thr Ile Trp Leu Thr Val Arg Pro Asp Met Thr
65                  70                  75                  80

Val Ala Ser Leu Lys Asp Met Val Phe Leu Asp Tyr Gly Phe Pro Pro
                85                  90                  95

Val Leu Gln Gln Trp Val Ile Gly Gln Arg Leu Ala Arg Asp Gln Glu
            100                 105                 110

Thr Leu His Ser His Gly Val Arg Gln Asn Gly Asp Ser Ala Tyr Leu
        115                 120                 125

Tyr Leu Leu Ser Ala Arg Asn Thr Ser Leu Asn Pro Gln Glu Leu Gln
    130                 135                 140

Arg Glu Arg Gln Leu Arg Met Leu Glu Asp Leu Gly Phe Lys Asp Leu
145                 150                 155                 160

Thr Leu Gln Pro Arg Gly Pro Leu Glu Pro Gly Pro Lys Pro Gly
                165                 170                 175

Val Pro Gln Glu Pro Gly Arg Gly Gln Pro Asp Ala Val Pro Glu Pro
            180                 185                 190

Pro Pro Val Gly Trp Gln Cys Pro Gly Cys Thr Phe Ile Asn Lys Pro
        195                 200                 205

Thr Arg Pro Gly Cys Glu Met Cys Cys Arg Ala Arg Pro Glu Ala Tyr
    210                 215                 220

Gln Val Pro Ala Ser Tyr Gln Pro Asp Glu Glu Arg Ala Arg Leu
225                 230                 235                 240

Ala Gly Glu Glu Glu Ala Leu Arg Gln Tyr Gln Gln Arg Lys Gln Gln
```

```
                    245                 250                 255
Gln Gln Glu Gly Asn Tyr Leu Gln His Val Gln Leu Asp Gln Arg Ser
            260                 265                 270

Leu Val Leu Asn Thr Glu Pro Ala Glu Cys Pro Val Cys Tyr Ser Val
        275                 280                 285

Leu Ala Pro Gly Glu Ala Val Val Leu Arg Glu Cys Leu His Thr Phe
    290                 295                 300

Cys Arg Glu Cys Leu Gln Gly Thr Ile Arg Asn Ser Gln Glu Ala Glu
305                 310                 315                 320

Val Ser Cys Pro Phe Ile Asp Asn Thr Tyr Ser Cys Ser Gly Lys Leu
            325                 330                 335

Leu Glu Arg Glu Ile Lys Ala Leu Leu Thr Pro Glu Asp Tyr Gln Arg
        340                 345                 350

Phe Leu Asp Leu Gly Ile Ser Ile Ala Glu Asn Arg Ser Ala Phe Ser
    355                 360                 365

Tyr His Cys Lys Thr Pro Asp Cys Lys Gly Trp Cys Phe Phe Glu Asp
370                 375                 380

Asp Val Asn Glu Phe Thr Cys Pro Val Cys Phe His Val Asn Cys Leu
385                 390                 395                 400

Leu Cys Lys Ala Ile His Glu Gln Met Asn Cys Lys Glu Tyr Gln Glu
            405                 410                 415

Asp Leu Ala Leu Arg Ala Gln Asn Asp Val Ala Ala Arg Gln Thr Thr
        420                 425                 430

Glu Met Leu Lys Val Met Leu Gln Gln Gly Glu Ala Met Arg Cys Pro
    435                 440                 445

Gln Cys Gln Ile Val Val Gln Lys Lys Asp Gly Cys Asp Trp Ile Arg
450                 455                 460

Cys Thr Val Cys His Thr Glu Ile Cys Trp Val Thr Lys Gly Pro Arg
465                 470                 475                 480

Trp Gly Pro Gly Gly Pro Gly Asp Thr Ser Gly Gly Cys Arg Cys Arg
            485                 490                 495

Val Asn Gly Ile Pro Cys His Pro Ser Cys Gln Asn Cys His
        500                 505                 510

<210> SEQ ID NO 20
<211> LENGTH: 1533
<212> TYPE: DNA
<213> ORGANISM: Homo sapiens

<400> SEQUENCE: 20
atggacgaga agaccaagaa agcagaggaa atggccctga gcctcacccg agcagtggcg    60
ggcggggatg aacaggtggc aatgaagtgt gccatctggc tggcagagca acgggtgccc   120
ctgagtgtgc aactgaagcc tgaggtctcc ccaacgcagg acatcaggct gtgggtgagc   180
gtggaggatg ctcagatgca caccgtcacc atctggctca cagtgcgccc tgatatgaca   240
gtggcgtctc tcaaggacat ggttttctg gactatggct tcccaccagt cttgcagcag   300
tgggtgattg gcagcggct ggcacgagac caggagaccc tgcactccca tggggtgcgg   360
cagaatgggg acagtgccta cctctatctg ctgtcagccc gcaacacctc cctcaaccct   420
caggagctgc agcgggagcg gcagctgcgg atgctggaag atctgggctt caaggacctc   480
acgctgcagc cgcggggccc tctggagcca ggccccccaa agcccggggt ccccaggaa    540 cccggacggg gcagccaga tgcagtgcct gagcccccac cggtgggctg gcagtgcccc   600
gggtgcacct tcatcaacaa gcccacgcgg cctggctgtg agatgtgctg ccgggcgcgc   660
```

```
cccgaggcct accaggtccc cgcctcatac cagcccgacg aggaggagcg agcgcgcctg    720
gcgggcgagg aggaggcgct gcgtcagtac cagcagcgga agcagcagca caggaggggg    780
aactacctgc agcacgtcca gctggaccag aggagcctgg tgctgaacac ggagcccgcc    840
gagtgccccg tgtgctactc ggtgctggcg cccggcgagg ccgtggtgct gcgtgagtgt    900
ctgcacacct tctgcaggga gtgcctgcag ggcaccatcc gcaacagcca ggaggcggag    960
gtctcctgcc ccttcattga caacacctac tcgtgctcgg caagctgct ggagagggag    1020 atcaaggcgc tcctgacccc tgaggattac cagcgatttc tagacctggg catctccatt    1080
gctgaaaacc gcagtgcctt cagctaccat tgcaagaccc cagattgcaa gggatggtgc    1140
ttctttgagg atgatgtcaa tgagttcacc tgccctgtgt gtttccacgt caactgcctg    1200
ctctgcaagg ccatccatga gcagatgaac tgcaaggagt atcaggagga cctggccctg    1260
cgggctcaga cgatgtggc tgcccggcag acgacagaga tgctgaaggt gatgctgcag    1320
cagggcgagg ccatgcgctg cccccagtgc cagatcgtgg tacagaagaa ggacggctgc    1380
gactggatcc gctgcaccgt ctgccacacc gagatctgct gggtcaccaa gggcccacgc    1440
tggggccctg ggggcccagg agacaccagc ggggctgcc gctgcagggt aaatgggatt    1500
ccttgccacc caagctgtca gaactgccac tga                                1533
```

<210> SEQ ID NO 21
<211> LENGTH: 500
<212> TYPE: PRT
<213> ORGANISM: Homo sapiens

<400> SEQUENCE: 21

Met Asp His Thr Glu Gly Ser Pro Ala Glu Pro Pro Ala His Ala
1               5                   10                  15

Pro Ser Pro Gly Lys Phe Gly Glu Arg Pro Pro Lys Arg Leu Thr
                20                  25                  30

Arg Glu Ala Met Arg Asn Tyr Leu Lys Glu Arg Gly Asp Gln Thr Val
                35                  40                  45

Leu Ile Leu His Ala Lys Val Ala Gln Lys Ser Tyr Gly Asn Glu Lys
50                  55                  60

Arg Phe Phe Cys Pro Pro Pro Cys Val Tyr Leu Met Gly Ser Gly Trp
65                  70                  75                  80

Lys Lys Lys Lys Glu Gln Met Glu Arg Asp Gly Cys Ser Glu Gln Glu
                85                  90                  95

Ser Gln Pro Cys Ala Phe Ile Gly Ile Gly Asn Ser Asp Gln Glu Met
                100                 105                 110

Gln Gln Leu Asn Leu Glu Gly Lys Asn Tyr Cys Thr Ala Lys Thr Leu
                115                 120                 125

Tyr Ile Ser Asp Ser Asp Lys Arg Lys His Phe Met Leu Ser Val Lys
130                 135                 140

Met Phe Tyr Gly Asn Ser Asp Asp Ile Gly Val Phe Leu Ser Lys Arg
145                 150                 155                 160

Ile Lys Val Ile Ser Lys Pro Ser Lys Lys Gln Ser Leu Lys Asn
                165                 170                 175

Ala Asp Leu Cys Ile Ala Ser Gly Thr Lys Val Ala Leu Phe Asn Arg
                180                 185                 190

Leu Arg Ser Gln Thr Val Ser Thr Arg Tyr Leu His Val Glu Gly Gly
                195                 200                 205

Asn Phe His Ala Ser Ser Gln Gln Trp Gly Ala Phe Phe Ile His Leu

```
                 210                 215                 220
Leu Asp Asp Asp Glu Ser Glu Gly Glu Glu Phe Thr Val Arg Asp Gly
225                 230                 235                 240

Tyr Ile His Tyr Gly Gln Thr Val Lys Leu Val Cys Ser Val Thr Gly
                245                 250                 255

Met Ala Leu Pro Arg Leu Ile Ile Arg Lys Val Asp Lys Gln Thr Ala
            260                 265                 270

Leu Leu Asp Ala Asp Asp Pro Val Ser Gln Leu His Lys Cys Ala Phe
        275                 280                 285

Tyr Leu Lys Asp Thr Glu Arg Met Tyr Leu Cys Leu Ser Gln Glu Arg
    290                 295                 300

Ile Ile Gln Phe Gln Ala Thr Pro Cys Pro Lys Glu Pro Asn Lys Glu
305                 310                 315                 320

Met Ile Asn Asp Gly Ala Ser Trp Thr Ile Ile Ser Thr Asp Lys Ala
                325                 330                 335

Glu Tyr Thr Phe Tyr Glu Gly Met Gly Pro Val Leu Ala Pro Val Thr
                340                 345                 350

Pro Val Pro Val Val Glu Ser Leu Gln Leu Asn Gly Gly Gly Asp Val
            355                 360                 365

Ala Met Leu Glu Leu Thr Gly Gln Asn Phe Thr Pro Asn Leu Arg Val
        370                 375                 380

Trp Phe Gly Asp Val Glu Ala Glu Thr Met Tyr Arg Cys Gly Glu Ser
385                 390                 395                 400

Met Leu Cys Val Val Pro Asp Ile Ser Ala Phe Arg Glu Gly Trp Arg
                405                 410                 415

Trp Val Arg Gln Pro Val Gln Val Pro Val Thr Leu Val Arg Asn Asp
                420                 425                 430

Gly Ile Ile Tyr Ser Thr Ser Leu Thr Phe Thr Tyr Thr Pro Glu Pro
            435                 440                 445

Gly Pro Arg Pro His Cys Ser Ala Ala Gly Ala Ile Leu Arg Ala Asn
        450                 455                 460

Ser Ser Gln Val Pro Pro Asn Glu Ser Asn Thr Asn Ser Glu Gly Ser
465                 470                 475                 480

Tyr Thr Asn Ala Ser Thr Asn Ser Thr Ser Val Thr Ser Ser Thr Ala
                485                 490                 495

Thr Val Val Ser
            500

<210> SEQ ID NO 22
<211> LENGTH: 1503
<212> TYPE: DNA
<213> ORGANISM: Homo sapiens

<400> SEQUENCE: 22
ccatggacca cacggagggc tcgcccgcgg aggagccgcc tgcgcatgct ccatcgcctg     60
ggaaatttgg tgagcggcct ccacctaaac gacttactag ggaagctatg cgaaattatt    120
taaaagagcg agggatcaa acagtactta ttcttcatgc aaaagttgca cagaagtcat    180
atggaaatga aaaaggtttt tttgcccac ctccttgtgt atatcttatg gcagtggat     240 ggaagaaaaa aaagaacaa atggaacgcg atggttgttc tgaacaagag tctcaaccgt    300
gtgcatttat tgggatagga atagtgacc aagaaatgca gcagctaaac ttggaaggaa    360
agaactattg cacagccaaa acattgtata tatctgactc agacaagcga aagcacttca    420
tgttgtctgt aaagatgttc tatggcaaca gtgatgacat tggtgtgttc ctcagcaagc    480
```

```
ggataaaagt catctccaaa ccttccaaaa agaagcagtc attgaaaaat gctgacttat      540
gcattgcctc aggaacaaag gtggctctgt ttaatcgact acgatcccag acagttagta      600
ccagatactt gcatgtagaa ggaggtaatt ttcatgccag ttcacagcag tggggagcct      660
tttttattca tctcttggat gatgatgaat cagaaggaga agaattcaca gtccgagatg      720
gctacatcca ttatggacaa acagtcaaac ttgtgtgctc agttactggc atggcactcc      780
caagattgat aattaggaaa gttgataagc agaccgcatt attggatgca gatgatcctg      840
tgtcacaact ccataaatgt gcattttacc ttaaggatac agaaagaatg tatttgtgcc      900
tttctcaaga aagaataatt caatttcagg ccactccatg tccaaaagaa ccaaataaag      960
agatgataaa tgatggcgct tcctggacaa tcattagcac agataaggca gagtatacat     1020
tttatgaggg aatgggccct gtccttgccc cagtcactcc tgtgcctgtg gtagagagcc     1080
ttcagttgaa tggcggtggg acgtagcaa tgcttgaact tacaggacag aatttcactc      1140
caaatttacg agtgtggttt ggggatgtag aagctgaaac tatgtacagg tgtggagaga     1200
gtatgctctg tgtcgtccca gacatttctg cattccgaga aggttggaga tgggtccggc     1260
aaccagtcca ggttccagta actttggtcc gaaatgatgg aatcatttat tccaccagcc     1320
ttacctttac ctacacacca gaaccagggc cgcggccaca ttgcagtgca gcaggagcaa     1380
tccttcgagc caattcaagc caggtgcccc ctaacgaatc aaacacaaac agcgagggaa     1440
gttacacaaa cgccagcaca aattcaacca gtgtcacatc atctacagcc acagtggtat     1500
cct                                                                   1503

<210> SEQ ID NO 23
<211> LENGTH: 1354
<212> TYPE: PRT
<213> ORGANISM: Homo sapiens

<400> SEQUENCE: 23

Met Ser Thr Gly Asp Ser Phe Glu Thr Arg Phe Glu Lys Met Asp Asn
1               5                   10                  15

Leu Leu Arg Asp Pro Lys Ser Glu Val Asn Ser Asp Cys Leu Leu Asp
            20                  25                  30

Gly Leu Asp Ala Leu Val Tyr Asp Leu Asp Phe Pro Ala Leu Arg Lys
        35                  40                  45

Asn Lys Asn Ile Asp Asn Phe Leu Ser Arg Tyr Lys Asp Thr Ile Asn
    50                  55                  60

Lys Ile Arg Asp Leu Arg Met Lys Ala Glu Asp Tyr Glu Val Val Lys
65                  70                  75                  80

Val Ile Gly Arg Gly Ala Phe Gly Glu Val Gln Leu Val Arg His Lys
                85                  90                  95

Ser Thr Arg Lys Val Tyr Ala Met Lys Leu Leu Ser Lys Phe Glu Met
            100                 105                 110

Ile Lys Arg Ser Asp Ser Ala Phe Phe Trp Glu Glu Arg Asp Ile Met
        115                 120                 125

Ala Phe Ala Asn Ser Pro Trp Val Val Gln Leu Phe Tyr Ala Phe Gln
    130                 135                 140

Asp Asp Arg Tyr Leu Tyr Met Val Met Glu Tyr Met Pro Gly Gly Asp
145                 150                 155                 160

Leu Val Asn Leu Met Ser Asn Tyr Asp Val Pro Glu Lys Trp Ala Arg
                165                 170                 175

Phe Tyr Thr Ala Glu Val Val Leu Ala Leu Asp Ala Ile His Ser Met
```

```
                180             185             190
Gly Phe Ile His Arg Asp Val Lys Pro Asp Asn Met Leu Leu Asp Lys
            195                 200                 205

Ser Gly His Leu Lys Leu Ala Asp Phe Gly Thr Cys Met Lys Met Asn
            210                 215                 220

Lys Glu Gly Met Val Arg Cys Asp Thr Ala Val Gly Thr Pro Asp Tyr
225                 230                 235                 240

Ile Ser Pro Glu Val Leu Lys Ser Gln Gly Gly Asp Gly Tyr Tyr Gly
                245                 250                 255

Arg Glu Cys Asp Trp Trp Ser Val Gly Val Phe Leu Tyr Glu Met Leu
                260                 265                 270

Val Gly Asp Thr Pro Phe Tyr Ala Asp Ser Leu Val Gly Thr Tyr Ser
            275                 280                 285

Lys Ile Met Asn His Lys Asn Ser Leu Thr Phe Pro Asp Asp Asn Asp
            290                 295                 300

Ile Ser Lys Glu Ala Lys Asn Leu Ile Cys Ala Phe Leu Thr Asp Arg
305                 310                 315                 320

Glu Val Arg Leu Gly Arg Asn Gly Val Glu Glu Ile Lys Arg His Leu
                325                 330                 335

Phe Phe Lys Asn Asp Gln Trp Ala Trp Glu Thr Leu Arg Asp Thr Val
                340                 345                 350

Ala Pro Val Val Pro Asp Leu Ser Ser Asp Ile Asp Thr Ser Asn Phe
            355                 360                 365

Asp Asp Leu Glu Glu Asp Lys Gly Glu Glu Glu Thr Phe Pro Ile Pro
            370                 375                 380

Lys Ala Phe Val Gly Asn Gln Leu Pro Phe Val Gly Phe Thr Tyr Tyr
385                 390                 395                 400

Ser Asn Arg Arg Tyr Leu Ser Ser Ala Asn Pro Asn Asp Asn Arg Thr
                405                 410                 415

Ser Ser Asn Ala Asp Lys Ser Leu Gln Glu Ser Leu Gln Lys Thr Ile
            420                 425                 430

Tyr Lys Leu Glu Glu Gln Leu His Asn Glu Met Gln Leu Lys Asp Glu
            435                 440                 445

Met Glu Gln Lys Cys Arg Thr Ser Asn Ile Lys Leu Asp Lys Ile Met
450                 455                 460

Lys Glu Leu Asp Glu Glu Gly Asn Gln Arg Arg Asn Leu Glu Ser Thr
465                 470                 475                 480

Val Ser Gln Ile Glu Lys Glu Lys Met Leu Leu Gln His Arg Ile Asn
                485                 490                 495

Glu Tyr Gln Arg Lys Ala Glu Gln Glu Asn Glu Lys Arg Arg Asn Val
                500                 505                 510

Glu Asn Glu Val Ser Thr Leu Lys Asp Gln Leu Glu Asp Leu Lys Lys
            515                 520                 525

Val Ser Gln Asn Ser Gln Leu Ala Asn Glu Lys Leu Ser Gln Leu Gln
            530                 535                 540

Lys Gln Leu Glu Glu Ala Asn Asp Leu Leu Arg Thr Glu Ser Asp Thr
545                 550                 555                 560

Ala Val Arg Leu Arg Lys Ser His Thr Glu Met Ser Lys Ser Ile Ser
                565                 570                 575

Gln Leu Glu Ser Leu Asn Arg Glu Leu Gln Glu Arg Asn Arg Ile Leu
                580                 585                 590

Glu Asn Ser Lys Ser Gln Thr Asp Lys Asp Tyr Tyr Gln Leu Gln Ala
            595                 600                 605
```

```
Ile Leu Glu Ala Glu Arg Arg Asp Arg Gly His Asp Ser Glu Met Ile
    610                 615                 620

Gly Asp Leu Gln Ala Arg Ile Thr Ser Leu Gln Glu Glu Val Lys His
625                 630                 635                 640

Leu Lys His Asn Leu Glu Lys Val Glu Gly Glu Arg Lys Glu Ala Gln
            645                 650                 655

Asp Met Leu Asn His Ser Glu Lys Glu Lys Asn Asn Leu Glu Ile Asp
                660                 665                 670

Leu Asn Tyr Lys Leu Lys Ser Leu Gln Gln Arg Leu Glu Gln Glu Val
            675                 680                 685

Asn Glu His Lys Val Thr Lys Ala Arg Leu Thr Asp Lys His Gln Ser
690                 695                 700

Ile Glu Ala Lys Ser Val Ala Met Cys Glu Met Glu Lys Lys Leu
705                 710                 715                 720

Lys Glu Glu Arg Glu Ala Arg Glu Lys Ala Glu Asn Arg Val Val Gln
                725                 730                 735

Ile Glu Lys Gln Cys Ser Met Leu Asp Val Asp Leu Lys Gln Ser Gln
                740                 745                 750

Gln Lys Leu Glu His Leu Thr Gly Asn Lys Glu Arg Met Glu Asp Glu
            755                 760                 765

Val Lys Asn Leu Thr Leu Gln Leu Glu Gln Glu Ser Asn Lys Arg Leu
770                 775                 780

Leu Leu Gln Asn Glu Leu Lys Thr Gln Ala Phe Glu Ala Asp Asn Leu
785                 790                 795                 800

Lys Gly Leu Glu Lys Gln Met Lys Gln Glu Ile Asn Thr Leu Leu Glu
                805                 810                 815

Ala Lys Arg Leu Leu Glu Phe Glu Leu Ala Gln Leu Thr Lys Gln Tyr
                820                 825                 830

Arg Gly Asn Glu Gly Gln Met Arg Glu Leu Gln Asp Gln Leu Glu Ala
            835                 840                 845

Glu Gln Tyr Phe Ser Thr Leu Tyr Lys Thr Gln Val Lys Glu Leu Lys
    850                 855                 860

Glu Glu Ile Glu Glu Lys Asn Arg Glu Asn Leu Lys Lys Ile Gln Glu
865                 870                 875                 880

Leu Gln Asn Glu Lys Glu Thr Leu Ala Thr Gln Leu Asp Leu Ala Glu
                885                 890                 895

Thr Lys Ala Glu Ser Glu Gln Leu Ala Arg Gly Leu Leu Glu Glu Gln
                900                 905                 910

Tyr Phe Glu Leu Thr Gln Glu Ser Lys Lys Ala Ala Ser Arg Asn Arg
    915                 920                 925

Gln Glu Ile Thr Asp Lys Asp His Thr Val Ser Arg Leu Glu Glu Ala
    930                 935                 940

Asn Ser Met Leu Thr Lys Asp Ile Glu Ile Leu Arg Arg Glu Asn Glu
945                 950                 955                 960

Glu Leu Thr Glu Lys Met Lys Lys Ala Glu Glu Tyr Lys Leu Glu
                965                 970                 975

Lys Glu Glu Glu Ile Ser Asn Leu Lys Ala Ala Phe Glu Lys Asn Ile
                980                 985                 990

Asn Thr Glu Arg Thr Leu Lys Thr Gln Ala Val Asn Lys Leu Ala Glu
            995                 1000                1005

Ile Met Asn Arg Lys Asp Phe Lys Ile Asp Arg Lys Lys Ala Asn Thr
            1010                1015                1020
```

Gln Asp Leu Arg Lys Lys Glu Lys Glu Asn Arg Lys Leu Gln Leu Glu
1025                1030                1035                1040

Leu Asn Gln Glu Arg Glu Lys Phe Asn Gln Met Val Val Lys His Gln
        1045                1050                1055

Lys Glu Leu Asn Asp Met Gln Ala Gln Leu Val Glu Glu Cys Ala His
            1060                1065                1070

Arg Asn Glu Leu Gln Met Gln Leu Ala Ser Lys Glu Ser Asp Ile Glu
        1075                1080                1085

Gln Leu Arg Ala Lys Leu Leu Asp Leu Ser Asp Ser Thr Ser Val Ala
    1090                1095                1100

Ser Phe Pro Ser Ala Asp Glu Thr Asp Gly Asn Leu Pro Glu Ser Arg
1105                1110                1115                1120

Ile Glu Gly Trp Leu Ser Val Pro Asn Arg Gly Asn Ile Lys Arg Tyr
            1125                1130                1135

Gly Trp Lys Lys Gln Tyr Val Val Ser Ser Lys Lys Ile Leu Phe
        1140                1145                1150

Tyr Asn Asp Glu Gln Asp Lys Glu Gln Ser Asn Pro Ser Met Val Leu
        1155                1160                1165

Asp Ile Asp Lys Leu Phe His Val Arg Pro Val Thr Gln Gly Asp Val
    1170                1175                1180

Tyr Arg Ala Glu Thr Glu Glu Ile Pro Lys Ile Phe Gln Ile Leu Tyr
1185                1190                1195                1200

Ala Asn Glu Gly Glu Cys Arg Lys Asp Val Glu Met Glu Pro Val Gln
            1205                1210                1215

Gln Ala Glu Lys Thr Asn Phe Gln Asn His Lys Gly His Glu Phe Ile
        1220                1225                1230

Pro Thr Leu Tyr His Phe Pro Ala Asn Cys Asp Ala Cys Ala Lys Pro
        1235                1240                1245

Leu Trp His Val Phe Lys Pro Pro Ala Leu Glu Cys Arg Arg Cys
    1250                1255                1260

His Val Lys Cys His Arg Asp His Leu Asp Lys Lys Glu Asp Leu Ile
1265                1270                1275                1280

Cys Pro Cys Lys Val Ser Tyr Asp Val Thr Ser Ala Arg Asp Met Leu
            1285                1290                1295

Leu Leu Ala Cys Ser Gln Asp Glu Gln Lys Lys Trp Val Thr His Leu
        1300                1305                1310

Val Lys Lys Ile Pro Lys Asn Pro Pro Ser Gly Phe Val Arg Ala Ser
        1315                1320                1325

Pro Arg Thr Leu Ser Thr Arg Ser Thr Ala Asn Gln Ser Phe Arg Lys
    1330                1335                1340

Val Val Lys Asn Thr Ser Gly Lys Thr Ser
1345                1350

<210> SEQ ID NO 24
<211> LENGTH: 4065
<212> TYPE: DNA
<213> ORGANISM: Homo sapiens

<400> SEQUENCE: 24
acatgtcgac tggggacagt tttgagactc gatttgaaaa aatggacaac ctgctgcggg     60
atcccaaatc ggaagtgaat tcggattgtt tgctggatgg attggatgct ttggtatatg    120
atttggattt tcctgcctta agaaaaaaca aaaatattga caacttttta agcagatata    180
aagacacaat aaataaaatc agagatttac gaatgaaagc tgaagattat gaagtagtga    240

```
aggtgattgg tagaggtgca tttggagaag ttcaattggt aaggcataaa tccaccagga    300
aggtatatgc tatgaagctt ctcagcaaat ttgaaatgat aaagagatct gattctgctt    360
ttttctggga agaaagggac atcatggctt ttgccaacag tccttgggtt gttcagcttt    420
tttatgcatt ccaagatgat cgttatctct acatggtgat ggaatacatg cctggtggag    480
atcttgtaaa cttaatgagc aactatgatg tgcctgaaaa atgggcacga ttctatactg    540
cagaagtagt tcttgcattg gatgcaatcc attccatggg ttttattcac agagatgtga    600
agcctgataa catgctgctg gataaatctg gacatttgaa gttagcagat tttggtactt    660
gtatgaagat gaataaggaa ggcatggtac gatgtgatac agcggttgga acacctgatt    720
atatttcccc tgaagtatta aaatcccaag gtggtgatgg ttattatgga agagaatgtg    780
actggtggtc ggttgggta tttttatacg aaatgcttgt aggtgataca ccttttatg    840 cagattcttt ggttggaact tacagtaaaa ttatgaacca taaaaattca cttacctttc    900
ctgatgataa tgacatatca aaagaagcaa aaaaccttat ttgtgccttc cttactgaca    960
gggaagtgag gttagggcga aatggtgtag aagaaatcaa acgacatctc ttcttcaaaa   1020
atgaccagtg ggcttgggaa acgctccgag acactgtagc accagttgta cccgatttaa   1080
gtagtgacat tgatactagt aattttgatg acttggaaga agataaagga gaggaagaaa   1140
cattccctat tcctaaagct ttcgttggca atcaactacc ttttgtagga tttacatatt   1200
atagcaatcg tagatactta tcttcagcaa atcctaatga taacagaact agctccaatg   1260
cagataaaag cttgcaggaa agtttgcaaa aaacaatcta taagctggaa gaacagctgc   1320
ataatgaaat gcagttaaaa gatgaaatgg agcagaagtg cagaacctca aacataaaac   1380
tagacaagat aatgaaagaa ttggatgaag agggaaatca aagaagaaat ctagaatcta   1440
cagtgtctca gattgagaag gagaaaatgt tgctacagca tagaattaat gagtaccaaa   1500
gaaaagctga acaggaaaat gagaagagaa gaaatgtaga aaatgaagtt tctacattaa   1560
aggatcagtt ggaagactta aagaaagtca gtcagaattc acagcttgct aatgagaagc   1620
tgtcccagtt acaaaagcag ctagaagaag ccaatgactt acttaggaca gaatcggaca   1680
cagctgtaag attgaggaag agtcacacag agatgagcaa gtcaattagt cagttagagt   1740
ccctgaacag agagttgcaa gagagaaatc gaatttaga gaattctaag tcacaaacag   1800
acaaagatta ttaccagctg caagctatat tagaagctga acgaagagac agaggtcatg   1860
attctgagat gattggagac cttcaagctc gaattacatc tttacaagag gaggtgaagc   1920
atctcaaaca taatctcgaa aaagtggaag gagaaagaaa agaggctcaa gacatgctta   1980
atcactcaga aaaggaaaag aataatttag agatagattt aaactacaaa cttaaatcat   2040
tacaacaacg gttagaacaa gaggtaaatg aacacaaagt aaccaaagct cgtttaactg   2100
acaaacatca atctattgaa gaggcaaagt ctgtggcaat gtgtgagatg gaaaaaaagc   2160
tgaaagaaga aagagaagct cgagagaagg ctgaaaatcg ggttgttcag attgagaaac   2220
agtgttccat gctagacgtt gatctgaagc aatctcagca gaaactagaa catttgactg   2280
gaaataaaga aaggatggag gatgaagtta agaatctaac cctgcaactg gagcaggaat   2340
caaataagcg gctgttgtta caaaatgaat tgaagactca agcatttgag gcagacaatt   2400
taaaaggttt agaaaagcag atgaaacagg aaataaatac tttattggaa gcaaagagat   2460
tattagaatt tgagttagct cagcttacga aacagtatag aggaaatgaa ggacagatgc   2520
gggagctaca agatcagctt gaagctgagc aatatttctc gacactttat aaacccagg   2580 taaaggaact taagaagaa attgaagaaa aaacagaga aatttaaag aaaatacagg   2640
```

-continued

```
aactacaaaa tgaaaaagaa actcttgcta ctcagttgga tctagcagaa acaaaagctg    2700
agtctgagca gttggcgcga ggccttctgg aagaacagta ttttgaattg acgcaagaaa    2760
gcaagaaagc tgcttcaaga aatagacaag agattacaga taaagatcac actgttagtc    2820
ggcttgaaga agcaaacagc atgctaacca agatattga aatattaaga agagagaatg    2880
aagagctaac agagaaaatg aagaaggcag aggaagaata taaactggag aaggaggagg    2940
agatcagtaa tcttaaggct gcctttgaaa agaatatcaa cactgaacga acccttaaaa    3000
cacaggctgt taacaaattg gcagaaataa tgaatcgaaa agattttaaa attgatagaa    3060
agaaagctaa tacacaagat ttgagaaaga agaaaaagga aaatcgaaag ctgcaactgg    3120
aactcaacca agaaagagag aaattcaacc agatggtagt gaaacatcag aaggaactga    3180
atgacatgca agcgcaattg gtagaagaat gtgcacatag gaatgagctt cagatgcagt    3240
tggccagcaa agagagtgat attgagcaat tgcgtgctaa acttttggac ctctcggatt    3300
ctacaagtgt tgctagtttt cctagtgctg atgaaactga tggtaacctc ccagagtcaa    3360
gaattgaagg ttggctttca gtaccaaata gaggaaatat caaacgatat ggctggaaga    3420
aacagtatgt tgtggtaagc agcaaaaaaa ttttgttcta taatgacgaa caagataagg    3480
agcaatccaa tccatctatg gtattggaca tagataaact gtttcacgtt agacctgtaa    3540
cccaaggaga tgtgtataga gctgaaactg aagaaattcc taaatattc cagatactat    3600 atgcaaatga aggtgaatgt agaaaagatg tagagatgga accagtacaa caagctgaaa    3660
aaactaattt ccaaaatcac aaaggccatg agtttattcc tacactctac cactttcctg    3720
ccaattgtga tgcctgtgcc aaacctctct ggcatgtttt taagccaccc cctgccctag    3780
agtgtcgaag atgccatgtt aagtgccaca gagatcactt agataagaaa gaggacttaa    3840
tttgtccatg taaagtaagt tatgatgtaa catcagcaag agatatgctg ctgttagcat    3900
gttctcagga tgaacaaaaa aaatgggtaa ctcatttagt aaagaaaatc cctaagaatc    3960
caccatctgg ttttgttcgt gcttcccctc gaacgctttc tacaagatcc actgcaaatc    4020
agtctttccg gaaagtggtc aaaaatacat ctggaaaaac tagtt                   4065
```

<210> SEQ ID NO 25  
<211> LENGTH: 1012  
<212> TYPE: PRT  
<213> ORGANISM: Homo sapiens

<400> SEQUENCE: 25

```
Met Thr Lys His Pro Pro Asn Arg Arg Gly Ile Ser Phe Glu Val Gly
1               5                   10                  15

Ala Gln Leu Glu Ala Arg Asp Arg Leu Lys Asn Trp Tyr Pro Ala His
                20                  25                  30

Ile Glu Asp Ile Asp Tyr Glu Glu Gly Lys Val Leu Ile His Phe Lys
            35                  40                  45

Arg Trp Asn His Arg Tyr Asp Glu Trp Phe Cys Trp Asp Ser Pro Tyr
        50                  55                  60

Leu Arg Pro Leu Glu Lys Ile Gln Leu Arg Lys Glu Gly Leu His Glu
65                  70                  75                  80

Glu Asp Gly Ser Ser Glu Phe Gln Ile Asn Glu Gln Val Leu Ala Cys
                85                  90                  95

Trp Ser Asp Cys Arg Phe Tyr Pro Ala Lys Val Thr Ala Val Asn Lys
            100                 105                 110

Asp Gly Thr Tyr Thr Val Lys Phe Tyr Asp Gly Val Val Gln Thr Val
```

-continued

```
            115                 120                 125
Lys His Ile His Val Lys Ala Phe Ser Lys Asp Gln Asn Ile Val Gly
    130                 135                 140

Asn Ala Arg Pro Lys Glu Thr Asp His Lys Ser Leu Ser Ser Ser Pro
145                 150                 155                 160

Asp Lys Arg Glu Lys Phe Lys Glu Gln Arg Lys Ala Thr Val Asn Val
                165                 170                 175

Lys Lys Asp Lys Glu Asp Lys Pro Leu Lys Thr Glu Lys Arg Pro Lys
                180                 185                 190

Gln Pro Asp Lys Glu Gly Lys Leu Ile Cys Ser Glu Lys Gly Lys Val
                195                 200                 205

Ser Glu Lys Ser Leu Pro Lys Asn Glu Lys Glu Asp Lys Glu Asn Ile
    210                 215                 220

Ser Glu Asn Asp Arg Glu Tyr Ser Gly Asp Ala Gln Val Asp Lys Lys
225                 230                 235                 240

Pro Glu Asn Asp Ile Val Lys Ser Pro Gln Glu Asn Leu Arg Glu Pro
                245                 250                 255

Lys Arg Lys Arg Gly Arg Pro Pro Ser Ile Ala Pro Thr Ala Val Asp
                260                 265                 270

Ser Asn Ser Gln Thr Leu Gln Pro Ile Thr Leu Glu Leu Arg Arg Arg
    275                 280                 285

Lys Ile Ser Lys Gly Cys Glu Val Pro Leu Lys Arg Pro Arg Leu Asp
    290                 295                 300

Lys Asn Ser Ser Gln Glu Lys Ser Lys Asn Tyr Ser Glu Asn Thr Asp
305                 310                 315                 320

Lys Asp Leu Ser Arg Arg Ser Ser Arg Leu Ser Thr Asn Gly Thr
                325                 330                 335

His Glu Ile Leu Asp Pro Asp Leu Val Val Ser Asp Leu Val Asp Thr
                340                 345                 350

Asp Pro Leu Gln Asp Thr Leu Ser Ser Thr Lys Glu Ser Glu Glu Gly
                355                 360                 365

Gln Leu Lys Ser Ala Leu Glu Ala Gly Gln Val Ser Ser Ala Leu Thr
    370                 375                 380

Cys His Ser Phe Gly Asp Gly Ser Gly Ala Ala Gly Leu Glu Leu Asn
385                 390                 395                 400

Cys Pro Ser Met Gly Glu Asn Thr Met Lys Thr Glu Pro Thr Ser Pro
                405                 410                 415

Leu Val Glu Leu Gln Glu Ile Ser Thr Val Glu Val Thr Asn Thr Phe
                420                 425                 430

Lys Lys Thr Asp Asp Phe Gly Ser Ser Asn Ala Pro Ala Val Asp Leu
                435                 440                 445

Asp His Lys Phe Arg Cys Lys Val Val Asp Cys Leu Lys Phe Phe Arg
                450                 455                 460

Lys Ala Lys Leu Leu His Tyr His Met Lys Tyr Phe His Gly Met Glu
465                 470                 475                 480

Lys Ser Leu Glu Pro Glu Glu Ser Pro Gly Lys Arg His Val Gln Thr
                485                 490                 495

Arg Gly Pro Ser Ala Ser Asp Lys Pro Ser Gln Glu Thr Leu Thr Arg
                500                 505                 510

Lys Arg Val Ser Ala Ser Ser Pro Thr Thr Lys Asp Lys Glu Lys Asn
                515                 520                 525

Lys Glu Lys Lys Phe Lys Glu Phe Val Arg Val Lys Pro Lys Lys Lys
                530                 535                 540
```

```
Lys Lys Lys Lys Lys Lys Thr Lys Pro Glu Cys Pro Cys Ser Glu Glu
545                 550                 555                 560

Ile Ser Asp Thr Ser Gln Glu Pro Ser Pro Pro Lys Ala Phe Ala Val
                565                 570                 575

Thr Arg Cys Gly Ser Ser His Lys Pro Gly Val His Met Ser Pro Gln
            580                 585                 590

Leu His Gly Pro Glu Ser Gly His His Lys Gly Lys Val Lys Ala Leu
        595                 600                 605

Glu Glu Asp Asn Leu Ser Glu Ser Ser Ser Glu Ser Phe Leu Trp Ser
    610                 615                 620

Asp Asp Glu Tyr Gly Gln Asp Val Asp Val Thr Thr Asn Pro Asp Glu
625                 630                 635                 640

Glu Leu Asp Gly Asp Asp Arg Tyr Asp Phe Glu Val Val Arg Cys Ile
                645                 650                 655

Cys Glu Val Gln Glu Glu Asn Asp Phe Met Ile Gln Cys Glu Glu Cys
                660                 665                 670

Gln Cys Trp Gln His Gly Val Cys Met Gly Leu Leu Glu Glu Asn Val
        675                 680                 685

Pro Glu Lys Tyr Thr Cys Tyr Val Cys Gln Asp Pro Pro Gly Gln Arg
    690                 695                 700

Pro Gly Phe Lys Tyr Trp Tyr Asp Lys Glu Trp Leu Ser Arg Gly His
705                 710                 715                 720

Met His Gly Leu Ala Phe Leu Glu Glu Asn Tyr Ser His Gln Asn Ala
                725                 730                 735

Lys Lys Ile Val Ala Thr His Gln Leu Leu Gly Asp Val Gln Arg Val
                740                 745                 750

Ile Glu Val Leu His Gly Leu Gln Leu Lys Met Ser Ile Leu Gln Ser
            755                 760                 765

Arg Glu His Pro Asp Leu Pro Leu Trp Cys Gln Pro Trp Lys Gln His
    770                 775                 780

Ser Gly Glu Gly Arg Ser His Phe Arg Asn Ile Pro Val Thr Asp Thr
785                 790                 795                 800

Arg Ser Lys Glu Glu Ala Pro Ser Tyr Arg Thr Leu Asn Gly Ala Val
                805                 810                 815

Glu Lys Pro Arg Pro Leu Ala Leu Pro Leu Pro Arg Ser Val Glu Glu
            820                 825                 830

Ser Tyr Ile Thr Ser Glu His Cys Tyr Gln Lys Pro Arg Ala Tyr Tyr
        835                 840                 845

Pro Ala Val Glu Gln Lys Leu Val Leu Glu Thr Arg Gly Ser Ala Leu
    850                 855                 860

Asp Asp Ala Val Asn Pro Leu His Glu Asn Gly Asp Asp Ser Leu Ser
865                 870                 875                 880

Pro Arg Leu Gly Trp Pro Leu Asp Gln Asp Arg Ser Lys Gly Asp Ser
                885                 890                 895

Asp Pro Lys Pro Gly Ser Pro Lys Val Lys Glu Tyr Val Ser Lys Lys
                900                 905                 910

Ala Leu Pro Glu Glu Ala Pro Ala Arg Lys Leu Leu Asp Arg Gly Gly
            915                 920                 925

Glu Gly Leu Leu Ser Ser Gln His Gln Trp Gln Phe Asn Leu Leu Thr
        930                 935                 940

His Val Glu Ser Leu Gln Asp Glu Val Thr His Arg Met Asp Ser Ile
945                 950                 955                 960
```

```
Glu Lys Glu Leu Asp Val Leu Glu Ser Trp Leu Asp Tyr Thr Gly Glu
            965                 970                 975

Leu Glu Pro Pro Glu Pro Leu Ala Arg Leu Pro Gln Leu Lys His Cys
        980                 985                 990

Ile Lys Gln Leu Leu Met Asp Leu Gly Lys Val Gln Gln Ile Ala Leu
        995                 1000                1005

Cys Cys Ser Thr
        1010

<210> SEQ ID NO 26
<211> LENGTH: 3039
<212> TYPE: DNA
<213> ORGANISM: Homo sapiens

<400> SEQUENCE: 26
```

| | | | | | |
|---|---|---|---|---|---|
| atgacaaagc | atccacctaa | cagacgagga | atcagctttg | aagtgggagc | ccagttggaa | 60 |
| gcccgggacc | gtttaaaaaa | ctggtatcca | gctcacatag | aagacattga | ctacgaggaa | 120 |
| ggaaaagtac | tcatccattt | caagcgttgg | aaccatcgtt | atgatgagtg | gttctgctgg | 180 |
| gacagtcctt | atttacgccc | tttagagaaa | atacagctga | ggaaagaggg | cttgcatgaa | 240 |
| gaggatggat | cttctgaatt | tcaaataaat | gagcaggtcc | ttgcttgctg | gtctgattgt | 300 |
| cgttttttacc | cggccaaagt | cactgctgtt | aacaaggatg | gtacttacac | tgtgaaattt | 360 |
| tatgatggag | tagttcagac | tgtcaaacat | attcatgtca | aagcttttc | caagatcag | 420 |
| aatattgtgg | gtaatgctag | gcctaaagaa | acagatcaca | aaagtctttc | atcatctcct | 480 |
| gataaacgag | agaagtttaa | agaacagaga | aaagcaacag | tgaatgtgaa | gaagacaaa | 540 |
| gaagataaac | ccttaaagac | agaaaagcga | cccaagcagc | ctgataaaga | aggaaagtta | 600 |
| atctgttctg | aaaaggggaa | agtgtcagag | aaagtcttc | caagaacga | gaggaagac | 660 |
| aaggaaaaca | tttccgaaaa | tgacagagag | tattctggag | atgcccaagt | ggataagaaa | 720 |
| cctgaaaatg | acattgtgaa | gagtccacaa | gaaaacttga | gggaacccaa | agaaaacga | 780 |
| ggcagacccc | cttccatagc | tcctactgct | gtggattcaa | actctcaaac | tttgcaacca | 840 |
| ataacattgg | aactgagaag | aaggaaaata | tcaaaaggat | gtgaagtccc | attaaaacgt | 900 |
| cctcggcttg | acaaaaattc | atcccaggaa | aagtcaaaaa | actactcgga | aaacactgac | 960 |
| aaagacttat | cgaggagacg | ttcctccagg | ctgtccacta | atgggaccca | tgagatccta | 1020 |
| gatcctgact | tggttgtatc | agatttggtt | gatacggatc | cttgtcaaga | cacgttgtct | 1080 |
| agtaccaagg | aatctgaaga | aggtcagttg | aagtctgctt | tggaagctgg | ccaggtctca | 1140 |
| tctgcactga | cttgccactc | ctttgggat | ggatccgggg | ctgcaggctt | ggagttgaac | 1200 |
| tgcccatcaa | tggagaaaaa | cacgatgaaa | acagaaccga | cttctcccct | tgtggaatta | 1260 |
| caagagattt | cgactgtgga | agtaacaaat | acttttaaga | aaacagatga | ttttgggtca | 1320 |
| tctaatgcac | cagctgtcga | cctagaccat | aagtttagat | gcaaagttgt | ggactgttta | 1380 |
| aaatttttcc | gcaaagccaa | actgttgcac | tatcacatga | gtatttccca | tggaatggag | 1440 |
| aagtcactgg | agccagaaga | gagcccggga | aagaggcatg | tccaaaccag | ggccccttca | 1500 |
| gcttcagaca | agcccagcca | ggagaccctg | accaggaagc | gggtctctgc | cagttcccca | 1560 |
| actacaaaag | acaaggaaaa | gaataaagag | aagaaattca | aggagtttgt | gagagtgaag | 1620 |
| ccaaagaaga | aaagaaaaa | gaaaagaaa | accaaacctg | aatgcccctg | cagtgaggag | 1680 |
| atcagtgaca | cctcccagga | accttctcca | cccaaggcat | tgctgttac | caggtgtggg | 1740 |
| tcctcacaca | agccagggt | ccatatgagc | ccgcagcttc | atggcccaga | atctggacac | 1800 |

```
cacaaaggga aagtgaaagc attggaggag gataatttga gtgagtcctc ttctgagagc    1860
tttctctgga gtgatgatga gtatggccaa gatgtggatg tgaccaccaa cccagatgag    1920
gaacttgatg gggatgaccg ctatgacttc gaggtggtcc gctgcatctg tgaggtccag    1980
gaggaaaatg acttcatgat tcagtgtgaa gagtgccagt gctggcagca tggggtctgc    2040
atgggattac tggaagaaaa tgtgcccgag aaatacacct gttatgtttg ccaagaccct    2100
ccaggtcaga ggcctggctt caagtactgg tatgacaagg agtggctgag caggggacat    2160
atgcatggcc tggcatttct agaagagaac tactcccatc agaatgccaa gaagatcgtg    2220
gccacccacc agcttcttgg tgatgtgcag agagtgattg aggttctgca tggcctgcag    2280
ctcaagatga gcatcttgca aagccgggag catcctgatc tgccgctgtg gtgccagcct    2340
tggaaacagc actcagggga ggggagatct catttcagaa acatccctgt cactgacacc    2400
aggagcaagg aggaagctcc aagctataga actttgaacg gggcagtgga gaagcccagg    2460
cccctggccc tgcccctgcc gcgttctgtg gaggaatcct atatcaccag tgagcattgc    2520
taccagaagc ccgcgcccta ttaccctgcc gtggagcaga agctggtggt ggagacgagg    2580
ggctctgccc tcgacgatgc ggtcaacccc ctccatgaga acggcgatga ttccctttcc    2640
ccgcgcctgg gctggcctct agaccaagac aggagcaagg gggacagtga ccccaaaccc    2700
ggctccccaa aggtgaagga atatgtctcc aaaaaggccc taccagaaga agcccctgct    2760
cggaagctgc tggacagagg tggagagggg ctgctgagct cccagcacca gtggcagttt    2820
aacctgctga cccatgtgga atctcttcag gatgaagtta cgcacaggat ggactccatt    2880
gagaaggagt tggatgtgtt ggagagctgg ctggactaca ctggggaact ggagccccct    2940
gagccgctgg ccaggcttcc gcagctcaag cattgtatca agcagctgct gatggacctg    3000
ggcaaggtgc agcagatcgc cctctgctgc tcaacatga                          3039
```

<210> SEQ ID NO 27
<211> LENGTH: 1483
<212> TYPE: PRT
<213> ORGANISM: Homo sapiens

<400> SEQUENCE: 27

```
Met Ala Pro Leu Leu Gly Arg Lys Pro Phe Pro Leu Val Lys Pro Leu
1               5                   10                  15

Pro Gly Glu Glu Pro Leu Phe Thr Ile Pro His Thr Gln Glu Ala Phe
                20                  25                  30

Arg Thr Arg Glu Glu Tyr Glu Ala Arg Leu Glu Arg Tyr Ser Glu Arg
            35                  40                  45

Ile Trp Thr Cys Lys Ser Thr Gly Ser Ser Gln Leu Thr His Lys Glu
        50                  55                  60

Ala Trp Glu Glu Glu Gln Val Ala Glu Leu Leu Lys Glu Glu Phe
65                  70                  75                  80

Pro Ala Trp Tyr Glu Lys Leu Val Leu Glu Met Val His His Asn Thr
                85                  90                  95

Ala Ser Leu Glu Lys Leu Val Asp Thr Ala Trp Leu Glu Ile Met Thr
                100                 105                 110

Lys Tyr Ala Val Gly Glu Glu Cys Asp Phe Glu Val Gly Lys Glu Lys
            115                 120                 125

Met Leu Lys Val Lys Ile Val Lys Ile His Pro Leu Glu Lys Val Asp
        130                 135                 140

Glu Glu Ala Thr Glu Lys Lys Ser Asp Gly Ala Cys Asp Ser Pro Ser
```

```
            145                 150                 155                 160
Ser Asp Lys Glu Asn Ser Ser Gln Ile Ala Gln Asp His Gln Lys Lys
                    165                 170                 175
Glu Thr Val Val Lys Glu Asp Glu Gly Arg Glu Ser Ile Asn Asp
                180                 185                 190
Arg Ala Arg Arg Ser Pro Arg Lys Leu Pro Thr Ser Leu Lys Lys Gly
            195                 200                 205
Glu Arg Lys Trp Ala Pro Pro Lys Phe Leu Pro His Lys Tyr Asp Val
        210                 215                 220
Lys Leu Gln Asn Glu Asp Lys Ile Ile Ser Asn Val Pro Ala Asp Ser
225                 230                 235                 240
Leu Ile Arg Thr Glu Arg Pro Pro Asn Lys Glu Ile Val Arg Tyr Phe
                245                 250                 255
Ile Arg His Asn Ala Leu Arg Ala Gly Thr Gly Glu Asn Ala Pro Trp
            260                 265                 270
Val Val Glu Asp Glu Leu Val Lys Lys Tyr Ser Leu Pro Ser Lys Phe
        275                 280                 285
Ser Asp Phe Leu Leu Asp Pro Tyr Lys Tyr Met Thr Leu Asn Pro Ser
    290                 295                 300
Thr Lys Arg Lys Asn Thr Gly Ser Pro Asp Arg Lys Pro Ser Lys Lys
305                 310                 315                 320
Ser Lys Thr Asp Asn Ser Ser Leu Ser Ser Pro Leu Asn Pro Lys Leu
                325                 330                 335
Trp Cys His Val His Leu Lys Lys Ser Leu Ser Gly Ser Pro Leu Lys
            340                 345                 350
Val Lys Asn Ser Lys Asn Ser Lys Ser Pro Glu Glu His Leu Glu Glu
        355                 360                 365
Met Met Lys Met Met Ser Pro Asn Lys Leu His Thr Asn Phe His Ile
    370                 375                 380
Pro Lys Lys Gly Pro Pro Ala Lys Lys Pro Gly Lys His Ser Asp Lys
385                 390                 395                 400
Pro Leu Lys Ala Lys Gly Arg Ser Lys Gly Ile Leu Asn Gly Gln Lys
                405                 410                 415
Ser Thr Gly Asn Ser Lys Ser Pro Lys Lys Gly Leu Lys Thr Pro Lys
            420                 425                 430
Thr Lys Met Lys Gln Met Thr Leu Leu Asp Met Ala Lys Gly Thr Gln
        435                 440                 445
Lys Met Thr Arg Ala Pro Arg Asn Ser Gly Gly Thr Pro Arg Thr Ser
    450                 455                 460
Ser Lys Pro His Lys His Leu Pro Pro Ala Ala Leu His Leu Ile Ala
465                 470                 475                 480
Tyr Tyr Lys Glu Asn Lys Asp Arg Glu Asp Lys Arg Ser Ala Leu Ser
                485                 490                 495
Cys Val Ile Ser Lys Thr Ala Arg Leu Leu Ser Ser Glu Asp Arg Ala
            500                 505                 510
Arg Leu Pro Glu Glu Leu Arg Ser Leu Val Gln Lys Arg Tyr Glu Leu
        515                 520                 525
Leu Glu His Lys Lys Arg Trp Ala Ser Met Ser Glu Glu Gln Arg Lys
    530                 535                 540
Glu Tyr Leu Lys Lys Arg Glu Leu Lys Lys Leu Lys Glu
545                 550                 555                 560
Lys Ala Lys Glu Arg Arg Glu Lys Glu Met Leu Glu Arg Leu Glu Lys
                565                 570                 575
```

```
Gln Lys Arg Tyr Glu Asp Gln Glu Leu Thr Gly Lys Asn Leu Pro Ala
            580                 585                 590

Phe Arg Leu Val Asp Thr Pro Glu Gly Leu Pro Asn Thr Leu Phe Gly
        595                 600                 605

Asp Val Ala Met Val Val Glu Phe Leu Ser Cys Tyr Ser Gly Leu Leu
    610                 615                 620

Leu Pro Asp Ala Gln Tyr Pro Ile Thr Ala Val Ser Leu Met Glu Ala
625                 630                 635                 640

Leu Ser Ala Asp Lys Gly Gly Phe Leu Tyr Leu Asn Arg Val Leu Val
            645                 650                 655

Ile Leu Leu Gln Thr Leu Leu Gln Asp Glu Ile Ala Glu Asp Tyr Gly
            660                 665                 670

Glu Leu Gly Met Lys Leu Ser Glu Ile Pro Leu Thr Leu His Ser Val
        675                 680                 685

Ser Glu Leu Val Arg Leu Cys Leu Arg Arg Ser Asp Val Gln Glu Glu
    690                 695                 700

Ser Glu Gly Ser Asp Thr Asp Asn Lys Asp Ser Ala Ala Phe Glu
705                 710                 715                 720

Asp Asn Glu Val Gln Asp Glu Phe Leu Glu Lys Leu Glu Thr Ser Glu
            725                 730                 735

Phe Phe Glu Leu Thr Ser Glu Glu Lys Leu Gln Ile Leu Thr Ala Leu
        740                 745                 750

Cys His Arg Ile Leu Met Thr Tyr Ser Val Gln Asp His Met Glu Thr
    755                 760                 765

Arg Gln Gln Met Ser Ala Glu Leu Trp Lys Glu Arg Leu Ala Val Leu
        770                 775                 780

Lys Glu Glu Asn Asp Lys Lys Arg Ala Glu Lys Gln Lys Arg Lys Glu
785                 790                 795                 800

Met Glu Ala Lys Asn Lys Glu Asn Gly Lys Val Glu Asn Gly Leu Gly
            805                 810                 815

Lys Thr Asp Arg Lys Lys Glu Ile Val Lys Phe Glu Pro Gln Val Asp
            820                 825                 830

Thr Glu Ala Glu Asp Met Ile Ser Ala Val Lys Ser Arg Arg Leu Leu
        835                 840                 845

Ala Ile Gln Ala Lys Lys Glu Arg Glu Ile Gln Glu Arg Glu Met Lys
850                 855                 860

Val Lys Leu Glu Arg Gln Ala Glu Glu Glu Arg Ile Arg Lys His Lys
865                 870                 875                 880

Ala Ala Ala Glu Lys Ala Phe Gln Glu Gly Ile Ala Lys Ala Lys Leu
            885                 890                 895

Val Met Arg Arg Thr Pro Ile Gly Thr Asp Arg Asn His Asn Arg Tyr
        900                 905                 910

Trp Leu Phe Ser Asp Glu Val Pro Gly Leu Phe Ile Glu Lys Gly Trp
    915                 920                 925

Val His Asp Ser Ile Asp Tyr Arg Phe Asn His His Cys Lys Asp His
    930                 935                 940

Thr Val Ser Gly Asp Glu Asp Tyr Cys Pro Arg Ser Lys Lys Ala Asn
945                 950                 955                 960

Leu Gly Lys Asn Ala Ser Met Asn Thr Gln His Gly Thr Ala Thr Glu
            965                 970                 975

Val Ala Val Glu Thr Thr Thr Pro Lys Gln Gly Gln Asn Leu Trp Phe
        980                 985                 990
```

-continued

Leu Cys Asp Ser Gln Lys Glu Leu Asp Glu Leu Leu Asn Cys Leu His
        995                 1000                1005

Pro Gln Gly Ile Arg Glu Ser Gln Leu Lys Glu Arg Leu Glu Lys Arg
    1010                1015                1020

Tyr Gln Asp Ile Ile His Ser Ile His Leu Ala Arg Lys Pro Asn Leu
1025                1030                1035                1040

Gly Leu Lys Ser Cys Asp Gly Asn Gln Glu Leu Leu Asn Phe Leu Arg
        1045                1050                1055

Ser Asp Leu Ile Glu Val Ala Thr Arg Leu Gln Lys Gly Gly Leu Gly
        1060                1065                1070

Tyr Val Glu Glu Thr Ser Glu Phe Glu Ala Arg Val Ile Ser Leu Glu
        1075                1080                1085

Lys Leu Lys Asp Phe Gly Glu Cys Val Ile Ala Leu Gln Ala Ser Val
    1090                1095                1100

Ile Lys Lys Phe Leu Gln Gly Phe Met Ala Pro Lys Gln Lys Arg Arg
1105                1110                1115                1120

Lys Leu Gln Ser Glu Asp Ser Ala Lys Thr Glu Glu Val Asp Glu Glu
        1125                1130                1135

Lys Lys Met Val Glu Glu Ala Lys Val Ala Ser Ala Leu Glu Lys Trp
        1140                1145                1150

Lys Thr Ala Ile Arg Glu Ala Gln Thr Phe Ser Arg Met His Val Leu
        1155                1160                1165

Leu Gly Met Leu Asp Ala Cys Ile Lys Trp Asp Met Ser Ala Glu Asn
        1170                1175                1180

Ala Arg Cys Lys Val Cys Arg Lys Lys Gly Glu Asp Asp Lys Leu Ile
1185                1190                1195                1200

Leu Cys Asp Glu Cys Asn Lys Ala Phe His Leu Phe Cys Leu Arg Pro
        1205                1210                1215

Ala Leu Tyr Glu Val Pro Asp Gly Glu Trp Gln Cys Pro Ala Cys Gln
        1220                1225                1230

Pro Ala Thr Ala Arg Arg Asn Ser Arg Gly Arg Asn Tyr Thr Glu Glu
        1235                1240                1245

Ser Ala Ser Glu Asp Ser Glu Asp Asp Glu Ser Asp Glu Glu Glu Glu
        1250                1255                1260

Glu Glu Glu Glu Glu Glu Glu Glu Asp Tyr Glu Val Ala Gly Leu
1265                1270                1275                1280

Arg Leu Arg Pro Arg Lys Thr Ile Arg Gly Lys His Ser Val Ile Pro
        1285                1290                1295

Pro Ala Ala Arg Ser Gly Arg Arg Pro Gly Lys Lys Pro His Ser Thr
        1300                1305                1310

Arg Arg Ser Gln Pro Lys Ala Pro Pro Val Asp Asp Ala Glu Val Asp
        1315                1320                1325

Glu Leu Val Leu Gln Thr Lys Arg Ser Ser Arg Arg Gln Ser Leu Glu
        1330                1335                1340

Leu Gln Lys Cys Glu Glu Ile Leu His Lys Ile Val Lys Tyr Arg Phe
1345                1350                1355                1360

Ser Trp Pro Phe Arg Glu Pro Val Thr Arg Asp Glu Ala Glu Asp Tyr
        1365                1370                1375

Tyr Asp Val Ile Thr His Pro Met Asp Phe Gln Thr Val Gln Asn Lys
        1380                1385                1390

Cys Ser Cys Gly Ser Tyr Arg Ser Val Gln Glu Phe Leu Thr Asp Met
        1395                1400                1405

Lys Gln Val Phe Thr Asn Ala Glu Val Tyr Asn Cys Arg Gly Ser His

```
         1410              1415              1420
Val Leu Ser Cys Met Val Lys Thr Glu Gln Cys Leu Val Ala Leu Leu
1425              1430              1435              1440

His Lys His Leu Pro Gly His Pro Tyr Val Arg Arg Lys Arg Lys Lys
         1445              1450              1455

Phe Pro Asp Arg Leu Ala Glu Asp Glu Gly Asp Ser Glu Pro Glu Ala
         1460              1465              1470

Val Gly Gln Ser Arg Gly Arg Arg Gln Lys Lys
         1475              1480

<210> SEQ ID NO 28
<211> LENGTH: 4452
<212> TYPE: DNA
<213> ORGANISM: Homo sapiens

<400> SEQUENCE: 28
atggcgccgc tcctgggccg caagcccttc ccgctggtga agccgttgcc cggagaggag      60
ccgctcttca ccatcccgca cactcaggag gccttccgca cccggaagag gtatgaagcc     120
cgcttggaaa ggtacagtga gcgcatttgg acgtgcaaga gtactggaag cagtcagcta     180
acacacaagg aagcctggga ggaagaacag gaagttgctg agcttttgaa ggaggagttt     240
cctgcctggt atgagaagct tgttctggaa atggttcacc ataacacagc ctccttagag     300
aagttagtag atactgcttg gttggagatc atgaccaaat atgctgtggg agaagagtgt     360
gacttcgagg ttgggaagga gaaaatgctc aaggtgaaga ttgtgaagat tcatcctttg     420
gagaaagtgg atgaagaggc cactgagaag aaatctgatg tgcctgtgaa ttctccatca     480
agtgacaaag agaactccag tcagattgct caggaccatc agaagaagga gacagttgtg     540
aaagaggatg aaggaaggag agagagtatt aatgacagag cacgtagatc gccacgaaaa     600
cttcctactt cattaaaaaa aggagaaagg aaatgggctc ctccaaaatt tctgcctcac     660
aaatatgatg tgaaactaca aaatgaagat aagatcatca gtaacgtgcc agcagacagc     720
ttgattcgta cagagcgccc accaaataag gagatagttc gatactttat acggcataat     780
gcattacgag ctggtactgg tgaaaatgca ccttgggtcg tagaagatga attggtgaag     840
aaatactctc tgcccagcaa gttcagtgac ttttacttg atccatacaa gtatatgact     900
ctcaaccctt ctactaagag gaagaatact ggatccccag acaggaagcc tcaaagaaaa     960
tccaagacag acaactcttc tcttagttca ccactaaatc ctaagttatg gtgtcacgta    1020
cacttgaaga agtcattgag tggctcgcca ctcaaagtga agaactcaaa gaattccaaa    1080
tctcctgaag aacatctaga agaaatgatg aagatgatgt cgcccaataa gctgcacact    1140
aactttcaca ttcctaaaaa aggcccacct gccaagaaac cagggaagca cagtgacaag    1200
ccttttgaagg caaagggcag aagcaaaggc atcctgaatg acagaaatcc acagggaat    1260
tccaaatctc ccaaaaaagg actgaagact cctaaaacca aaatgaagca gatgactttg    1320
ttggatatgg ccaaaggcac gcagaagatg acacgagccc cacggaattc tgggggtaca    1380
cctaggacct ctagtaaacc tcataaacat ctgcctcctg cagccctaca cctcattgca    1440
tactacaaag aaaacaaaga cagggaggac aagaggagcg ccctgtcctg tgttatctcc    1500
aaaacagctc gtcttctctc tagtgaagat agagctcgtc tcccagaaga attgcgaagt    1560
cttgttcaaa aacgctatga acttctagag cacaaaaaga ggtgggcttc tatgtctgaa    1620
gaacaacgga agaatatttt gaaaagaaa cgggaggagc tgaaaaagaa gttgaaggaa    1680
aaagccaaag aacgaagaga aaagaaatg cttgagagat tagaaaaaca gaagcggtat    1740
```

```
gaggaccaag agttaactgg caaaaacctt ccagcattca gattggtgga tacccctgaa    1800
gggctgccca acacgctgtt tggggatgtg gccatggtgg tggaattctt gagctgttat    1860
tctgggctac ttttaccaga tgctcagtat cctattactg ctgtgtccct tatggaagcc    1920
ttgagtgcag ataagggtgg ctttttatac cttaacaggg tgttggtcat cctcttacag    1980
accctcctac aagatgagat agcagaagac tatggtgaat tgggaatgaa gctgtcggaa    2040
atccccttga ctctgcattc tgtttcagag ctggtgcggc tctgcttgcg cagatctgat    2100
gttcaggagg aaagcgaggg ctcagacaca gatgacaata agattcagc tgcatttgag    2160 gataatgagg tacaagatga gttcctagaa aagctggaga cctctgaatt ttttgagctg    2220
acgtcagagg agaagctaca gatcttgaca gcactgtgcc accggatcct catgacatac    2280
tcagtgcaag accacatgga gaccagacag cagatgtctg cagagttgtg aaggaacgg    2340 cttgctgtgt tgaaggaaga aaatgataag aagagagcag agaaacagaa acggaaagaa    2400
atggaagcca aaaataaaga aatggaaaa gttgagaatg ggttaggcaa aactgatagg    2460
aaaaaagaaa ttgtgaagtt tgagccccaa gtagatacag aagctgaaga catgattagt    2520
gctgtgaaga gcagaaggtt gcttgccatt caagctaaga aggaacggga atccaggaa    2580 agagaaatga aagtgaaact ggaacgccaa gctgaagaag aacgaatacg gaagcacaaa    2640
gcagctgctg agaaagcttt ccaggaaggg attgccaagg ccaaactagt catgcgcagg    2700
actcctattg gcacagatcg aaaccataat agatactggc tcttctcaga tgaagttcca    2760
ggattattca ttgaaaaagg ctgggtacat gacagcattg actaccgatt caaccatcac    2820
tgcaaagacc acacagtctc tggtgatgag gattactgtc ctcgcagtaa gaaagcaaac    2880
ttaggtaaaa atgcaagcat gaacacacaa catggaacag caacagaagt tgctgtagag    2940
acaaccacac ccaaacaagg acagaaccta tggtttttat gtgatagtca aaaggagctg    3000
gatgagttgc taaactgtct tcaccctcag ggaataagag aaagtcaact taagagaga    3060 ctagagaaga ggtaccagga cattattcac tctattcatc tagcacggaa gccaaatttg    3120
ggtctaaaat cttgtgatgg caaccaggag ctttttaaact tccttcgtag tgatctcatt    3180
gaagttgcaa caaggttaca aaaaggagga cttggatatg tggaagaaac atcagaattt    3240
gaagcccggg tcatttcatt agagaaattg aaggattttg tgagtgtgt gattgccctt    3300 caggccagtg tcataaagaa atttctccaa ggcttcatgg ctcccaagca aaagagaaga    3360
aaactccaaa gtgaagattc agcaaaaact gaggaagtgg atgaagagaa gaaaatggta    3420
gaggaagcaa aggttgcatc tgcactggag aaatggaaga cagcaatccg ggaagctcag    3480
actttctcca ggatgcacgt gctgcttggg atgcttgatg cctgtatcaa gtgggatatg    3540
tccgcagaaa atgctaggtg caaagtttgt cgaaagaaag tgaggatga caaattgatc    3600 ttgtgtgatg agtgtaataa agccttccac ctgtttttgtc tgaggccggc cctctatgaa    3660
gtaccagatg tgagtggca gtgcccagct tgccagcccg ctactgccag cgcaactcc    3720 cgtggcagga actatactga agagtctgct tctgaggaca gtgaagatga tgagagtgat    3780
gaagaggagg aggaggaaga agaggaggag gaggaagaag attatgaggt ggctggttg    3840 cgattgagac ctcgaaagac catccggggc aagcacagcg tcatccccc tgcagcaagg    3900 tcaggccggc gcccgggtaa gaagccacac tctaccagga ggtctcagcc caaggcacca    3960
cctgtggatg atgctgaggt ggatgagctg gtgcttcaga ccaagcggag ctcccggagg    4020
caaagcctgg agctgcagaa gtgtgaagag atcctccaca gatcgtgaa gtaccgcttc    4080
```

-continued

```
agctggccct tcagggagcc tgtgaccaga gatgaggccg aggactacta tgatgtgatc    4140
acgcacccca tggactttca gacagtgcag aacaaatgtt cctgtgggag ctaccgctct    4200
gtgcaggagt ttcttactga catgaagcaa gtgtttacca atgctgaggt ttacaactgc    4260
cgtggcagcc atgtgctaag ctgcatggtg aagacagaac agtgtctagt ggctctgttg    4320
cataaacacc ttcctggcca cccatatgtc cgcaggaagc gcaagaagtt tcctgatagg    4380
cttgctgaag atgaaggga cagtgagcca gaggccgttg acagtccag gggacgaaga    4440 cagaagaagt ag                                                        4452
```

<210> SEQ ID NO 29
<211> LENGTH: 621
<212> TYPE: PRT
<213> ORGANISM: Homo sapiens

<400> SEQUENCE: 29

```
Met Leu Leu Leu Pro Ser Ala Ala Asp Gly Arg Gly Thr Ala Ile Thr
1               5                   10                  15

His Ala Leu Thr Ser Ala Ser Thr Leu Cys Gln Val Glu Pro Val Gly
            20                  25                  30

Arg Trp Phe Glu Ala Phe Val Lys Arg Arg Asn Arg Asn Ala Ser Ala
        35                  40                  45

Ser Phe Gln Glu Leu Glu Asp Lys Lys Glu Leu Ser Glu Glu Ser Glu
    50                  55                  60

Asp Glu Glu Leu Gln Leu Glu Phe Pro Met Leu Lys Thr Leu Asp
65                  70                  75                  80

Pro Lys Asp Trp Lys Asn Gln Asp His Tyr Ala Val Leu Gly Leu Gly
                85                  90                  95

His Val Arg Tyr Lys Ala Thr Gln Arg Gln Ile Lys Ala Ala His Lys
            100                 105                 110

Ala Met Val Leu Lys His His Pro Asp Lys Arg Lys Ala Ala Gly Glu
        115                 120                 125

Pro Ile Lys Glu Gly Asp Asn Asp Tyr Phe Thr Cys Ile Thr Lys Ala
    130                 135                 140

Tyr Glu Met Leu Ser Asp Pro Val Lys Arg Arg Ala Phe Asn Ser Val
145                 150                 155                 160

Asp Pro Thr Phe Asp Asn Ser Val Pro Ser Lys Ser Glu Ala Lys Asp
                165                 170                 175

Asn Phe Phe Glu Val Phe Thr Pro Val Phe Glu Arg Asn Ser Arg Trp
            180                 185                 190

Ser Asn Lys Lys Asn Val Pro Lys Leu Gly Asp Met Asn Ser Ser Phe
        195                 200                 205

Glu Asp Val Asp Ile Phe Tyr Ser Phe Trp Tyr Asn Phe Asp Ser Trp
    210                 215                 220

Arg Glu Phe Ser Tyr Leu Asp Glu Glu Lys Glu Lys Ala Glu Cys
225                 230                 235                 240

Arg Asp Glu Arg Arg Trp Ile Glu Lys Gln Asn Arg Ala Thr Arg Ala
                245                 250                 255

Gln Arg Lys Lys Glu Glu Met Asn Arg Ile Arg Thr Leu Val Asp Asn
            260                 265                 270

Ala Tyr Ser Cys Asp Pro Arg Ile Lys Lys Phe Lys Glu Glu Glu Lys
        275                 280                 285

Ala Lys Lys Glu Ala Glu Lys Lys Ala Lys Ala Glu Ala Lys Arg Lys
    290                 295                 300
```

| | | | | | | | | | | | |
|---|---|---|---|---|---|---|---|---|---|---|---|
|Glu|Gln|Glu|Ala|Lys|Glu|Lys|Gln|Arg|Gln|Ala|Glu|Leu|Glu|Ala|Ala|
|305| | | |310| | | |315| | | |320|

Arg Leu Ala Lys Glu Lys Glu Glu Glu Val Arg Gln Gln Ala Leu
                       325                    330                 335

*(Formatted as amino acid sequence listing)*

```
Glu Gln Glu Ala Lys Glu Lys Gln Arg Gln Ala Glu Leu Glu Ala Ala
305                 310                 315                 320

Arg Leu Ala Lys Glu Lys Glu Glu Glu Val Arg Gln Gln Ala Leu
            325                 330                 335

Leu Ala Lys Lys Glu Lys Asp Ile Gln Lys Ala Ile Lys Lys Glu
        340                 345                 350

Arg Gln Lys Leu Arg Asn Ser Cys Lys Thr Trp Asn His Phe Ser Asp
            355                 360                 365

Asn Glu Ala Glu Arg Val Lys Met Met Glu Glu Val Glu Lys Leu Cys
370                 375                 380

Asp Arg Leu Glu Leu Ala Ser Leu Gln Cys Leu Asn Glu Thr Leu Thr
385                 390                 395                 400

Ser Cys Thr Lys Glu Val Gly Lys Ala Ala Leu Glu Lys Gln Ile Glu
                405                 410                 415

Glu Ile Asn Glu Gln Ile Arg Lys Glu Lys Glu Ala Glu Ala Arg
            420                 425                 430

Met Arg Gln Ala Ser Lys Asn Thr Glu Lys Ser Thr Gly Gly Gly
            435                 440                 445

Asn Gly Ser Lys Asn Trp Ser Glu Asp Asp Leu Gln Leu Leu Ile Lys
450                 455                 460

Ala Val Asn Leu Phe Pro Ala Gly Thr Asn Ser Arg Trp Glu Val Ile
465                 470                 475                 480

Ala Asn Tyr Met Asn Ile His Ser Ser Ser Gly Val Lys Arg Thr Ala
                485                 490                 495

Lys Asp Val Ile Gly Lys Ala Lys Ser Leu Gln Lys Leu Asp Pro His
                500                 505                 510

Gln Lys Asp Asp Ile Asn Lys Lys Ala Phe Asp Lys Phe Lys Lys Glu
            515                 520                 525

His Gly Val Val Pro Gln Ala Asp Asn Ala Thr Pro Ser Glu Arg Phe
            530                 535                 540

Glu Gly Pro Tyr Thr Asp Phe Thr Pro Trp Thr Glu Glu Gln Lys
545                 550                 555                 560

Leu Leu Glu Gln Ala Leu Lys Thr Tyr Pro Val Asn Thr Pro Glu Arg
                565                 570                 575

Trp Glu Lys Ile Ala Glu Ala Val Pro Gly Arg Thr Lys Lys Asp Cys
            580                 585                 590

Met Lys Arg Tyr Lys Glu Leu Val Glu Met Val Lys Ala Lys Lys Ala
            595                 600                 605

Ala Gln Glu Gln Val Leu Asn Ala Ser Arg Ala Lys Lys
610                 615                 620
```

<210> SEQ ID NO 30
<211> LENGTH: 1866
<212> TYPE: DNA
<213> ORGANISM: Homo sapiens

<400> SEQUENCE: 30

```
tcatgctgct tctgccaagc gccgcggacg gccggggcac cgccatcacc cacgctctga    60
cctctgcctc tacactctgt caagttgaac ctgtgggaag atggtttgaa gcttttgtta   120
agaggagaaa cagaaatgct tctgcctctt ttcaggaact ggaggataag aaagagttat   180
ccgaggaatc agaagatgaa gaattgcagt tggaagagtt tcccatgctg aaaacacttg   240
atcccaaaga ctggaagaac caagatcatt atgcagttct tggacttggc catgtgagat   300
acaaggctac acagagacag atcaaagcag ctcataaagc aatggtttta aaacatcacc   360
```

| | | |
|---|---|---|
| cagacaaacg gaaagcagct ggtgaaccaa taaaagaagg agataatgac tacttcactt | 420 | |
| gcataactaa agcttatgaa atgttatctg atccagtgaa aagacgagca tttaacagtg | 480 | |
| tagatcctac ttttgataac tcagttcctt ctaaaagtga agcaaaggat aatttcttcg | 540 | |
| aagtgtttac cccagtgttt gaaggaatt ccagatggtc aaataaaaaa aatgttccta | 600 | |
| aacttggtga tatgaattca tcatttgaag atgtagatat attttattct ttctggtata | 660 | |
| attttgattc ttggagagaa ttttcttatt tagatgaaga agaaaaagaa aaagcagaat | 720 | |
| gtcgtgatga gaggagatgg attgaaaagc agaacagagc aacaagagca caagaaaaaa | 780 | |
| aagaagaaat gaacagaata agaacattag ttgacaatgc atacagctgt gatccaagga | 840 | |
| taaaaaagtt caaggaagaa gaaaaagcca agaaagaagc agaaaagaaa gcaaaagcag | 900 | |
| aagctaaacg gaaggagcaa gaagctaaag aaaaacaaag acaagctgaa ttagaagctg | 960 | |
| ctcggttagc taaggagaaa gaagaggagg aagtcagaca gcaagcattg ctggcaaaga | 1020 | |
| aggaaaaaga tatccagaaa aaagccatta gaaggaaag gcaaaaactt cgaaactcat | 1080 | |
| gcaagacctg gaatcatttt tctgataatg aggcagagcg ggttaaaatg atggaagaag | 1140 | |
| tggaaaaact ttgtgatcgg cttgaactgg caagcttaca gtgcttgaat gaaacactca | 1200 | |
| catcatgcac aaaagaagta ggaaaggctg ctttggaaaa acagatagaa gaaataaatg | 1260 | |
| agcaaatcag aaaagagaaa gaggaagctg aggctcgtat gcgacaagca tctaagaaca | 1320 | |
| cagagaaatc aactggtgga ggtggaaatg gaagtaaaaa ttggtcagaa gatgatctac | 1380 | |
| aattactaat taaagctgtg aatctgttcc ctgctggaac aaattcaaga tgggaagtta | 1440 | |
| ttgctaatta catgaacata cattcttcct ctggagtcaa aagaactgcc aaagatgtta | 1500 | |
| ttggcaaagc aaagagtctc caaaaacttg accctcatca aaagatgac ataaataaaa | 1560 | |
| aggcatttga taagttcaaa aaagaacatg gagtggtacc tcaagcagac aacgcaacgc | 1620 | |
| cttcagaacg atttgaaggt ccatatacag acttcacccc ttggacaaca gaagaacaga | 1680 | |
| agcttttgga acaagctttg aaaacatacc cagtaaatac acctgaaaga tgggaaaaaa | 1740 | |
| tagcagaagc ggtgcctggc aggacaaaga aggactgcat gaaacgatac aaggaacttg | 1800 | |
| tcgagatggt aaaagcaaag aaagctgctc aagaacaagt gctgaatgca agtagagcca | 1860 | |
| agaaat | 1866 | |

<210> SEQ ID NO 31
<211> LENGTH: 380
<212> TYPE: PRT
<213> ORGANISM: Homo sapiens

<400> SEQUENCE: 31

Met Gly Ala Ala Ala Glu Ala Pro Leu Arg Leu Pro Ala Ala Pro
1               5                   10                  15

Pro Leu Ala Phe Cys Cys Tyr Thr Ser Val Leu Leu Phe Ala Phe
            20                  25                  30

Ser Leu Pro Gly Ser Arg Ala Ser Asn Gln Pro Gly Gly Gly Gly
        35                  40                  45

Gly Ser Gly Gly Asp Cys Pro Gly Gly Lys Lys Ser Ile Asn Cys
    50                  55                  60

Ser Glu Leu Asn Val Arg Glu Ser Asp Val Arg Val Cys Asp Glu Ser
65                  70                  75                  80

Ser Cys Lys Tyr Gly Gly Val Cys Lys Glu Asp Gly Asp Gly Leu Lys
                85                  90                  95

| | | | | | | | | | | | |
|---|---|---|---|---|---|---|---|---|---|---|---|
|Cys|Ala|Cys|Gln|Phe|Gln|Cys|His|Thr|Asn|Tyr|Ile|Pro|Val|Cys|Gly|
| | | |100| | | |105| | | |110| | | | |

Cys Ala Cys Gln Phe Gln Cys His Thr Asn Tyr Ile Pro Val Cys Gly
                    100                    105                    110

Ser Asn Gly Asp Thr Tyr Gln Asn Glu Cys Phe Leu Arg Arg Ala Ala
           115                   120                   125

Cys Lys His Gln Lys Glu Ile Thr Val Ile Ala Arg Gly Pro Cys Tyr
   130                   135                   140

Ser Asp Asn Gly Ser Gly Ser Gly Glu Gly Glu Glu Gly Ser Gly
145               150                   155                   160

Ala Glu Val His Arg Lys His Ser Lys Cys Gly Pro Cys Lys Tyr Lys
             165                   170                   175

Ala Glu Cys Asp Glu Asp Ala Glu Asn Val Gly Cys Val Cys Asn Ile
         180                     185                   190

Asp Cys Ser Gly Tyr Ser Phe Asn Pro Val Cys Ala Ser Asp Gly Ser
             195                   200                 205

Ser Tyr Asn Asn Pro Cys Phe Val Arg Glu Ala Ser Cys Ile Lys Gln
         210                     215                   220

Glu Gln Ile Asp Ile Arg His Leu Gly His Cys Thr Asp Thr Asp Asp
225               230                   235                   240

Thr Ser Leu Leu Gly Lys Lys Asp Asp Gly Leu Gln Tyr Arg Pro Asp
               245                  250               255

Val Lys Asp Ala Ser Asp Gln Arg Glu Asp Val Tyr Ile Gly Asn His
         260                     265               270

Met Pro Cys Pro Glu Asn Leu Asn Gly Tyr Cys Ile His Gly Lys Cys
        275                   280                 285

Glu Phe Ile Tyr Ser Thr Gln Lys Ala Ser Cys Arg Cys Glu Ser Gly
290               295                   300

Tyr Thr Gly Gln His Cys Glu Lys Thr Asp Phe Ser Ile Leu Tyr Val
305               310                   315               320

Val Pro Ser Arg Gln Lys Leu Thr His Val Leu Ile Ala Ala Ile Ile
             325                   330               335

Gly Ala Val Gln Ile Ala Ile Ile Val Ala Ile Val Met Cys Ile Thr
             340                   345               350

Arg Lys Cys Pro Lys Asn Asn Arg Gly Arg Arg Gln Lys Gln Asn Leu
         355                     360               365

Gly His Phe Thr Ser Asp Thr Ser Ser Arg Met Val
         370                     375               380

<210> SEQ ID NO 32
<211> LENGTH: 1143
<212> TYPE: DNA
<213> ORGANISM: Homo sapiens

<400> SEQUENCE: 32

```
atgggcgccg cagccgctga ggcgccgctc cggctgcctg ccgcgcctcc gctcgccttc    60
tgctgctaca cgtcggtgct tctgctcttc gccttctctc tgcccgggag ccgcgcgtcc   120
aaccagcccc cgggtggtgg cggcggcagc ggcgggactg tcccggcgg caaaggcaag    180 agcatcaact gctcagaatt aaatgtgagg gagtctgacg taagagtttg tgatgagtca    240
tcatgtaaat atggaggagt ctgtaaagaa gatgagatg gtttgaaatg tgcatgccaa    300
tttcagtgcc atacaaatta tattcctgtc tgtggatcaa atggggacac ttatcaaaat    360
gaatgctttc tcagaagggc tgcttgtaag caccagaaag agataacagt aatagcaaga    420
ggaccatgct actctgataa tggatctgga tctggagaag agaagagga agggtcaggg    480 gcagaagttc acagaaaaca ctccaagtgt ggaccctgca aatataaagc tgagtgtgat    540
```

```
gaagatgcag aaaatgttgg gtgtgtatgt aatatagatt gcagtggata cagttttaat    600
cctgtgtgtg cttctgatgg gagttcctat aacaatccct gttttgttcg agaagcatct    660
tgtataaagc aagaacaaat tgatataagg catcttggtc attgcacaga tacagatgac    720
actagtttgt tgggaagaa agatgatgga ctacaatatc gaccagatgt gaaagatgct    780
agtgatcaaa gagaagatgt ttatattgga aaccacatgc cttgccctga aaacctcaat    840
ggttactgca tccatggaaa atgtgaattc atctattcta ctcagaaggc ttcttgtaga    900
tgtgaatctg gctacactgg acagcactgt gaaaagacag actttagtat tctctatgta    960
gtgccaagta ggcaaaagct cactcatgtt cttattgcag caattattgg agctgtacag   1020
attgccatca tagtagcaat tgtaatgtgc ataacaagaa aatgccccaa aaacaataga   1080
ggacgtcgac agaagcaaaa cctaggtcat tttacttcag atacgtcatc cagaatggtt   1140
taa                                                                 1143

<210> SEQ ID NO 33
<211> LENGTH: 185
<212> TYPE: PRT
<213> ORGANISM: Homo sapiens

<400> SEQUENCE: 33

Met Gly Lys Lys Gln Asn Lys Lys Val Glu Glu Val Leu Glu Glu
1               5                   10                  15

Glu Glu Glu Glu Tyr Val Val Glu Lys Val Leu Asp Arg Arg Val Val
                20                  25                  30

Lys Gly Lys Val Glu Tyr Leu Leu Lys Trp Lys Gly Phe Ser Asp Glu
            35                  40                  45

Asp Asn Thr Trp Glu Pro Glu Glu Asn Leu Asp Cys Pro Asp Leu Ile
        50                  55                  60

Ala Glu Phe Leu Gln Ser Gln Lys Thr Ala His Glu Thr Asp Lys Ser
65                  70                  75                  80

Glu Gly Gly Lys Arg Lys Ala Asp Ser Asp Ser Glu Asp Lys Gly Glu
                85                  90                  95

Glu Ser Lys Pro Lys Lys Lys Glu Glu Ser Glu Lys Pro Arg Gly
            100                 105                 110

Phe Ala Arg Gly Leu Glu Pro Glu Arg Ile Ile Gly Ala Thr Asp Ser
        115                 120                 125

Ser Gly Glu Leu Met Phe Leu Met Lys Trp Lys Asn Ser Asp Glu Ala
    130                 135                 140

Asp Leu Val Pro Ala Lys Glu Ala Asn Val Lys Cys Pro Gln Val Val
145                 150                 155                 160

Ile Ser Phe Tyr Glu Glu Arg Leu Thr Trp His Ser Tyr Pro Ser Glu
                165                 170                 175

Asp Asp Asp Lys Lys Asp Asp Lys Asn
            180                 185

<210> SEQ ID NO 34
<211> LENGTH: 558
<212> TYPE: DNA
<213> ORGANISM: Homo sapiens

<400> SEQUENCE: 34
atggggaaaa acaaaacaa gaagaaagtg gaggaggtgc tagaagagga ggaagaggaa     60
tatgtggtgg aaaaagttct cgaccgtcga gtggtaaagg gcaaagtgga gtacctccta   120
```

```
aagtggaagg gattctcaga tgaggacaac acatgggagc agaagagaa cctggattgc    180 cccgacctca ttgctgagtt tctgcagtca cagaaaacag cacatgagac agataaatca    240
gagggaggca agcgcaaagc tgattctgat tctgaagata agggagagga gagcaaacca    300
aagaagaaga aagaagagtc agaaaagcca cgaggctttg ctcgaggttt ggagccggag    360
cggattattg gagctacaga ctccagtgga gagctcatgt tcctgatgaa atggaaaaac    420
tctgatgagg ctgacctggt ccctgccaag gaagccaatg tcaagtgccc acaggttgtc    480
atatccttct atgaggaaag gctgacgtgg cattcctacc cctcggagga tgatgacaaa    540
aaagatgaca agaactaa                                                  558
```

```
<210> SEQ ID NO 35
<211> LENGTH: 257
<212> TYPE: PRT
<213> ORGANISM: Homo sapiens

<400> SEQUENCE: 35

Met Val Ala Glu Lys Glu Thr Leu Ser Leu Asn Lys Cys Pro Asp Lys
1               5                   10                  15

Met Pro Lys Arg Thr Lys Leu Leu Ala Gln Gln Pro Leu Pro Val His
            20                  25                  30

Gln Pro His Ser Leu Val Ser Glu Gly Phe Thr Val Lys Ala Met Met
        35                  40                  45

Lys Asn Ser Val Val Arg Gly Pro Pro Ala Ala Gly Ala Phe Lys Glu
    50                  55                  60

Arg Pro Thr Lys Pro Thr Ala Phe Arg Lys Phe Tyr Glu Arg Gly Asp
65                  70                  75                  80

Phe Pro Ile Ala Leu Glu His Asp Ser Lys Gly Asn Lys Ile Ala Trp
                85                  90                  95

Lys Val Glu Ile Glu Lys Leu Asp Tyr His His Tyr Leu Pro Leu Phe
            100                 105                 110

Phe Asp Gly Leu Cys Glu Met Thr Phe Pro Tyr Glu Phe Phe Ala Arg
        115                 120                 125

Gln Gly Ile His Asp Met Leu Glu His Gly Gly Asn Lys Ile Leu Pro
    130                 135                 140

Val Leu Pro Gln Leu Ile Ile Pro Ile Lys Asn Ala Leu Asn Leu Arg
145                 150                 155                 160

Asn Arg Gln Val Ile Cys Val Thr Leu Lys Val Leu Gln His Leu Val
                165                 170                 175

Val Ser Ala Glu Met Val Gly Lys Thr Leu Val Pro Tyr Tyr Arg Gln
            180                 185                 190

Ile Leu Pro Val Leu Asn Ile Phe Lys Asn Met Asn Val Asn Ser Gly
        195                 200                 205

Asp Gly Ile Asp Tyr Ser Gln Gln Lys Arg Glu Asn Ile Gly Asp Leu
    210                 215                 220

Ile Gln Glu Thr Leu Glu Ala Phe Glu Arg Tyr Gly Gly Glu Asn Ala
225                 230                 235                 240

Phe Ile Asn Ile Lys Tyr Val Val Pro Thr Tyr Glu Ser Cys Leu Leu
                245                 250                 255

Asn

<210> SEQ ID NO 36
<211> LENGTH: 774
<212> TYPE: DNA
<213> ORGANISM: Homo sapiens
```

```
<400> SEQUENCE: 36
atggtggcag aaaaagagac cctgagctta aacaaatgcc cagacaagat gccgaagagg    60
accaagctgc tggcacaaca gccgctcccg gtgcaccagc ctcactctct ggtttctgag   120
ggtttcacag tcaaagccat gatgaaaaac tcagtcgtga gaggccctcc agctgcaggg   180
gcatttaaag aaagaccaac caagcccaca gcatttcgaa aattctatga gcgaggtgac   240
ttcccaattg cccttgagca tgattcgaaa ggaaacaaaa tcgcctggaa ggtagaaatt   300
gagaagctgg attaccatca ttatctgcct ctgtttttg atgggctttg tgaaatgaca    360
tttccctatg agtttttgc tcggcaagga atccacgaca tgctggaaca cggtgggaac    420
aagatcctac ctgtccttcc acagctcatt atcccgataa aaaatgcctt gaacctccga   480
aaccgacagg tcatctgtgt cactctcaag gtcctccagc atctggttgt gtcagctgag   540
atggtgggca agaccttggt gccttattac cgtcaaatcc tccctgtcct gaacatcttt   600
aagaatatga atgtgaactc cggagacggc attgactaca gccagcagaa gagggagaac   660
attggggact tgatccagga gacactggag gccttcgagc gctacggagg agaaaatgcc   720
tttatcaaca ttaagtacgt ggtcccaacc tacgagtctt gcttgctaaa ctaa          774
```

POLYPEPTIDE MARKER FOR DIAGNOSIS OF ARTERIOSCLEROSIS, METHOD FOR DETECTION OF ARTERIOSCLEROSIS BY USING THE MAKER OR THE LIKE, AND KIT FOR DIAGNOSIS OF ARTERIOSCLEROSIS

TECHNICAL FIELD

The present invention relates to polypeptide markers for diagnosing arteriosclerosis, gene markers for diagnosing arteriosclerosis, antibodies, probes for detecting an arteriosclerosis marker gene, a DNA microarray or a DNA chip for detecting the arteriosclerosis marker genes, a method for detecting arteriosclerosis, and a kit for diagnosing arteriosclerosis.

Priority is claimed on Japanese Patent Application No. 2008-209210, filed Aug. 15, 2008, the content of which is incorporated herein by reference.

BACKGROUND ART

Arteriosclerosis is a disease frequently found in aorta, coronary arteries, cerebral arteries, and carotid arteries, being a main cause of myocardial infarction and cerebral infarction. At present, the presence of atherosclerosis is said to be crucial for the ground of the onset of ischemic organ diseases such as ischemic heart disease and cerebrovascular disorder, which are top leading causes of death. Arteriosclerotic lesions are pathomorphologically characterized by: fatty streaks which are subendothelial accumulations of cholesterol ester-storing cells (foam cells); and as an advanced stage thereof, invasions of smooth muscle cells, macrophages, T cells, and the like; as well as fibrous plaques showing cellular necrosis and fat accumulation. The site with fat accumulation is structurally fragile, where plaques are ruptured, triggered by a hemodynamic force, and thereby a thrombus is rapidly formed by reactions of tissue factors and blood coagulation factors. It has been elucidated that the occurrence of thrombotic blockage by the rupture of plaques in a coronary artery is closely associated with the onset of so-called acute coronary syndromes such as acute myocardial infarction, unstable angina pectoris, and cardiac sudden death (Non-Patent Document 1)

Arteriosclerosis is gradually developed without subjective symptoms, and all of the sudden, myocardial infarction, cerebral infarction, or angina pectoris occurs. Thus, early stage detection is required. So far, ultrasonography, angiography, imaging tests with MRI (magnetic resonance imaging devices) or such a device, electrocardiography, electroencephalography, and the like have been widely carried out for the diagnosis of arteriosclerotic lesions. However, methods by means of biochemical examination have been demanded so that diagnosis of an arteriosclerotic lesion can achieve an early detection.

In the diagnosis of an arteriosclerotic lesion by means of biochemical examination, there has been known measurements of arteriosclerosis-induced lipoproteins which are associated with lipid accumulation in the vascular wall such as LDL (low density lipoprotein), lipoprotein (Lp-α), remnant lipoprotein, and oxidized LDL in serum or plasma. In particular, measurement of arteriosclerosis-associated substances in blood are attracting attention in recent years. It is reported that measurement of an inflammatory substance: CRP (C-reactive protein), and measurement of the chlamydia antibody titer are useful.

As for the diagnosis method of an arteriosclerotic lesion by means of such measurement of an arteriosclerosis-induced lipoprotein, the following methods are known. For example, regarding the LDL measurement, the followings have been proposed: measurement of neutrophil, monocyte/macrophage or like inflammatory cell-originated components such as lactoferrin, myeloperoxidase, granulocytic elastase in serum or plasma, forming a complex with the oxidized LDL existing in the serum or the plasma, by an immunological means (Patent Document 1); use of an immunoassay method with a fused polypeptide comprising the extracellular region of an oxidized LDL receptor and a part of the heavy chain constant region of an immunoglobulin (Patent Document 2); use of an anti-human aldehyde-modified α1 antitrypsin monoclonal antibody capable of specifically recognizing oxidized LDL-α1 antitrypsin complex (Patent Documents 3 and 4); measurement of the degree of oxidative denaturation of LDL in plasma by an oxidizing agent comprising an azo compound such as V-70 (Patent Document 5); and the like.

Furthermore, regarding the diagnosis of an arteriosclerotic lesion by means of lipoprotein measurement, the followings have been disclosed: measurement of remnant lipoprotein (RLP) in denatured blood (Patent Document 6); diagnosis of rheumatoid or arteriosclerotic lesions through detection of the expression of the human cartilage GP39-L polypeptide gene (Patent Document 7); diagnosis of arteriosclerotic lesions through measurement of apoB100 lipoprotein in blood (Patent Document 8); measurement of human phospholipid transfer protein (PLTP) with use of a monoclonal antibody against PLTP (Patent Document 9); use of an apo lipoprotein A-I antibody as a marker for diagnosing arteriosclerosis (Patent Document 10); and the like.

In addition, regarding other means related to the diagnosis of an arteriosclerotic lesion, the followings have been proposed: diagnosis of hyperlipemia or arteriosclerotic lesions with use of an antibody against a sodium dependent bile acid transporter protein (Patent Document 11); diagnosis through measurement of the coagulation factor VII-activating protease (FSAP) as a risk factor for atherosclerosis (Patent Document 12); examination of arteriosclerosis through detection of an endothelial and smooth muscle cell-derived neuropilin-like molecule (ESDN) or the gene expression thereof (Patent Document 13); use of an anti-human hepatic triglyceride lipase antibody (Patent Document 14); diagnosis of arteriosclerotic lesions by using the serotonin concentration in a plasma sample as a marker (Patent Documents 15 and 16); and the like.

Furthermore, regarding yet other means related to the diagnosis of an arteriosclerotic lesion, the followings have been proposed: diagnosis of chronic renal failure or atherosclerosis by using, as the analyte, an sMAD3 polypeptide which is an iso-form of MAD required for the signal transduction of DPP which is a TGF-family member of cytokine/growth factor (Patent Document 17); measurement of a complex of Lp-α and α2-macroglobulin/interleukin 6 in blood as the analyte by an immunological means using an antibody thereof (Patent Document 18); use of a monoclonal antibody against a paraoxonase (Patent Document 19); detection of arteriosclerosis through measurement of a saturated ultra long-chain fatty acid (Patent Document 20); diagnosis of atherosclerosis by using an RC-9 protein and an antibody thereof (Patent Document 21); and the like.

In this way, many methods have been proposed regarding the biochemical examination related to the diagnosis of an arteriosclerotic lesion. However, most of the detection markers of them are risk markers. For more radical and specific diagnosis of an arteriosclerotic lesion, an advanced development of markers capable of specifically detecting such a lesion has been demanded.

Therefore, Patent Document 22 has proposed, as a marker for specifically detecting an arteriosclerotic lesion, a polypeptide marker for diagnosing arteriosclerosis, a gene marker for diagnosing arteriosclerosis, an antibody specifically bindable to the polypeptide marker for diagnosing arteriosclerosis, a probe for detecting the gene marker for diagnosing arteriosclerosis, and a method for detecting an arteriosclerotic lesion.

Patent Document 1: Japanese Unexamined Patent Application, First Publication No. 2002-48790
Patent Document 2: Japanese Unexamined Patent Application, First Publication No. 2002-17353
Patent Document 3: Japanese Unexamined Patent Application, First Publication No. 2000-184885
Patent Document 4: Japanese Unexamined Patent Application, First Publication No. H10-142226
Patent Document 5: Japanese Unexamined Patent Application, First Publication No. H9-203736
Patent Document 6: Japanese Unexamined Patent Application, First Publication No. 2002-181820
Patent Document 7: Japanese Unexamined Patent Application, First Publication No. 2002-142781
Patent Document 8: Japanese Unexamined Patent Application, First Publication No. 2002-55106
Patent Document 9: Japanese Unexamined Patent Application, First Publication No. H11-346782
Patent Document 10: Japanese Unexamined Patent Application, First Publication No. H8-160042
Patent Document 11: Japanese Unexamined Patent Application, First Publication No. 2003-310281
Patent Document 12: Japanese Unexamined Patent Application, First Publication No. 2003-304873
Patent Document 13: Japanese Unexamined Patent Application, First Publication No. 2003-189872
Patent Document 14: Japanese Unexamined Patent Application, First Publication No. 2002-308900
Patent Document 15: Japanese Unexamined Patent Application, First Publication No. 2002-277461
Patent Document 16: Japanese Unexamined Patent Application, First Publication No. 2002-131313
Patent Document 17: Japanese Unexamined Patent Application, First Publication No. 2002-238589
Patent Document 18: Japanese Unexamined Patent Application, First Publication No. 2001-249128
Patent Document 19: Japanese Unexamined Patent Application, First Publication No. 2000-333674
Patent Document 20: Japanese Unexamined Patent Application, First Publication No. 2000-206113
Patent Document 21: Published Japanese translation No. 2000-503764 of PCT International Publication
Patent Document 22: Japanese Unexamined Patent Application, First Publication No. 2005-168498
Non-Patent Document 1: N. Eng. J. Med., 326, 242-250, 1992,
Non-Patent Document 2: Journal of Biological Chemistry, 272, 556, 1997.

According to the technique of Patent Document 22, an arteriosclerotic lesion can be detected with easy manipulation, and an early detection of arteriosclerosis can be expected. However, it does not satisfy an adequate level. There has been a demand for more accurate detection of an arteriosclerotic lesion with use of a greater number of polypeptide markers for diagnosing arteriosclerosis, gene markers for diagnosing arteriosclerosis, and the like.

Therefore, it is an object of the present invention to provide polypeptide markers for diagnosing arteriosclerosis, gene markers for diagnosing arteriosclerosis, antibodies, probes for detecting an arteriosclerosis marker gene, a DNA microarray or a DNA chip for detecting an arteriosclerosis marker gene, a method for detecting arteriosclerosis, and a kit for diagnosing arteriosclerosis, with which an arteriosclerotic lesion can be detected with much improved accuracy.

DISCLOSURE OF INVENTION

The inventors of the present invention have searched for proteins which are expressed in serum of a diseased patient with an arteriosclerotic lesion so as to find out more markers for diagnosing arteriosclerosis which can specifically detect an arteriosclerotic lesion. As a result, they found out novel polypeptide markers for diagnosing arteriosclerosis which can specifically detect an arteriosclerotic lesion, which has led to the completion of the present invention.

In the specific search method, the screening was conducted in the following manner by using serum of diseased patients with arteriosclerotic lesions who had been hospitalized in a hospital or cooperative institutes with the consent of patients or their families. The obtained cDNA clone was inserted in a plasmid pBluescript II to determine the nucleotide sequence. Thereafter, it was recombined in a pGEX plasmid and transfected in $E.$ $coli.$ The protein was abundantly expressed with IPTG (isopropyl β-D-thiogalactoside) to thereby prepare the protein extract, Next, the protein extract was solid-phased in a 96-well plate. The antibody level in the serum was measured by the ELISA method. Using these measured values, a significance test was conducted between the arteriosclerosis patient group and the normal group. As a result, significant differences were found between the patient group and the normal group with thirteen clones serving as the marker of the present invention. Furthermore, the reaction between the protein extract and a large number of patient serums was examined by the western blotting method. As a result, five clones serving as the marker of the present invention newly exhibited a positive reaction with the serums of diseased patients with arteriosclerotic lesion, by which these five clones were found to be useful as specific markers for the presence of an arteriosclerotic lesion, or for an unstable plaque. Then, it became possible by utilizing the antigenicity of these clones or probes for these genes, to develop a method for detecting arteriosclerosis, and moreover to produce a diagnosis kit for use in such a detection method.

That is, the present invention includes polypeptide markers for diagnosing arteriosclerosis, gene markers for diagnosing arteriosclerosis, antibodies, probes for detecting an arteriosclerosis marker gene, a DNA microarray or a DNA chip for detecting an arteriosclerosis marker gene, a method for detecting arteriosclerosis, and a kit for diagnosing arteriosclerosis, which are described below.

[1] A polypeptide marker for diagnosing arteriosclerosis, which comprises a polypeptide having an amino acid sequence set forth in any one of SEQ ID NOs: 1, 3, 5, 7, 9, 11, 13, 15, 17, 19, 21, 23, 25, 27, 29, 31, 33, and 35 of the Sequence Listing, or a partial amino acid sequence thereof.

[2] A gene marker for diagnosing arteriosclerosis, which comprises a gene represented by a nucleotide sequence that encodes the amino acid sequence of the polypeptide marker for diagnosing arteriosclerosis according to [1], or a partial amino acid sequence thereof.

[3] A gene marker for diagnosing arteriosclerosis, which comprises a gene having a nucleotide sequence set forth in any one of SEQ ID NOs: 2, 4, 6, 8, 10, 12, 14, 16, 18, 20, 22, 24, 26, 28, 30, 32, 34, and 36 of the Sequence Listing, or a partial nucleotide sequence thereof.

[4] An antibody specifically bindable to the polypeptide according to [1] as an antigen.

[5] A probe for detecting an arteriosclerosis marker gene, which comprises all or a part of DNA that is hybridizable with the gene according to [2] or [3] under a stringent condition.

[6] The probe for detecting an arteriosclerosis marker gene according to [5], which comprises all or a part of antisense DNA for the gene according to [3].

[7] A DNA microarray or a DNA chip for detecting an arteriosclerosis marker gene, wherein the probe for detecting an arteriosclerosis marker gene according to [5] and/or the probe for detecting an arteriosclerosis marker gene according to [6] is/are immobilized on a base plate.

[8] A method for detecting arteriosclerosis, wherein the antibody according to [4] is used to detect the expression of an arteriosclerosis marker polypeptide that is specifically bindable to the antibody, in a specimen sample.

[9] A method for detecting arteriosclerosis, wherein the polypeptide marker for diagnosing arteriosclerosis according to [1] is used to detect the expression of an antibody that is specifically bindable to the polypeptide marker for diagnosing arteriosclerosis, in specimen blood.

[10] A method for detecting arteriosclerosis, wherein the probe for detecting an arteriosclerosis marker gene according to [5] or [6] is used to detect the expression of a gene that is hybridizable with the probe for detecting an arteriosclerosis marker gene, in a specimen cell.

[11] A method for detecting arteriosclerosis, wherein a primer is constructed based on a nucleotide sequence set forth in any one of SEQ ID NOs: 2, 4, 6, 8, 10, 12, 14, 16, 18, 20, 22, 24, 26, 28, 30, 32, 34, and 36 of the Sequence Listing, and PCR is conducted with use of the primer to detect the expression of an arteriosclerosis marker gene.

[12] A kit for diagnosing arteriosclerosis, including at least one item selected from the group consisting of the probe for detecting an arteriosclerosis marker gene according to [5] or [6], the DNA microarray or the DNA chip for detecting an arteriosclerosis marker gene according to [7], and the antibody according to [4].

[13] A kit for diagnosing arteriosclerosis, including a polypeptide marker for diagnosing arteriosclerosis which comprises a polypeptide having an amino acid sequence set forth in any one of SEQ ID NOs: 1, 3, 5, 7, 9, 11, 13, 15, 17, 19, 21, 23, 25, 27, 29, 31, 33, and 35 of the Sequence Listing, or a partial amino acid sequence thereof.

An arteriosclerotic lesion can be detected with much higher accuracy by using the polypeptide marker for diagnosing arteriosclerosis, the gene marker for diagnosing arteriosclerosis, the antibody, the probe for detecting an arteriosclerosis marker gene, the DNA microarray or the DNA chip for detecting an arteriosclerosis marker gene, the method for detecting arteriosclerosis, and the kit for diagnosing arteriosclerosis of the present invention.

BRIEF DESCRIPTION OF THE DRAWINGS

FIG. 1 shows the results of the expression of arteriosclerosis marker genes by the western blotting method in the Examples.

DESCRIPTION OF EMBODIMENTS

The polypeptide marker for diagnosing arteriosclerosis and the gene marker for diagnosing arteriosclerosis of the present invention can be used for the detection of arteriosclerosis as they are specifically expressed in arteriosclerotic lesions. Polypeptides serving as the polypeptide marker for diagnosing arteriosclerosis of the present invention are polypeptides having an amino acid sequence set forth in any one of SEQ ID NOs: 1, 3, 5, 7, 9, 11, 13, 15, 17, 19, 21, 23, 25, 27, and 29 of the Sequence Listing, or a partial amino acid sequence thereof.

Here, the term "partial amino acid sequence" refers to a sequence being a part of the amino acid sequence set forth in any one of SEQ ID NOs of the Sequence Listing mentioned above, consisting of four or more, preferably five or more, more preferably six or more, and yet more preferably seven or more amino acids.

The information on the amino acid sequences of the above-mentioned polypeptides of the present invention are available from the NCBI GeneBank database as of Jul. 31, 2008, with the accession numbers: XM_001129783 (SEQ ID NO: 1), NM_006088 (SEQ ID NO: 3), NM_014878 (SEQ ID NO: 5), NM_207514 (SEQ ID NO: 7), NM_001128847 (SEQ ID NO: 9), NM_001017408 (SEQ ID NO: 11), NM_015089 (SEQ ID NO: 13), NM_133337 (SEQ ID NO: 15), NM_022406 (SEQ ID NO: 17), NM_001402 (SEQ ID NO: 19), NM_005349 (SEQ ID NO: 21), NM_005406 (SEQ ID NO: 23), NM_016436 (SEQ ID NO: 25), NM_032408 (SEQ ID NO: 27), and NM_014377 (SEQ ID NO: 29).

In addition, the gene marker for diagnosing arteriosclerosis of the present invention comprises a gene represented by a nucleotide sequence which encodes the above-mentioned polypeptide having the amino acid sequence or a partial amino acid sequence thereof. The gene marker for diagnosing arteriosclerosis may be a gene having a nucleotide sequence capable of expressing the above-mentioned polypeptide.

The gene serving as the gene marker for diagnosing arteriosclerosis of the present invention can be exemplified by genes of the following clones, as well as being genes having a nucleotide sequence set forth in any one of SEQ ID NOs: 2, 4, 6, 8, 10, 12, 14, 16, 18, 20, 22, 24, 26, 28, 30, 32, 34, and 36 of the Sequence Listing, or a partial nucleotide sequence thereof. The information on these genes (nucleotide sequence information) are respectively available from the NCBI GeneBank database, with the following accession numbers.

That is, the gene serving as the gene marker for diagnosing arteriosclerosis can be exemplified by [Clone Name: S19A3; SEQ ID NO: 2 of the Sequence Listing; Accession No, XM_001129783; Gene Name: (PREDICTED) similar to LIM and senescent domain 1 (LOC729260); Gene Description: similar to the LIMS1 gene. LIMS1 is an adaptor protein which contains five LIM domains, or double zinc fingers. LIMS1 may possibly play a role in integrin-mediated cell adhesion or spreading.], [Clone Name: TS27A2; SEQ ID NO: 4 of the Sequence Listing; Accession No. NM_006088; Gene Name: tubulin, beta 2C (TUBB2C); Gene Description: a component protein of microtubules], [Clone Name: S21B1; SEQ ID NO: 6 of the Sequence Listing; Accession No. NM_014878; Gene Name: KIAA0020 (KIAA0020); Gene Description; reportedly a minor histocompatibility antigen], [Clone Name: S25E1; SEQ ID NO: 8 of the Sequence Listing; Accession No. NM_207514; Gene Name: differentially expressed in FDCP 8 homolog (mouse) (DEF8); Gene Description: unknown function], [Clone Name: TS12D2; SEQ ID NO: 10 of the Sequence Listing; Accession No. NM_001128847; Gene Name: SWI/SNF related, matrix associated, actin dependent regulator of chromatin, subfamily a, member 4 (SMARCA4); Gene Description: unknown], [Clone Name: S36C3; SEQ ID NO: 12 of the Sequence Listing; Accession No. NM_001017408; Gene Name: golgi associated PDZ and coiled-coil motif containing (GOPC); Gene Description: bindable to Rhotekin, an effector of a low molecular weight GTP-binding protein Rho. Moreover, reportedly, the binding between Rhotekin and GOPC is regulated in a Rho dependent manner.], [Clone Name: N48B1; SEQ ID NO: 14 of the Sequence Listing; Accession No. NM_015089; Gene Name: p53-associated parkin-like cytoplasmic protein (PARC); Gene Description: associated with transition from metaphase to anaphase during cell division, and also associated with ubiquitin-dependent protein degradation], [Clone Name: S28D1; SEQ ID NO: 16 of the Sequence Listing; Accession No. NM 133337; Gene Name: fer-1-like 3, myoferlin (*C. elegans*) (FER1L3); Gene Description: a type II membrane protein similar to a skeletal muscle protein, dysferlin, this gene having a C2 domain is suggested to be possibly associated with regeneration and repair of cytoplasmic membrane and nuclear membrane], [Clone Name: TS27H1; SEQ ID NO: 18 of the Sequence Listing; Accession No. NM_022406; Gene Name: X-ray repair complementing defective repair in Chinese hamster cells 4 (XRCC4); Gene Description: a protein encoded by this gene acts to complete the repair of a DNA double strand through nonhomologous end-joining and V(D)J recombination, together with DNA ligase IV and DNA-dependent protein kinase. The nonhomologous end-joining pathway is necessary for the normal development and suppression on tumors.], [Clone Name: PA105; SEQ ID NO: 20 of the Sequence Listing; Accession No. NM_031229; Gene Name: RanBP-type and C3HC4-type zinc finger containing 1 (RBCK1); Gene Description: unknown function. Its amino acid sequence is similar to that of mouse UIP28/UbcM4 interacting protein], [Clone Name: S16D2; SEQ ID NO: 22 of the Sequence Listing; Accession No. NM_005349; Gene Name: recombination signal binding protein for immunoglobulin kappa J region (RBPJ); Gene Description: unknown], [Clone Name: S27D3; SEQ ID NO: 24 of the Sequence Listing; Accession No. NM_005406; Gene Name: Rho-associated, coiled-coil containing protein kinase 1 (ROCK1); Gene Description: serine/threonine kinase activated by a low molecular weight GTP-binding protein Rho, and associated not only with cell contraction but also with morphological regulation, migration, regulation of gene expression, and like physiological functions.], [Clone Name: S36E1; SEQ ID NO: 26 of the Sequence Listing; Accession No. NM_016436; Gene Name: PHD finger protein 20 (PHF20); Gene Description: associated with DNA-dependent transcriptional regulation.], [Clone Name: S39D6; SEQ ID NO: 28 of the Sequence Listing; Accession No. NM_032408; Gene Name: bromodomain adjacent to zinc finger domain, 1B (BAZ1B); Gene Description: a member of the bromodomain protein family involved in chromatin-dependent regulation of transcription.], [Clone Name: TS27B2; SEQ ID NO: 30 of the Sequence Listing; Accession No. NM_014377; Gene Name: zuotin related factor 1 (ZRF1); Gene Description: a member of the M-phase phosphoprotein family, acting as a molecular chaperone.], [Clone Name: PA202; SEQ ID NO: 32 of the Sequence Listing; Accession No. NM_003692; Gene Name: transmembrane protein with EGF-like and two follistatin-like domains 1 (TMEFF1); Gene Description: reportedly inhibits nodal signaling through binding to the nodal coreceptor Cripto in *Xenopus*], [Clone Name: PA213; SEQ ID NO: 34 of the Sequence Listing; Accession No. NM_006807; Gene Name: chromobox homolog 1 (HP1 beta homolog *Drosophila*) (CBX1); Gene Description: localized at heterochromatin sites, where it mediates gene silencing.], [Clone Name: PA234; SEQ ID NO: 36 of the Sequence Listing; Accession No. BC030642; Gene Name: PARK2 co-regulated (PACRG); Gene Description: Parkinson's disease-associated gene, and reportedly regulated by the ubiquitin-proteasome system.].

In addition, the term "partial nucleotide sequence" refers to a sequence being a part of the nucleotide sequence set forth in any one of SEQ ID NOs of the Sequence Listing mentioned above, consisting of twelve or more, preferably fifteen or more, more preferably eighteen or more, and yet more preferably twenty or more nucleotides (hereunder, the same definition will be applied).

The above-mentioned genes serving as the gene marker for diagnosing arteriosclerosis are summarized in Table 1.

TABLE 1

| | Clone Name | SEQ ID NO. | Accession No. | Gene Name |
|---|---|---|---|---|
| 1 | S19A3 | 2 | XM_001129783 | (PREDICTED) similar to LIM and senescent domain 1 (LOC729260) |
| 2 | TS27A2 | 4 | NM_006088 | tubulin, beta 2C (TUBB2C) |
| 3 | S21B1 | 6 | NM_014878 | KIAA0020 (KIAA0020) |
| 4 | S25E1 | 8 | NM_207514 | differentially expressed in FDCP 8 homolog (mouse) (DEF8) |
| 5 | TS12D2 | 10 | NM_001128847 | SWI/SNF related, matrix associated, actin dependent regulator of chromatin, subfamily a, member 4 (SMARCA4) |
| 6 | S36C3 | 12 | NM_001017408 | golgi associated PDZ and coiled-coil motif containing (GOPC) |
| 7 | N48B1 | 14 | NM_015089 | p53-associated parkin-like cytoplasmic protein (PARC) |
| 8 | S28D1 | 16 | NM_133337 | fer-1-like 3, myoferlin (*C. elegans*) (FER1L3) |
| 9 | TS27H1 | 18 | NM_022406 | X-ray repair complementing defective repair in Chinese hamster cells 4 (XRCC4) |
| 10 | PA105 | 20 | NM_031229 | RanBP-type and G3HC4-type zinc finger containing 1 (RBCK1) |
| 11 | S16D2 | 22 | NM_005349 | recombination signal binding protein for immunoglobulin kappa J region (RBPJ) |
| 12 | S27D3 | 24 | NM_005406 | Rho-associated, coiled-coil containing protein kinase 1 (ROCK1) |
| 13 | S36E1 | 26 | NM_016436 | PHD finger protein 20 (PHF20) |
| 14 | S39D6 | 28 | NM_032408 | bromodomain adjacent to zinc finger domain, 1B (BAZ1B) |
| 15 | TS27B2 | 30 | NM_014377 | zuotin related factor 1 (ZRF1) |

TABLE 1-continued

| Clone Name | SEQ ID NO. | Accession No. | Gene Name |
|---|---|---|---|
| 16 PA202 | 32 | NM_003692 | transmembrane protein with EGF-like and two follistatin-like domains 1 (TMEFF1) |
| 17 PA213 | 34 | NM_006807 | chromobox homolog 1 (HP1 beta homolog *Drosophila*) (CBX1) |
| 18 PA234 | 36 | BC030642 | PARK2 co-regulated (PACRG) |

The antibody of the present invention is an antibody specifically bindable to, as an antigen, a polypeptide serving as the above-mentioned polypeptide marker for diagnosing arteriosclerosis. The antibody may be either monoclonal or polyclonal. These antibodies can be produced by a usual method using the above-mentioned polypeptide as an antigen.

The antibody of the present invention may be labeled with a labeling substance. As for the labeling substance, it is possible to use an enzyme, a radioisotope, a fluorescent dye, biotin, digoxigenin, or the like. The enzyme is not specifically limited as long as it fulfills the requirements such as a large turnover number (number of revolution), stability in the antibody-binding state, and capability of rendering the substrate a specific color. For example, peroxidases for use in usual EIA (enzyme immunoassay), β-galactosidase, alkaline phosphatase, glucose oxidase, acetylcholine esterase, glucose-6-phosphate dehydrogenase, malate dehydrogenase, or the like can be used. In addition, it is also possible to use an enzyme inhibitory substance, a coenzyme, or the like. These enzymes can be bound to the antibody by a known method using a maleimide compound or such a crosslinking agent.

As for the substrate, it is possible to use a known substance according to the type of the enzyme to be used. For example, 3,3',5,5'-tetramethylbenzidine can be used as a substrate when peroxidase is used as an enzyme, while paranitrophenol can be used as a substrate when alkaline phosphatase is used as an enzyme.

As for the radioisotope, it is possible to use $^{125}$I, $^3$H, or such a substance for use in usual RIA (radioimmunoassay).

As for the fluorescent dye, it is possible to use fluorescein isothiocyanate (FITC), tetramethylrhodamine isothiocyanate (TRITC), or such a substance for use in usual fluorescence antibody technique.

In addition, these labeled antibodies may be tagged with a metal such as manganese or iron. By administering such a metal-tagged antibody into the body and assaying the metal by MRI or such a means, the presence of an antigen peptide bound to this antibody (a polypeptide marker for diagnosing arteriosclerosis) can be detected.

In addition, the probe for detecting an arteriosclerosis marker gene of the present invention is a probe which comprises all or a part of DNA that is hybridizable with the gene serving as the gene marker for diagnosing arteriosclerosis mentioned above under a stringent condition. Here, the term "stringent condition" of the present invention can be exemplified by: hybridization in a buffer solution containing 50% formamide, 5×SSC, 5×Denhardt's solution, 0.1M sodium dihydrogenphosphate (pH6.5), 0.5% SDS, and 100 µg/ml denatured salmon sperm DNA, at 42° C., followed by a washing treatment in a buffer solution containing 1×SSC (0.15M NaCl and 0.015M sodium citrate) and 0.1% SDS (sodium dodecyl sulfate) at 42° C. (Condition 1); or, hybridization in a buffer solution containing 5×SSC, 5×Denhardt's solution, 0.1M sodium dihydrogenphosphate (pH6.5), 0.5% SDS, and 100 µg/ml denatured salmon sperm DNA, at 65° C., followed by a washing treatment in a buffer solution containing 0.1× SSC and 0.1% SDS at 65° C. (Condition 2). The latter (Condition 2) is more preferred. As for the factors to influence the stringency of hybridization, there are various kinds of factors other than the temperature condition mentioned above. It is possible for those skilled in the art to combine various kinds of such factors to achieve equivalent stringency to the stringency of hybridization exemplified above.

Moreover, the probe for detecting an arteriosclerosis marker gene of the present invention can be exemplified by a probe which comprises all or a part of antisense DNA for the gene having a nucleotide sequence set forth in any one of SEQ ID NOs: 2, 4, 6, 8, 10, 12, 14, 16, 18, 20, 22, 24, 26, 28, 30, 32, 34, and 36 of the Sequence Listing. That is, it is a probe which comprises DNA having a nucleotide sequence complementary to the nucleotide sequence set forth in any one of SEQ ID NOs mentioned above, or a partial nucleotide sequence thereof.

These probes for detecting an arteriosclerosis marker gene may be appropriately labeled with a fluorescent label or the like.

Moreover, the DNA microarray or the DNA chip for detecting an arteriosclerosis marker gene of the present invention is used for the detection of the expression of the gene serving as the gene marker for diagnosing arteriosclerosis mentioned above, and for the diagnosis of an arteriosclerotic lesion through the detection, wherein the above-mentioned probe for detecting an arteriosclerosis marker gene is immobilized on a base plate, Regarding the above-mentioned probe for detecting an arteriosclerosis marker gene to be immobilized, it is either possible to use a single kind or a plurality of kinds thereof.

The DNA microarray or the DNA chip can be produced by a usual method. The DNA microarray can be obtained by, for example, spotting a solution containing respective probe(s) for detecting an arteriosclerosis marker gene that has been prepared in advance on a base plate and drying this plate. In addition, the DNA chip can be obtained by, for example, synthesizing DNA having a desired nucleotide sequence on a base plate by photolithography.

Hereunder is a description of the method for detecting arteriosclerosis of the present invention.

The method for detecting arteriosclerosis of the present invention is a method in which the above-mentioned polypeptide marker for diagnosing arteriosclerosis is used to detect the expression of an antibody (arteriosclerosis marker antibody) that is specifically bindable to the polypeptide marker for diagnosing arteriosclerosis, in a specimen blood (hereunder, referred to as the "detection method (1)"). In the specimen blood collected from a diseased patient with an arteriosclerotic lesion, the above-mentioned arteriosclerosis marker antibody is induced by the expression of the polypeptide serving as the polypeptide marker for diagnosing arteriosclerosis. So, it is possible to detect arteriosclerosis through detection of the arteriosclerosis marker antibody with use of the polypeptide marker for diagnosing arteriosclerosis.

The detection method (1) can be specifically exemplified by a method in which: the solid-phased polypeptide marker for diagnosing arteriosclerosis is contacted with a serum collected from a test subject so that the marker can bind to antibodies in the serum; unbound proteins are removed; next a labeled antibody (secondary antibody) that is specifically bindable to the antibodies in the serum is added to allow a reaction therebetween; and the signal from the labeled antibody is detected. As to the labeling substance for the above-mentioned labeled antibody, it is possible to use an enzyme, a radioisotope, a fluorescent dye, biotin, digoxigenin, or the like, which has been enumerated as a substance to label the antibody of the present invention.

When an enzyme is used as a labeling substance, the amount of the antibody can be calculated by: adding a substrate which is decomposed to take a color by an enzymatic action; optically measuring the amount of the decomposed substrate to thereby obtain the enzymatic activity; converting this value into the amount of the antibody bound; and making a comparison between the converted value and a reference value. Alternatively, the amount of the antibody can also be obtained with high sensitivity by: adding a substrate which emits light by an enzymatic action; and measuring with a weak luminescence analyzer (luminometer).

When a radioisotope is used as a labeling substance, the amount of the antibody can be calculated by measuring the level of radiation emitted from the radioisotope with a scintillation counter or such a device. When a fluorescent dye is used as a labeling substance, the amount of the antibody can be calculated by measuring the quantity of fluorescence with a measurement device equipped with a fluorescence spectrometer or such a device.

In the detection method (1), the western blotting method can be applied. Moreover, it is also possible to isolate a conjugate of the polypeptide marker for diagnosing arteriosclerosis, the antibody of the specimen blood, and the labeled antibody, by a known isolation method (a chromatography method, a salting-out method, an alcohol precipitation method, an enzyme method, an in-phase method, or the like), followed by the detection of the signal from the labeled antibody.

Moreover, in the diagnosis of arteriosclerosis by using the detection method (1), it is also possible to examine whether or not the arteriosclerosis marker antibody (antibodies) is (are) present in the specimen blood collected from a test subject so as to determine that the test subject showing the presence of one or more types of arteriosclerosis marker antibodies is a diseased patient with an arteriosclerotic lesion, or a person with a high risk of an arteriosclerotic lesion.

In addition, the method for detecting arteriosclerosis of the present invention is a method in which the above-mentioned probe for detecting an arteriosclerosis marker gene is used to detect the expression of a gene (arteriosclerosis marker gene) that is hybridizable with the probe for detecting an arteriosclerosis marker gene, in a specimen cell (hereunder, referred to as the "detection method (2)"). In the specimen cell collected from a diseased patient with an arteriosclerotic lesion, the arteriosclerosis marker gene is expressed. So, it is possible to detect arteriosclerosis through detection of the expression of the arteriosclerosis marker gene with use of the probe for detecting an arteriosclerosis marker gene.

The detection method (2) can be specifically exemplified by a method in which: a probe for detecting an arteriosclerosis marker gene, which has a nucleotide sequence as mentioned above in a suitable length for hybridization is prepared; a fluorescence label or such a label is appropriately added thereto; this labeled probe is contacted with a sample collected from a specimen cell to perform a hybridization reaction; and the expression of the gene serving as the gene marker for diagnosing arteriosclerosis is detected.

In the detection method (2), it is possible to employ a known detection method except for using the probe for detecting an arteriosclerosis marker gene of the present invention. For example, a northern blotting method can be employed. Moreover, in the detection method (2), any one of the above-mentioned probes for detecting an arteriosclerosis marker gene can be used. It is either possible to use a single kind of probe for detecting an arteriosclerosis marker gene or a plurality of kinds of probes for detecting an arteriosclerosis marker gene.

In addition, the detection method (2) may also use a DNA microarray or a DNA chip in which the probe(s) for detecting an arteriosclerosis marker gene is/are immobilized on a base plate.

Furthermore, in the detection method (2), it is also possible to employ quantitative or semi-quantitative PCR (Polymerase Chain Reaction) in order to amplify the arteriosclerosis marker gene in the sample collected from the specimen cell. The PCR may be either RT-PCR (reverse transcription PCR) or real-time RT-PCR. For carrying out the PCR, a primer set including a sense primer and an antisense primer for amplifying the arteriosclerosis marker gene is used. These primers can be appropriately constructed based on a nucleotide sequence set forth in any one of SEQ ID NOs: 2, 4, 6, 8, 10, 12, 14, 16, 18, 20, 22, 24, 26, 28, 30, 32, 34, and 36 of the Sequence Listing.

On the completion of the amplification of the arteriosclerosis marker gene by such quantitative or semi-quantitative PCR in this way, the expression of the arteriosclerosis marker gene can be detected by using this sample. By so doing, the detection sensitivity can be improved.

Moreover, in the diagnosis of arteriosclerosis by using the detection method (2), it is possible to detect the arteriosclerosis marker gene in a test subject and compare the result with a result of a healthy subject detected by the same method to thereby determine that the test subject showing a large detection level is a diseased patient with an arteriosclerotic lesion, or a person with a high risk of an arteriosclerotic lesion.

In addition, the method for detecting arteriosclerosis of the present invention is a method in which the antibody bindable to, as an antigen, a polypeptide serving as the polypeptide marker for diagnosing arteriosclerosis of present invention, is used to detect the expression of a polypeptide (arteriosclerosis marker polypeptide) that is specifically bindable to the antibody, in a specimen sample (hereunder, referred to as the "detection method (3)"). In the specimen sample collected from a diseased patient with an arteriosclerotic lesion, the arteriosclerosis marker polypeptide is expressed. So, it is possible to detect arteriosclerosis through detection of the arteriosclerosis marker polypeptide with use of the antibody of the present invention.

The detection method (3) can be executed by a known immunoassay method except for using the antibody of the present invention. The immunoassay method can be exemplified by the western blotting method, the ELISA (Enzyme-Linked Immunosorbent Assay) method, a radioimmunoassay method, or a fluorescence antibody technique.

The antibody for use in the detection method (3) may be either monoclonal or polyclonal.

When the fluorescence antibody technique is applied to the detection method (3), either a direct fluorescence antibody test or an indirect fluorescence antibody test may be used. The direct fluorescence antibody test is a method in which an antibody for use in the detection is labeled with fluorescence, and then the antibody is contacted to a sample cell as being the test sample to bind them to each other so that a cell expressing the arteriosclerosis marker polypeptide can be labeled. In addition, the indirect fluorescence antibody test is a method in which a non-labeled antibody of the present invention is contacted to a sample cell to bind them to each other, and then the antibody is further bound to a labeled secondary antibody (anti-immunoglobulin antibody) so that a cell expressing the arteriosclerosis marker polypeptide can be labeled.

Moreover, when detecting arteriosclerosis through detection of the expression of the arteriosclerosis marker polypeptide, it is also possible, rather than using the antibody of the present invention as mentioned above, to use TOF-MASS to directly detect the arteriosclerosis marker polypeptide, or to use a chip in which a protein that is interactive with the arteriosclerosis marker polypeptide is immobilized on a base plate.

Moreover, in the diagnosis of arteriosclerosis by using the detection method (3), it is possible to examine whether or not the arteriosclerosis marker polypeptide(s) is (are) present in the specimen sample collected from a test subject so as to determine that the test subject showing the presence of one or more types of arteriosclerosis marker polypeptides is a diseased patient with an arteriosclerotic lesion, or a person with a high risk of an arteriosclerotic lesion.

The probe for detecting an arteriosclerosis marker gene for use in the detection of an arteriosclerotic lesion of the present invention, the DNA microarray or the DNA chip for detecting an arteriosclerosis marker gene in which the probe for detecting an arteriosclerosis marker gene is immobilized, and the antibody for detecting the arteriosclerosis marker polypeptide of the present invention can be prepared as a product of a kit for diagnosing arteriosclerosis which comprises at least one of these items and with which arteriosclerosis can be detected and diagnosed as mentioned above.

In addition, the polypeptide marker for diagnosing arteriosclerosis of the present invention can also be prepared as a product of a kit for diagnosing arteriosclerosis with which arteriosclerosis can be detected and diagnosed as mentioned above.

When the polypeptide marker for diagnosing arteriosclerosis, the gene marker for diagnosing arteriosclerosis, the antibody, and the probe for detecting an arteriosclerosis marker gene of the present invention described above are jointly used with those of the Patent Document 22, arteriosclerosis can be detected with much higher accuracy.

EXAMPLES

Hereunder is a detailed description of the present invention with reference to Examples. However, the present invention is not to be limited by the following description.

Production Example

Preparation of Samples (1) The subjects were patients with carotid artery stenoses who had visited our hospital or cooperative institutes. The reference (control) healthy subjects were selected from outpatients so that both groups had matched gender and age (±5 years). When they were visiting as outpatients or hospitalized in the neurosurgery department; 1) their families were explained that this study was to be conducted for research purposes and that cooperation with the study was not compulsory, and informed consents were obtained from them; 2) questions about the family history, the past history, the life style such as drinking and smoking habits, and the work style were asked; 3) blood was collected and separated into serum and corpuscle components and cryopreserved; and further more, 4) the clinical seriousness, the therapeutic process, the findings of the blood examination and the like were recorded on the basis of the medical record of the doctor. The patient blood as the analyte was separated into serum and cryopreserved at −80° C. until the study was started. The antibodies and the medical records were used after encryption and anonymization.

(2) Regarding the target of screening with serum, commercial λZAP II phage vectors (STRATAGENE) recombined with a human microvascular endothelium-derived cDNA library were used.

(Expression Cloning Method)

(3) The screening by the expression cloning method was conducted with reference to the method of St John, T et. al. (Science, 231, 845-850, 1986).

1) The above-mentioned phage vector of (2) was infected into E. coli (XL1-Blue) and cultured on a NZY agar medium (φ15 cm dish).

2) After confirming the emergence of plaques, an IPTG-treated nitrocellulose membrane was placed on the medium, and the phage-derived protein was expressed and transferred to the nitrocellulose membrane.

3) The patient serum which had been diluted 2000-fold with 1% BSA/PBS and the nitrocellulose membrane were incubated overnight to cause a reaction between the expression proteins and the antibodies in the serum (serum IgG).

4) After washing, the alkaline phosphatase-labeled goat anti-human IgG antibody as a secondary antibody was reacted with the nitrocellulose membrane.

5) Serum IgG-recognizing clones were identified by using NBT (nitroblue terazolium) and BCIP (5-bromo-4-chloro-3-indolyl-phosphate) as a coloring reagent.

6) The positive clones were subjected to secondary and tertiary screening (in φ10 cm dish) and false positive clones were removed.

7) The selected phage was converted to pBlueScript with the ExAssist helper phage system (Stratagene, La Jolla, Calif.).

8) The plasmid was purified with use of the Plasmid Miniprep kit (Sigma).

9) The nucleotide sequences of the obtained clones were determined by a sequencer, and were subjected to a homology search using published databases. By so doing, the genes were identified and these clones were used as candidate antigen proteins.

(ELISA Method)

(4) ELISA Method as Secondary Screening

1) The pBluescript including the insert of the candidate antigen protein was recombined into a protein expression and purification vector pGEX-4T (Amersham Bioscience). From the obtained nucleotide sequence information, restriction enzymes suitable for the recombination from pBluescript to pGEX-4T were selected, and treatments were done with restriction enzymes such as BamH I, Sal I, Not I, EcoR I, Xho I, and Sma I.

2) After agarose gel electophoresis, the band of interest was cut out by using the purification kit GeneElute Minus EtBr Spin Columns (SIGMA), and the restriction enzyme digested insert and the pGEX-4T were recovered.

3) The insert and the pGEX-4T were ligated with the Ligation-Convenience Kit (Nippongene) to thereby produce a plasmid containing the insert.

4) When there was no restriction enzyme suitable for some clones, the inserts thereof were produced by PCR. Primers having a restriction enzyme recognition site were produced in advance, and RNA extracted from aneurysmal tissue was used as a template to conduct reverse transcription PCR.

Thereby, cDNA was produced. Another PCR was conducted to obtain the total length of the insert. Thereafter, the same treatment was carried out using the restriction enzymes and the ligation kit.

5) The obtained recombinant pGEX-4T was used to transform E. coli competent cell BL21 (Nippongene) modified for eukaryotic protein expression.

6) This product was cultured in an ampicillin-containing LB medium, and the expression of the insert DNA-derived protein was induced with IPTG.

7) E. coli was recovered through centrifugal separation and ruptured by sonication to separate into a soluble fraction and an insoluble fraction.

8) If the target protein was in the insoluble fraction, this was solubilized by using urea.

9) The antigen protein was purified with the glutathione-Sepharose (Amersham Pharmacia).

10) The antigen protein was injected in a 96-well ELISA plate at a concentration of 10 µg/ml, stored at 4° C. overnight, and solid-phased.

11) After washing with PBS and blocking with a PBS solution containing 10% fetal bovine serum, patient serum and control serum (serum of healthy subject) were diluted 2000-fold and reacted with the solid-phased protein.

12) After washing with PBS, HRP-labeled goat anti-human IgG antibody was added.

13) A color was developed by adding a substrate, and the absorption at OD 490 nm was measured using a plate reader.
(Western Blotting Method)
(5) Secondary Screening by Western Blotting Method 1) E. coli (SOLR, JM109, BL21) transformed with the pBluescript or the pGEX-4T including the insert of the candidate antigen protein obtained from the above, was cultured with 2 ml of LB ampicillin (50 µg/ml) overnight.

2) This was transferred to 20 ml of LB ampicillin and cultured for one hour, and was then added with IPTG to give a final concentration of 1 mM. The resultant sample with IPTG and a control sample (without the addition of IPTG) were cultured for another 3 hours.

3) The culture liquid was centrifuged, and E. coli was recovered therefrom. This was dissolved with a SDS sample buffer for use as a sample of the western method.

4) This sample was electrophoresed on a 10% polyacrylamide gel, and the protein was transferred to a nitrocellulose membrane using a blotting apparatus.

5) This was blocked with 1% skim milk and then was added with a 2000-fold diluted patient serum as a primary antibody, followed by overnight incubation.

6) After washing with PBST (20 mM Tris-HCl (pH 7.6), 50 mM NaCl, 0.1% Tween-20), 30,000-fold diluted HRP-labeled goat anti-human IgG antibody was added and allowed to react for 20 minutes.

7) After washing with PBST, a luminescent reagent Immobilon Western (MILLIPORE) was used to effect light emission.

8) The membrane was exposed to a film and developed.

9) The band which became detectable depending on the IPTG treatment was assumed to be of an antigen protein.
Verification of the Gene Marker for Diagnosing Arteriosclerosis by Sequencing The nucleotide sequences of the genes (gene markers for diagnosing arteriosclerosis) of the detected clones were determined by sequencing. The thus determined nucleotide sequences were cross-checked with nucleotide sequences in published gene databases. As a result, the genes of the obtained clones had consistent nucleotide sequences with those of the genes that encode the polypeptides for diagnosing arteriosclerosis mentioned above.

Example 1

Measurement of the Antibody Titer by ELISA Method

Using the experimental protocol of the Production Example mentioned above, the antibody levels of the thirteen out of the eighteen types of the detected arteriosclerosis diagnostic marker candidates were measured by ELISA, and the presence of the serum antibodies was confirmed. The results of the measurement are shown in Table 2.

TABLE 2

|  | Patient (P) | | | Healthy subject (N) | |
| --- | --- | --- | --- | --- | --- |
| Clone name | Average | Standard deviation | p value (two-sided) | Average | Standard deviation |
| S19A3 | 0.386 | 0.00912 | 0.0000 | 0.272 | 0.0624 |
| TS27A2 | 0.306 | 0.1246 | 0.0011 | 0.229 | 0.0909 |
| S21B1 | 0.206 | 0.1271 | 0.0078 | 0.146 | 0.0779 |
| S25E1 | 0.346 | 0.3338 | 0.0145 | 0.210 | 0.1515 |
| TS12D2 | 0.318 | 0.1959 | 0.0227 | 0.242 | 0.1019 |
| S36C3 | 0.050 | 0.0407 | 0.0281 | 0.035 | 0.0207 |
| N48B1 | 0.211 | 0.1109 | 0.0472 | 0.165 | 0.1065 |
| S28D1 | 0.493 | 0.2525 | 0.0642 | 0.400 | 0.2251 |
| TS27H1 | 0.093 | 0.0827 | 0.0645 | 0.067 | 0.0393 |
| PA105 | 0.256 | 0.1414 | 0.0000 | 0.1417 | 0.0891 |
| PA202 | 0.289 | 0.1546 | 0.0097 | 0.2157 | 0.1054 |
| PA213 | 0.440 | 0.2052 | 0.0002 | 0.2955 | 0.1368 |
| PA234 | 0.150 | 0.1001 | 0.0131 | 0.1046 | 0.0705 |

Example 2

Verification of the Expression of Arteriosclerosis Marker Genes by Western Blotting Method The five types of clones of the candidate gene markers identified by the expression cloning method, that is, those unused in Example 1, were verified for the expression of the arteriosclerosis marker gene in arteriosclerosis patients by the western blotting method. The detection results thereof are shown in FIG. 1 (positive signal in western blots is indicated by the arrow in the FIGURE.). FIG. 1(a) shows the results of Clone Name: S16D2 (SEQ ID NO: 22 of the Sequence Listing), FIG. 1(b) shows the results of Clone Name: S27D3 (SEQ ID NO: 24 of the Sequence Listing), FIG. 1(c) shows the results of Clone Name: S36E1 (SEQ ID NO: 26 of the Sequence Listing), FIG. 1(d) shows the results of Clone Name: S39D6 (SEQ ID NO: 28 of the Sequence Listing), and FIG. 1(e) shows the results of Clone Name: TS27B2 (SEQ ID NO: 30 of the Sequence Listing).

As shown in Table 2, with the thirteen types of candidate gene markers for diagnosing arteriosclerosis obtained from the screening of this Example, the measurement by the ELISA method showed a difference between the antibody titer of patients and the antibody titer of healthy subject serums. Furthermore, with eleven types of candidate gene markers, a significant difference was found.

In addition, as shown in FIG. 1, with five types of candidate gene markers obtained from the screening of this Example, positive signals for the specific reaction were confirmed by the western blotting method.

INDUSTRIAL APPLICABILITY

According to the polypeptide markers for diagnosing arteriosclerosis, the gene markers for diagnosing arteriosclerosis, the antibodies, the probes for detecting the arteriosclerosis marker genes, the DNA microarray or the DNA chip for detecting the arteriosclerosis marker genes, the method for detecting arteriosclerosis, and the kit for diagnosing arteriosclerosis of the present invention, arteriosclerosis can be readily detected with high accuracy. These can be favorably used for the early stage diagnosis of arteriosclerosis.

The invention claimed is:

1. A method of diagnosing arteriosclerosis in a subject comprising:

obtaining a serum sample from the subject;

determining the presence in the serum sample of an antibody capable of forming a complex with a solid-phased polypeptide having an amino acid sequence set forth in SEQ ID NO: 31 of the Sequence Listing, or a fragment thereof, using a process comprising contacting the solid-phased polypeptide with the serum sample under conditions that allow for antibodies in the serum sample to form a complex with the polypeptide, exposing the antibody-peptide complex to a second antibody capable of binding to the antibodies in the antibody-peptide complex, and detecting a signal from the second antibody indicating the presence in the serum of an antibody capable of forming a complex with the amino acid sequence set forth in SEQ ID NO: 31 of the Sequence Listing, or a fragment thereof; and diagnosing arteriosclerosis in the subject if antibodies are identified in the serum that are capable of forming a complex with the amino acid sequence set forth in SEQ ID NO: 31 of the Sequence Listing, or a fragment thereof.

* * * * *